(12) United States Patent
DiLillo et al.

(10) Patent No.: US 12,291,559 B2
(45) Date of Patent: *May 6, 2025

(54) COMPOSITIONS AND METHODS FOR TREATING CANCER

(71) Applicant: Regeneron Pharmaceuticals, Inc., Tarrytown, NY (US)

(72) Inventors: David DiLillo, Tarrytown, NY (US); Thomas Craig Meagher, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/382,284

(22) Filed: Oct. 20, 2023

(65) Prior Publication Data

US 2024/0165157 A1    May 23, 2024

Related U.S. Application Data

(63) Continuation of application No. 17/307,235, filed on May 4, 2021, now Pat. No. 11,826,386.

(60) Provisional application No. 63/020,177, filed on May 5, 2020.

(51) Int. Cl.
| | |
|---|---|
| *C07K 14/725* | (2006.01) |
| *A61K 38/00* | (2006.01) |
| *A61K 39/00* | (2006.01) |
| *A61K 40/11* | (2025.01) |
| *A61K 40/31* | (2025.01) |
| *A61K 40/42* | (2025.01) |
| *C07K 14/705* | (2006.01) |
| *C12N 5/0783* | (2010.01) |

(52) U.S. Cl.
CPC .......... *C07K 14/7051* (2013.01); *A61K 40/11* (2025.01); *A61K 40/31* (2025.01); *A61K 40/4245* (2025.01); *A61K 40/4268* (2025.01); *A61K 40/4269* (2025.01); *C07K 14/70517* (2013.01); *C07K 14/70521* (2013.01); *C07K 14/70578* (2013.01); *C12N 5/0638* (2013.01); *A61K 38/00* (2013.01); *A61K 2239/31* (2023.05); *A61K 2239/38* (2023.05); *A61K 2239/57* (2023.05); *C07K 2319/03* (2013.01); *C07K 2319/30* (2013.01)

(58) Field of Classification Search
CPC .................................................. A61K 35/17
See application file for complete search history.

(56) References Cited

U.S. PATENT DOCUMENTS

| | | | |
|---|---|---|---|
| 10,667,501 B2 | 6/2020 | Germaschewski et al. | |
| 10,888,608 B2 | 1/2021 | Spencer et al. | |
| 11,826,386 B2 | 11/2023 | DiLillo et al. | |
| 11,932,690 B2 * | 3/2024 | Sadelain | C07K 16/00 |
| 2017/0137515 A1 * | 5/2017 | Chang | A61K 39/001186 |
| 2018/0171024 A1 * | 6/2018 | Peled Kamar | C07K 16/30 |
| 2019/0309042 A1 | 10/2019 | Maurer et al. | |
| 2020/0077644 A1 * | 3/2020 | Church | A01N 1/02 |
| 2022/0031748 A1 | 2/2022 | DiLillo et al. | |

FOREIGN PATENT DOCUMENTS

| | | |
|---|---|---|
| EP | 3636761 A1 | 4/2020 |
| WO | WO-2016/199141 A2 | 12/2016 |
| WO | WO-2017/027291 A1 | 2/2017 |
| WO | WO-2018/075813 A1 | 4/2018 |
| WO | WO-2020/227446 A1 | 11/2020 |
| WO | WO-2021/016585 A1 | 1/2021 |
| WO | WO-2021/226063 A1 | 11/2021 |

OTHER PUBLICATIONS

Kowolik et al. CD28 Costimulation Provided through a CD19-Specific Chimeric Antigen Receptor Enhances In vivo Persistence and Antitumor Efficacy of Adoptively Transferred T Cells. Cancer Research 2006, 66;22:10995-11004. (Year: 2006).*
Brentjens et al. Genetically Targeted T Cells Eradicate Systemic Acute Lymphoblastic Leukemia Xenografts. Clinical Cancer Research 2007, 13;18:5426-5435. (Year: 2007).*
International Search Report and Written Opinion for International Application No. PCT/US2021/030625 mailed Aug. 31, 2021.
Mukherjee, "Abstract 138: A Quantitative Imaging Toolbox to Evaluate the Effects of Endomains on CAR Immune Synapse," Mol Ther, 25(551): 1-363 (2017).
Qasim et al., "First application of Talen engineered universal CAR-T cells in B-ALL," Blood 126(23) (2015).
Tassev et al., "Retargeting NK92 cells using an HLA-A2-restricted, EBNA3C-specific chimeric antigen receptor," Cancer Gene Therapy 19: pp. 84-100 (2012).
Walseng et al., "A TCR-based chimeric antigen receptor," Scientific Reports 7 (2017).
Zhong et al., "Chimeric antigen receptors combining 4-1BB and CD28 signaling domains augment PI3 kinase/AKT/Bcl-XI activation and CD8+ T cell-mediated tumor eradication," Molecular Therapy 18(2): pp. 413-420 (2010).

* cited by examiner

Primary Examiner — Christopher M Babic
Assistant Examiner — Jennifer S Spence
(74) Attorney, Agent, or Firm — Foley Hoag LLP; Brendan T. Jones; Konstantinos Mylonas

(57) ABSTRACT

Disclosed are compositions and methods for targeted treatment of cancer. The present disclosure provides chimeric antigen receptors and cells expressing such chimeric antigen receptors. In certain embodiments, engineered cells expressing the chimeric antigen receptors are specific for a low density cancer antigen or peptide in groove antigen.

15 Claims, 18 Drawing Sheets
Specification includes a Sequence Listing.

Day 0-21 tumor curves

Day 0-37 tumor curves

FIG. 5F
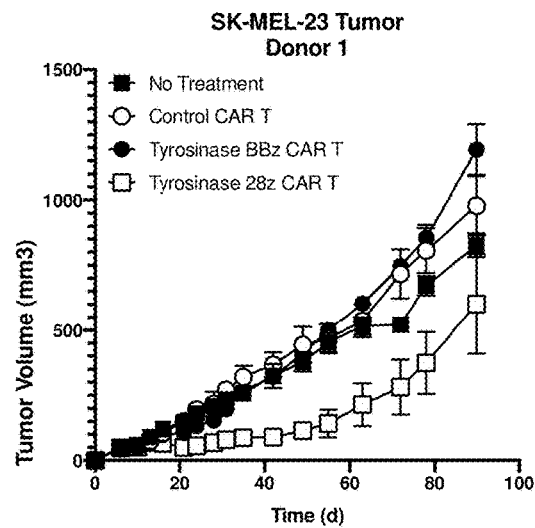
FIG. 5G
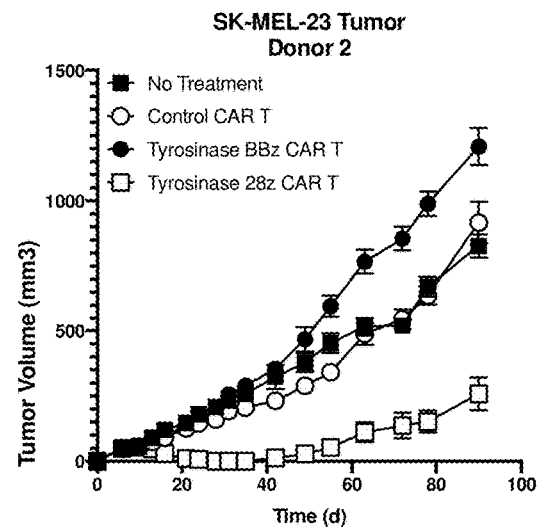
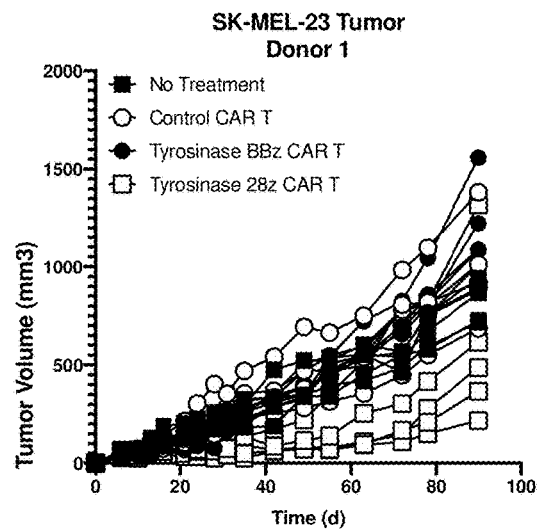
FIG. 5H
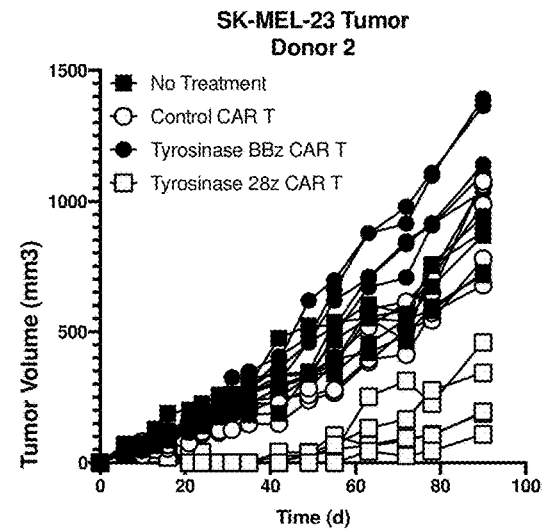
FIG. 5I

Day 0-21 tumor curves

Day 0-38 tumor curves

COMPOSITIONS AND METHODS FOR TREATING CANCER

RELATED APPLICATIONS

This application is a Continuation of Application of Ser. No. 17/307,235, filed on May 4, 2021, which claims priority to U.S. Provisional Application No. 63/020,177, filed May 5, 2020, each of which is hereby incorporated herein by reference in its entirety.

SEQUENCE LISTING

This application contains a Sequence Listing which has been submitted electronically in XML format. The Sequence Listing XML is incorporated herein by reference. Said XML file, created on Feb. 8, 2024, is named RPB-02102_SL.xml and is 53,619 bytes in size.

BACKGROUND

Cancer is the second leading cause of death in the United States. Current therapies for many cancers either fail in certain patient populations or generate toxic side-effects which greatly impact the quality of life of the patient. Adoptive immunotherapy, which involves the transfer of antigen-specific T cells generated ex vivo, is a promising strategy to treat cancer. T cells used for adoptive immunotherapy can be generated, for example, by redirection of T cells through genetic engineering (e.g., by engineering them to express chimeric antigen receptors, or "CARs"). However, current adoptive immunotherapy approaches are often ineffective at targeting antigens that are expressed at low density, such as peptide antigens that are presented by MHC class I proteins (referred to as "peptide in groove," or "PIG" antigens). The targeting of PIG antigens using adoptive immunotherapy is particularly attractive for a number of reasons, including because it allows for the use of CAR polypeptide expressing T cells (CAR T cells) that target intracellular cancer associated antigens. Thus, there is a need in the art for improved adoptive immunotherapy approaches that facilitate the targeting of low density antigens, including PIG antigens, for the treatment of cancer.

SUMMARY

The present application is based, at least in part, on the discovery that CAR T cells that express a CAR comprising a CD28/z signaling domain demonstrate superior in vitro and in vivo efficacy when targeting peptide in groove (PIG) antigens or low density cancer antigens. In some aspects, provided herein are CAR polypeptides targeting PIG antigens or low density cancer antigens that comprise a CD28/z signaling domain and nucleic acids encoding such CAR polypeptides, as well as methods of using and making such CAR polypeptides and nucleic acids.

In some aspects, provided herein are CAR polypeptides comprising at least one intracytoplasmic/costimulatory region comprising a cluster of differentiation 28 zeta (CD28/ζ) domain. In some embodiments, the CAR polypeptide further comprises at least one intracytoplasmic signaling region comprising a cluster of differentiation 3 zeta (CD3/ζ) domain. In some embodiments, the CAR polypeptide further comprises an antigen binding domain specific for a low density cancer and/or a peptide in groove antigen.

In some embodiments, the intracytoplasmic/costimulatory region of the CAR polypeptide further comprises a 4-1BB domain (e.g., in addition to the cluster of differentiation 28 zeta (CD28/ζ) domain). The CAR polypeptide may comprise a hinge/spacer region that comprises at least one cluster of differentiation 28 zeta (CD28/ζ) domain. The CAR polypeptide may comprise a transmembrane region that comprises at least one cluster of differentiation 28 zeta (CD28/ζ) domain.

In some embodiments, the CAR polypeptides disclosed herein has antigenic specificity for a cancer antigen, wherein the CAR comprises at least one cluster of differentiation 28 zeta (CD28/ζ) amino acid sequence selected from the amino acid sequences set forth in SEQ ID NOs. 1 to 3. The CD28/ζ sequence may be in the hinge, transmembrane, or signaling domain of the CAR. Also provided herein are CAR polypeptides having antigenic specificity for a cancer antigen and the CAR comprises an amino acid sequence set forth in SEQ ID NO:s. 6 to 13, 29, 30, 33 or 34.

The CAR polypeptide may comprise at least one cluster of differentiation 28 (CD28) amino acid sequence that is part of the intracytoplasmic/costimulatory region of the CAR. The CAR polypeptide may have at least one cluster of differentiation 28 (CD28) amino acid sequence that is part of the transmembrane region of the CAR. The CAR polypeptide may comprise at least one cluster of differentiation 28 (CD28) amino acid sequence is part of the hinge/spacer region of the CAR.

As disclosed herein, the cancer antigen may be a peptide in groove antigen and/or a low density cancer antigen. Less than two thousand copies, less than one thousand copies, or less than five hundred copies of the cancer antigen may be typically found in a tumor (e.g., a solid tumor). The cancer antigen may be a MAGEA4, Tyrosinase, HPV16 E7, or a NY-ESO peptide. The cancer antigen may comprise at least one epitope selected from $MAGEA4_{230-239}$, $MAGEA4_{286-294}$, $Tyr_{369-377}$, $HPV16E7_{11-19}$ or $NY\text{-}ESO\text{-}1_{157-165}$.

The CAR polypeptide may comprise a variable light chain comprising any one of the amino acid sequences set forth in SEQ ID NO: 16 to 19, 31, or 37. The CAR polypeptide may comprise a variable heavy chain comprising any one of the amino acid sequences set forth in SEQ ID NO: 20 to 23, 32, or 38.

In some aspects, provided herein nucleic acids encoding the CAR polypeptides disclosed herein. The nucleic acid may be an expression vector (e.g., a viral vector, such as a lentiviral vector). The nucleic acid encoding the CAR polypeptide may have a sequence set forth in SEQ ID NOs: 14, 15, 35 or 36.

Also provided herein are immune cells comprising a CAR polypeptide disclosed herein or a nucleic acid encoding a CAR polypeptide disclosed herein. Also provided herein are compositions comprising immune cells disclosed herein, and cell banks comprising such immune cells. Cell banks may be cell banks for adoptive immunotherapy. The immune cell may be a leukocyte, lymphocyte, a monocyte, a macrophage, a dendritic cell, a mast cell, a neutrophil, a basophil, or an eosinophil. In some embodiments, the immune cell is a lymphocyte selected from an αβT cell, γδT cell, a Natural Killer (NK) cell, a Natural Killer T (NKT) cell, an innate lymphoid cell (ILC), a cytokine induced killer (CIK) cell, a cytotoxic T lymphocyte (CTL), a lymphokine activated killer (LAK) cell, a regulatory T cell, or any combination thereof.

In some aspects, provided herein are methods of treating cancer (e.g., a solid tumor) in a subject by administering to the subject a composition comprising cells expressing a CAR polypeptide disclosed herein (e.g., a CAR polypeptide comprising at least one intracytoplasmic/costimulatory region comprising a cluster of differentiation 28 zeta (CD28/ ζ) domain. In some embodiments, the CAR polypeptide further comprises at least one intracytoplasmic signaling region comprising a cluster of differentiation 3 zeta (CD3/ζ) domain. In some embodiments, the CAR polypeptide further comprises an antigen binding domain specific for a low density cancer and/or a peptide in groove antigen.

In some embodiments, the methods provided herein further comprise conjointly administering to the subject a second CAR polypeptide comprising a 4-1BB domain in the costimulatory region of the CAR polypeptide. In some embodiments, the second CAR comprises at least one intracytoplasmic signaling region comprising a cluster of differentiation 3 zeta (CD3/ζ) domain. In some embodiments, the second CAR comprises an extracellular domain specific for a low density cancer antigen and/or a peptide in groove cancer antigen. The second CAR polypeptide may comprise a cluster of differentiation 8 alpha (CD8/α) peptide in the hinge/transmembrane region.

In some embodiments, the subject may have cancer. The cancer may be melanoma.

BRIEF DESCRIPTION OF THE DRAWINGS

FIG. 1B shows chimeric antigen receptors containing an anti-HLA-A2/MAGEA4$_{286-294}$ 31345 scFv plus either (top) a huCD8 hinge/transmembrane domain, a 4-1BB co-stimulatory domain, and a CD3z signaling domain (BB/z CAR), or (middle) huCD28 hinge/transmembrane/costimulatory domains and a CD3z signaling domain (28/z CAR) An irrelevant scFv plus a huCD8 hinge/transmembrane domain, a 4-1BB co-stimulatory domain and a CD3z signaling domain served as a control CAR (bottom).

FIGS. 2A and 2C: values represent mean±SEM tumor volumes on the indicated day after tumor implantation. FIGS. 2B and 2D show tumor growth curves from individual mice.

FIGS. 3A and 3C: values represent mean±SEM tumor volumes on the indicated day after tumor implantation. FIGS. 3B and 3D show tumor growth curves from individual mice.

FIGS. 4A-4D show data from NSG mice that were subcutaneously injected with HLA-A2$^+$MAGEA4$^+$ A375 human melanoma tumor cells. On day 13 after tumors were established, the mice (n=4 or 5 per group) were intravenously injected with 4×10$^6$ T cells that express either the non-binding control BB/z CAR (Control CAR T), the anti-HLA-A2/MAGEA4$_{230-239}$ BB/z CAR, or the anti-HLA-A2/MAGEA4$_{230-239}$ 28/z CAR. Tumor growth was assessed through day 37 by measuring tumor volumes. FIGS. 4A and 4B show tumor growth between days 0-21. FIGS. 4C and 4D show tumor growth curved between days 0-37. FIGS. 4A and 4C: values represent mean±SEM tumor volumes on the indicated day after tumor implantation. FIGS. 4B and 4D show tumor growth curves from individual mice.

FIGS. 5A-5I show exemplary CAR constructs used in Example 4 and measurement of xenogenic tumors in mice treated with exemplary CAR-T cells. The result demonstrate that anti-Tyrosinase$_{369-377}$ 28/z CAR T cells demonstrate superior in vivo anti-tumor activity and anti-tumor kinetics compared to Tyrosinase$_{369-377}$ BB/z CAR T cells in the WM266.4 and SK-MEL-23 melanoma tumor models. FIG. 5A shows chimeric antigen receptors containing an anti-HLA-A2/Tyrosinase$_{369-377}$ D11 scFv plus either (top) a huCD8 hinge/transmembrane domain, a 4-1BB co-stimulatory domain, and a CD3z signaling domain (BB/z CAR), or (middle) huCD28 hinge/transmembrane/costimulatory domains and a CD3z signaling domain (28/z CAR). (Bottom) An irrelevant scFv plus a huCD8 hinge/transmembrane domain, a 4-1BB co-stimulatory domain and a CD3z signaling domain served as a control CAR. FIGS. 5B-5E show data from NSG mice that were subcutaneously injected with 4×10$^6$ HLA-A2$^+$Tyrosinase$^+$ WM266.4 human melanoma tumor cells. On day 7 after tumors were established, the mice (n=5 per group) were intravenously injected with 2×10$^6$ T cells that express either the non-binding control BB/z CAR (Control CAR T), the anti-HLA-A2/Tyrosinase$_{369-377}$ BB/z CAR, or the anti-HLA-A2/Tyrosinase$_{369-377}$ 28/z CAR from two different donors. Tumor growth was assessed through day 90 by measuring tumor volumes. FIGS. 5F-5I show data from NSG mice that were subcutaneously injected with 5×10$^6$ HLA-A2$^+$Tyrosinase$^+$ SK-MEL-23 human melanoma tumor cells. On day 7 after tumors were established, the mice (n=5 per group) were intravenously injected with 4×10$^6$ T cells that express either the non-binding control BB/z CAR (Control CAR T), the anti-HLA-A2/Tyrosinase$_{369-377}$ BB/z CAR, or the anti-HLA-A2/Tyrosinase$_{369-377}$ 28/z CAR from two different donors. Tumor growth was assessed through day 90 by measuring tumor volumes. Data shown from (FIGS. 5B, 5D, 5F, and 5H) Donor 1 and (FIGS. 5C, 5E, 5G, and 5I) Donor 2. FIGS. 5B, 5C, 5F, and 5G: values represent mean±SEM tumor volumes on the indicated day after tumor implantation. FIGS. 5D, 5E, 5H, and 5I show tumor growth curves from individual mice.

FIG. 6A shows chimeric antigen receptors containing an anti-HLA-A2/NY-ESO-1$_{157-165}$ 28105P scFv plus either (top) a huCD8 hinge/transmembrane domain, a 4-1BB co-stimulatory domain, and a CD3z signaling domain (BB/z CAR), or (middle) huCD28 hinge/transmembrane/costimulatory domains and a CD3z signaling domain (28/z CAR). (Bottom) An irrelevant scFv plus a huCD8 hinge/transmembrane domain, a 4-1BB co-stimulatory domain and a CD3z signaling domain served as a control CAR. FIGS. 6B-6E show NSG mice were subcutaneously injected with 5×10$^6$ HLA-A2$^+$NY-ESO-1$^+$ A375 human melanoma tumor cells. On day 3 after tumors were established, the mice (n=5 per group) were intravenously injected with 20×10$^6$ T cells that express either the non-binding control BB/z CAR (Control CAR T), the anti-HLA-A2/NY-ESO-1$_{157-165}$ BB/z CAR, or the anti-HLA-A2/NY-ESO-1$_{157-165}$ 28/z CAR. Tumor growth was assessed through day 38 by measuring tumor volumes. FIGS. 6B and 6C show tumor growth between days 0-21. FIGS. 6D and 6E show tumor growth curved between days 0-38. FIGS. 6B and 6D: values represent mean±SEM tumor volumes on the indicated day after tumor implantation. FIGS. 6C and 6E show tumor growth curves from individual mice.

DETAILED DESCRIPTION

General

Figure 1A:
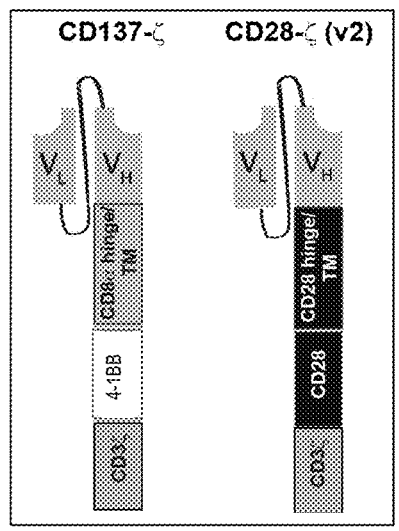
FIGS. 1A and 1B show general CAR construct designs and exemplary CAR constructs used in Examples 1 and 2. General BB/z and 28/z CAR construct schematics in FIG. 1A.

In some aspects, provided herein are CAR polypeptides and polynucleotides encoding said CAR polypeptides comprising at least one intracytoplasmic/costimulatory region comprising a cluster of differentiation 28 zeta (CD28/ζ) domain. The CD28/ζ domain may be a human CD28/ζ domain. In some embodiments, the CAR polypeptide further comprises at least one intracytoplasmic signaling region comprising a cluster of differentiation 3 zeta (CD3/ζ) domain. The CAR polypeptide may also comprise an antigen binding domain specific for a low density cancer antigen and/or a peptide in groove antigen. Also provided herein are immune cells expressing a CAR polypeptide disclosed herein, as well as cell banks comprising immune cells expressing a CAR polypeptide disclosed herein.

As disclosed herein, cancers characterized by PIG antigens or low density cancer antigens escape conventional cancer therapies because they are often present in low target copy numbers within tumors. Additionally, solid tumors characterized by PIGs or low density cancer antigens can be more resistant to CAR-T therapy and more difficult to treat because they are not cell surface antigens, but are present in grooves within the cancer related peptide. Thus, there is a need for the improved CAR therapies provided herein that can effectively target PIGs and/or low density cancer antigens to increase/enhance efficacy of CAR therapy in cancers, especially those cancers characterized by solid tumors.

Methods disclosed herein include methods of treating a tumor in a subject by administering a composition comprising cells expressing a CAR polypeptide disclosed herein.

In some embodiments, the CAR polypeptides disclosed herein have a specificity for a low density cancer antigen or a PIG antigen. A low density cancer antigen includes, but is not limited to, any cancer antigen wherein less than five thousand, less than four thousand, less than three thousand, less than two thousand, less than fifteen hundred, less than one thousand, less than nine hundred, less than eight hundred, less than seven hundred, less than six hundred, less than five hundred, less than four hundred, less than three hundred, less than two hundred, or less than one hundred copies of the cancer antigen are typically found in a solid tumor. The cancer antigen may be a MAGEA4, Tyrosinase, HPV16 E7, or a NY-ESO peptide. The cancer antigen may comprise an epitope selected from MAGEA4$_{230-239}$, MAGEA4$_{286-294}$, Tyr$_{369-377}$, HPV16E7$_{11-19}$, or NY-ESO-1$_{157-165}$. For example, the CAR may comprise an antigen-binding domain using the variable light chain and/or heavy chains, or portion thereof, of an antibody specific for a low density or PIG antigen, such as an epitope sequence in a MAGEA4, Tyrosinase, HPV16 E7, or a NY-ESO peptide.

Definitions

For convenience, certain terms employed in the specification, examples, and appended claims are collected here.

The articles "a" and "an" are used herein to refer to one or more than one (i.e., to at least one) of the grammatical object of the article. By way of example, "an element" means one element or more than one element.

As used herein, the term "administering" means providing a pharmaceutical agent or composition to a subject, and includes, but is not limited to, administering by a medical professional and self-administering. Such an agent can contain, for example, a CAR T cell provided herein.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of the foregoing.

The term "binding" or "interacting" refers to an association, which may be a stable association, between two molecules, e.g., between a peptide and a binding partner or agent, e.g., small molecule, due to, for example, electrostatic, hydrophobic, ionic and/or hydrogen-bond interactions under physiological conditions.

As used herein, the term "cancer" includes, but is not limited to, solid tumors and blood borne tumors. The term cancer includes, but is not limited to, diseases of the skin, tissues, organs, bone, cartilage, blood, and vessels, including the cervix, anus, vagina, vulva, penis, tongue base, larynx, and tonsil. The term "cancer" further encompasses primary and metastatic cancers.

The term "chimeric antigen receptor" (CAR) refers to molecules that combine a binding domain against a component present on the target cell, for example an antibody-based specificity for a desired antigen (e.g., a tumor antigen) with a T cell receptor-activating intracellular domain to generate a chimeric protein that exhibits a specific anti-target cellular immune activity. Generally, CARs consist of an extracellular single chain antigen-binding domain (scFv) fused to the intracellular signaling domain of the T cell antigen receptor complex zeta chain, and have the ability, when expressed in T cells, to redirect antigen recognition based on the monoclonal antibody's specificity.

A "costimulatory domain" or "costimulatory molecule" refers to the cognate binding partner on a T-cell that specifically binds with a costimulatory ligand, thereby mediating a costimulatory response by the cell, such as, but not limited to proliferation. The costimulatory domain may be a human costimulatory domain. Exemplary costimulatory molecules include, CD28, 4-1BB, CD27, CD8, 4-1BB (CD137), OX40, CD30, CD40, PD-1, ICOS, lymphocyte function-associated antigen-1 (LFA-1), CD2, CD7, LIGHT, NKG2C, and B7-H3.

A "costimulatory ligand" refers to a molecule on an antigen presenting cell that specifically binds a cognate costimulatory molecule on a T-cell, thereby providing a signal which mediates a T cell response, including, but not limited to, proliferation activation, differentiation and the like. A costimulatory ligand can include but is not limited to CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3.

A "costimulatory signal" refers to a signal, which in combination with a primary signal, leads to T cell proliferation and/or upregulation or downregulation of key molecules.

The term "epitope" means a protein determinant capable of specific binding to an antibody or immune cell (e.g., T cell). Epitopes usually consist of chemically active surface groupings of molecules such as amino acids or sugar side chains. Certain epitopes can be defined by a particular sequence of amino acids to which a CAR or antibody is capable of binding.

"Gene construct" refers to a nucleic acid, such as a vector, plasmid, viral genome or the like which includes a "coding sequence" for a polypeptide or which can otherwise transcribe to a biologically active RNA (e.g., antisense, decoy, ribozyme, etc.), may be transfected into cells, e.g., mammalian cells, and may cause expression of the coding sequence in cells transfected with the construct. The gene construct may include one or more regulatory elements operably linked to the coding sequence, as well as intronic sequences, polyadenylation sites, origins of replication, marker genes, etc.

The terms "ligand-binding domain" and "antigen-binding domain" are used interchangeably herein, and refer to that portion of a chimeric antigen receptor that binds specifically to a predetermined antigen.

The term "linker" is art-recognized and refers to a molecule or group of molecules connecting two compounds, such as two polypeptides. The linker may be comprised of a single linking molecule or may comprise a linking molecule and a spacer molecule, intended to separate the linking molecule and a compound by a specific distance.

The term "operably linked to" refers to the functional relationship of a nucleic acid with another nucleic acid sequence. Promoters, enhancers, transcriptional and translational stop sites, and other signal sequences are examples of nucleic acid sequences operably linked to other sequences. For example, operable linkage of DNA to a transcriptional control element refers to the physical and functional relationship between the DNA and promoter such that the transcription of such DNA is initiated from the promoter by an RNA polymerase that specifically recognizes, binds to and transcribes the DNA.

As used herein, the phrase "pharmaceutically acceptable" refers to those agents, compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the phrase "pharmaceutically-acceptable carrier" means a pharmaceutically-acceptable material, composition or vehicle, such as a liquid or solid filler, diluent, excipient, or solvent encapsulating material, involved in carrying or transporting an agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

The terms "polynucleotide", and "nucleic acid" are used interchangeably. They refer to a natural or synthetic molecule, or some combination thereof, comprising a single nucleotide or two or more nucleotides linked by a phosphate group at the 3' position of one nucleotide to the 5' end of another nucleotide. The polymeric form of nucleotides is not limited by length and can comprise either deoxyribonucleotides or ribonucleotides, or analogs thereof. Polynucleotides may have any three-dimensional structure, and may perform any function. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. A polynucleotide may be further modified, such as by conjugation with a labeling component. In all nucleic acid sequences provided herein, U nucleotides are interchangeable with T nucleotides. The polynucleotide is not necessarily associated with the cell in which the nucleic acid is found in nature, and/or operably linked to a polynucleotide to which it is linked in nature.

The term "precancerous lesions" or "precancerous condition" refers to atypical cells and/or tissues that are associated with an increased risk of cancer. The term "precancerous lesions" may refer, for example, to dysplasia, benign neoplasia, or carcinoma in situ.

As used herein, a therapeutic that "prevents" a condition refers to a compound that, when administered to a statistical sample prior to the onset of the disorder or condition, reduces the occurrence of the disorder or condition in the treated sample relative to an untreated control sample, or delays the onset or reduces the severity of one or more symptoms of the disorder or condition relative to the untreated control sample.

A "signal transducing domain" or "signaling domain" of a CAR, as used herein, is responsible for intracellular signaling following the binding of an extracellular ligand binding domain to the target resulting in the activation of the immune cell and immune response. In other words, the signal transducing domain is responsible for the activation of at least one of the normal effector functions of the immune cell in which the CAR is expressed. For example, the effector function of a T cell can be a cytolytic activity or helper activity including the secretion of cytokines. Thus, the term "signal transducing domain" refers to the portion of a protein which transduces the effector function signal and directs the cell to perform a specialized function. Examples of signal transducing domains for use in a CAR can be the cytoplasmic sequences of the T cell receptor and co-receptors that act in concert to initiate signal transduction following antigen receptor engagement, as well as any derivate or variant of these sequences and any synthetic sequence that has the same functional capability. In some cases, signaling domains comprise two distinct classes of cytoplasmic signaling sequences, those that initiate antigen-dependent primary activation, and those that act in an antigen-independent manner to provide a secondary or co-stimulatory signal. Primary cytoplasmic signaling sequences can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Exemplary ITAMs include those derived from TCRζ, FcRγ, FcRβ, FcRε, CD3γ, CD3δ, CD3ε, CD5, CD22, CD79a, CD79b and CD66d.

A "spacer" as used herein refers to a peptide that joins the proteins (e.g., those in a fusion protein). Generally, a spacer has no specific biological activity other than to join the proteins or to preserve some minimum distance or other spatial relationship between them. However, the constituent amino acids of a spacer may be selected to influence some property of the molecule such as the folding, net charge, or hydrophobicity of the molecule.

The term "specifically binds" or "specific binding", as used herein, when referring to a polypeptide (including CAR polypeptides) refers to a binding reaction which is determinative of the presence of the protein or polypeptide or receptor in a heterogeneous population of proteins and other biologics. Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ M$^{-1}$ (e.g., $10^6$ M$^{-1}$, $10^7$ M$^{-1}$, $10^8$ M$^{-1}$, $10^9$ M$^{-1}$, $10^{10}$ M$^{-1}$, $10^{11}$ M$^{-1}$, and $10^{12}$ M$^{-1}$ or more) with that second molecule. For example, in the case of the ability of a PIG-specific CAR to bind to a peptide presented on an MHC (e.g., class I MHC or class II MHC); typically, a CAR specifically binds to its peptide/MHC with an affinity of at least a KD of about 10-4 M or less, and binds to the predetermined antigen/binding partner with an affinity (as expressed by KD) that is at least 10 fold less, at least 100 fold less or at least 1000 fold less than its affinity for binding to a non-specific and unrelated peptide/MHC complex (e.g., one comprising a BSA peptide or a casein peptide).

As used herein, the term "subject" means a human or non-human animal selected for treatment or therapy.

The terms "transformation", "transfection", or "transduction" mean the introduction of a nucleic acid, e.g., an expression vector, into a recipient cell (e.g., a mammalian cell) including introduction of a nucleic acid to the chromosomal DNA of said cell.

As used herein, the term "treatment" refers to clinical intervention designed to alter the natural course of the individual being treated during the course of clinical pathology. Desirable effects of treatment include decreasing the rate of progression, ameliorating or palliating the pathological state, and remission or improved prognosis of a particular disease, disorder, or condition. An individual is successfully "treated," for example, if one or more symptoms associated with a particular disease, disorder, or condition are mitigated or eliminated.

The term "variant" refers to an amino acid or peptide sequence having conservative amino acid substitutions, non-conservative amino acid substitutions (e.g., a degenerate variant), substitutions within the wobble position of each codon (e.g., DNA and RNA) encoding an amino acid, amino acids added to the C-terminus of a peptide, or a peptide having 60%, 70%, 80%, 90%, 95%, 96%, 97%, 98%, 99% sequence identity to a reference sequence.

The term "vector" refers to the means by which a nucleic acid can be propagated and/or transferred between organisms, cells, or cellular components. Vectors include plasmids, viruses, bacteriophage, pro-viruses, phagemids, transposons, and artificial chromosomes, and the like, to which the nucleic acid has been linked, and may or may not be able to replicate autonomously or integrate into a chromosome of a host cell. Such vectors may include any vector, (e.g., a plasmid, cosmid or phage chromosome) containing a gene construct in a form suitable for expression by a cell (e.g., linked to a transcriptional control element).

In certain embodiments, agents may be used alone or conjointly administered with another type of therapeutic agent. As used herein, the phrase "conjoint administration" or "administered conjointly" refers to any form of administration of two or more different therapeutic agents such that the second agent is administered while the previously administered therapeutic agent is still effective in the body (e.g., the two agents are simultaneously effective in the subject, which may include synergistic effects of the two agents). For example, the different therapeutic agents can be administered either in the same formulation or in separate formulations, either concomitantly or sequentially. In certain embodiments, the different therapeutic agents can be administered within about one hour, about 12 hours, about 24 hours, about 36 hours, about 48 hours, about 72 hours, or about a week of one another. Thus, a subject who receives such treatment can benefit from a combined effect of different therapeutic agents.

Chimeric Antigen Receptors (CARs)

Novel specificities in T cells have been successfully generated through the genetic transfer of transgenic T cell receptors or chimeric antigen receptors (CARs). CARs are receptors comprising a targeting moiety that is associated with one or more signaling domains and/or costimulatory domains in a single fusion molecule. In certain embodiments, the binding moiety of a CAR comprises an antigen-binding domain of a single-chain antibody (scFv), comprising the light and heavy chain variable fragments of a monoclonal antibody joined by a flexible linker. In certain embodiments, the binding moiety further comprises transmembrane and hinge domains of a monoclonal antibody.

In certain aspects, the CAR polypeptides provided herein comprise at least one intracytoplasmic/costimulatory region comprising a cluster of differentiation 28 zeta (CD28/ζ) domain. Additionally, the hinge/spacer region and/or the transmembrane region of the CAR or the transmembrane region of the CAR may comprise a CD28/domain. The CAR may comprise at least one cluster of differentiation 28 zeta (CD28/ζ) amino acid sequence selected from the amino acid sequences set forth in SEQ ID NOs: 1 to 3. A CAR polypeptide disclosed herein may comprise at least one cluster of differentiation 28 zeta (CD28/ζ) amino acid sequence with at least 50%, at least 60%, at least 70%, at least 80%, at least 90%, at least 91%, at least 92%, at least 93%, at least 94%, at least 95%, at least 96%, at least 97%, at least 98%, or at least 99% homology to an amino acid sequence set forth in SEQ ID NOs. 1 to 3. The CAR polypeptide may comprise all three sequence set for in SEQ ID NOs 1 to 3. For example, the CAR hinge domain may comprise SEQ ID NO: 1, the transmembrane domain may comprise SEQ ID NO: 2, and the co-stimulatory domain may comprise SEQ ID NO: 3.

TABLE 1

Exemplary CD28/ζ Sequences.

| SEQ ID NO: | Domain | Sequence |
|---|---|---|
| 1 | Hinge | IEVMYPPPYLDNEKSNGTIIHVKGKHLCPSPLFPGPSKP |
| 2 | Transmembrane | FWVLVVVGGVLACYSLLVTVAFIIFWV |
| 3 | Co-Stimulatory | RSKRSRLLHSDYMNMTPRRPGPTRKHYQPYAPPRDFAAYRS |

In some embodiments, the CAR comprises an antigen binding domain specific for a low density cancer antigen and/or a peptide in groove antigen. Exemplary PIG antigens and low density cancer antigens can be found in Table 1. In some embodiments, the CAR polypeptides disclosed herein specifically bind an epitope listed in Table 2. In some embodiments, the present disclosure provides a Melanoma-Associated Antigen A4 (MAGE-A4)-specific chimeric antigen receptor (CAR), wherein said MAGE-A4-specific chimeric antigen receptor interacts with amino acids 286-294, or a portion thereof, of SEQ ID NO: 4. The polypeptide sequence of MAGE-A4 (286-294) is given as SEQ ID NO: 5.

SEQ ID NO: 4  MSSEQKSQHCKPEEGVEAQEEALGLVGAQAPTTEEQ
EAAVSSSSPLVPGTLEEVPAAESAGPPQSPQGASAL
PTTISFTCWRQPNEGSSSQEEEGPSTSPDAESLFRE
ALSNKVDELAHFLLRKYRAKELVTKAEMLERVIKNY
KRCFPVIFGKASESLKMIFGIDVKEVDPASNTYTLV
TCLGLSYDGLLGNNQIFPKTGLLIIVLGTIAMEGDS
ASEEEIWEELGVMGVYDGREHTVYGEPRKLLTQDWV
QENYLEYRQVPGSNPARYEFLWGPRALAETSYVKVL
EHVVRVNARVRIAYPSLREAALLEEEEGV

SEQ ID NO:5  KVLEHVVRV

TABLE 2

Exemplary PIG cancer antigens.

| Antigenic peptide | Epitope | Estimated Number of Copies | HLA |
|---|---|---|---|
| Tyrosinase | Tyr$_{369-377}$ | 2000-4500 copies | HLA-A2 |
| MAGEA4 | MAGEA4$_{286-296}$ | 400-1000 copies | HLA-A2 |
| MAGEA4 | MAGEA4$_{230-239}$ | Approximately 500 copies | HLA-A2 |
| NY-ESO | NY-ESO$_{157-165}$ | 200-400 copies | HLA-A2 |
| HPV16 E7 | HPV16E7$_{11-19}$ | 50 copies | HLA-A2 |

Additionally exemplary PIG epitopes may be derived from melanoma-associated antigen 3 (MAGE-A3); melanoma-associated antigen 1 (MAGE-1); melanoma-associated antigen 10 (MAGEA10); melanoma antigen recognized by T cells 1 (MART-1), Epstein-Barr virus (EBV) latent membrane protein 2 (LMP2); mouse double-minute 2 (MDM2); melanoma-associated antigen 1 (MAGE-A1);

glycoprotein 100 (gp100); tumor protein p53 (P53); minor histocompatibility antigens (mHag); minor histocompatibility antigen HA-1 (HA-1); ubiquitously transcribed tetratricopeptide repeat gene on the Y chromosome (UTY); ribosomal protein S4, Y-linked (RPS4Y); the MHC class-II-restricted dead-box RNA helicase Y (DBY); cytotoxic T cell (CTL)-recognized antigen on melanoma (CAMEL); Wilms' tumor 1 (WT1); a renal cell carcinoma (RCC) tumor antigen; mouse mastocytoma P815; Leucine Zipper Protein 4 (LUZP4); cancer/testis-associated SPANX antigens; ATPase family AAA domain containing protein 2 (ATAD2); Rhox homeobox family member 2 (RHOXF2); Cancer/Testis Antigen 136; F-Box Protein 39 (FBXO39); TDRD4; WW domain-binding protein 2 N-terminal-like (WBP2NL) or carcinoembryonic antigen (CEA).

Also provided herein are CAR polypeptides comprising an amino acid sequence set forth in SEQ ID NOs. 6 to 13, 29, 30, 33, or 34. A CAR polypeptide disclosed herein may comprise at least 50%, at least 60%, at least 70%, at least 80%, at least 90%, at least 91%, at least 92%, at least 93%, at least 94%, at least 95%, at least 96%, at least 97%, at least 98%, or at least 99% homology to an amino acid sequence set forth in SEQ ID NOs. 6 to 13, 29, 30, 33, or 34.

TABLE 3

Exemplary CAR Polypeptides

| SEQ ID NO: | CAR ID | Sequence |
| --- | --- | --- |
| 6 | HPV 17363 VL-VH BBz | DIQMTQSPSSLSASVGDRVTITCRASQSISSYLNWYQQKPG KAPKLLIYAVSILQSGVPSRFSGSGSGTDFTLTINSLQPEDFA TYSCQQTYSTPPITFGQGTRLEIKGGGGSGGGGSGGGGSEV QLLESGGGLVQPGGSLRLSCAASGFTFSSYAMTWVRQAPG MGLEWVSVISGSGSETYYADSVKGRFTISRDNSKNTLYLQ MNSLRAEDTAVYYCVKDSSYRSSSRAYYYYGMDVWGLG TTVTVSSGGGGSTTTPAPRPPTPAPTIASQPLSLRPEACRPA AGGAVHTRGLDFACDIYIWAPLAGTCGVLLLSLVITLYCKR GRKKLLYIFKQPFMRPVQTTQEEDGCSCRFPEEEEGGCELR VKFSRSADAPAYQQGQNQLYNELNLGRREEYDVLDKRRG RDPEMGGKPRRKNPQEGLYNELQKDKMAEAYSEIGMKGE RRRGKGHDGLYQGLSTATKDTYDALHMQALPPR |
| 7 | HPV 17363 VL-VH CD28hingeTM cytoCD3z | DIQMTQSPSSLSASVGDRVTITCRASQSISSYLNWYQQKPG KAPKLLIYAVSILQSGVPSRFSGSGSGTDFTLTINSLQPEDFA TYSCQQTYSTPPITFGQGTRLEIKGGGGSGGGGSGGGGSEV QLLESGGGLVQPGGSLRLSCAASGFTFSSYAMTWVRQAPG MGLEWVSVISGSGSETYYADSVKGRFTISRDNSKNTLYLQ MNSLRAEDTAVYYCVKDSSYRSSSRAYYYYGMDVWGLG TTVTVSSGGGGSIEVMYPPPYLDNEKSNGTIIHVKGKHLCP SPLFPGPSKPFWVLVVVGGVLACYSLLVTVAFIIFWVRSKR SRLLHSDYMNMTPRRPGPTRKHYQPYAPPRDFAAYRSRVK FSRSADAPAYQQGQNQLYNELNLGRREEYDVLDKRRGRD PEMGGKPRRKNPQEGLYNELQKDKMAEAYSEIGMKGERR RGKGHDGLYQGLSTATKDTYDALHMQALPPR |
| 8 | MAGEA4 (286-294) 31345 VL-VH BBz CAR | DIQMTQSPSSLSASVGDRVTITCRASQSISSYLNWYQQKPG KAPKLLIYAASSLQSGVPSRFSGSGSGTDFTLTISSLQPEDFA TYYCQQSYSTPPITFGQGTRLEIKRGGGGSGGGGSGGGGSQ VQLVESGGGLVKPGGSLRLSCAASGFTFSEYYMTWIRQAP GQGLEWVSYISSSGFNIYYADSVKGRFTISRDNAKNSLFLQ MNSLRVEDTAVYYCAREGVTDGMDVWGQGTTVTVSSGG GGSTTTPAPRPPTPAPTIASQPLSLRPEACRPAAGGAVHTRG LDFACDIYIWAPLAGTCGVLLLSLVITLYCKRGRKKLLYIFK QPFMRPVQTTQEEDGCSCRFPEEEEGGCELRVKFSRSADAP AYQQGQNQLYNELNLGRREEYDVLDKRRGRDPEMGGKPR RKNPQEGLYNELQKDKMAEAYSEIGMKGERRRGKGHDGL YQGLSTATKDTYDALHMQALPPR |
| 9 | MAGEA4 (286-294) 31345 VL-VH CD28z hingeTMcyto CD3z CAR | DIQMTQSPSSLSASVGDRVTITCRASQSISSYLNWYQQKPG KAPKLLIYAASSLQSGVPSRFSGSGSGTDFTLTISSLQPEDFA TYYCQQSYSTPPITFGQGTRLEIKRGGGGSGGGGSGGGGSQ VQLVESGGGLVKPGGSLRLSCAASGFTFSEYYMTWIRQAP GQGLEWVSYISSSGFNIYYADSVKGRFTISRDNAKNSLFLQ MNSLRVEDTAVYYCAREGVTDGMDVWGQGTTVTVSSGG GGSIEVMYPPPYLDNEKSNGTIIHVKGKHLCPSPLFPGPSKP FWVLVVVGGVLACYSLLVTVAFIIFWVRSKRSRLLHSDYM NMTPRRPGPTRKHYQPYAPPRDFAAYRSRVKFSRSADAPA YQQGQNQLYNELNLGRREEYDVLDKRRGRDPEMGGKPRR KNPQEGLYNELQKDKMAEAYSEIGMKGERRRGKGHDGLY QGLSTATKDTYDALHMQALPPR |
| 10 | NY-ESO (157-165) 28105 VH-VL BBz CAR | EVQLVESGGGVVQPGGSLRLSCEASGFIFDDYAMHWVRQ APGKGLEWVSLISGDGDIIYYADSVKGRFTISRDNSKNSLY LQMNSLIIEDTALYYCAKDWVFGVVMTHYWYFGLDVWG QGTTVTVSSGGGGSGGGGSGGGGSDIQMTQSPSSLSASEG DRVTITCRASQSISTYLNWYQQKPGKAPKLLIYGASSLQSG VPSRFSGSGSGTDFTLTISSLQPEDFATYYCQQSYSTPPITFG QGTKVEIKGGGGSTTTPAPRPPTPAPTIASQPLSLRPEACRP |

TABLE 3-continued

Exemplary CAR Polypeptides

| SEQ ID NO: | CAR ID | Sequence |
|---|---|---|
| | | AAGGAVHTRGLDFACDIYIWAPLAGTCGVLLLSLVITLYCK RGRKKLLYIFKQPFMRPVQTTQEEDGCSCRFPEEEEGGCEL RVKFSRSADAPAYQQGQNQLYNELNLGRREEYDVLDKRR GRDPEMGGKPRRKNPQEGLYNELQKDKMAEAYSEIGMKG ERRRGKGHDGLYQGLSTATKDTYDALHMQALPPR |
| 11 | NY-ESO (157-165) 28105 VH-VL CD28z hingeTMcyto CD3z CAR | EVQLVESGGGVVQPGGSLRLSCEASGFIFDDYAMHWVRQ APGKGLEWVSLISGDGDIIYYADSVKGRFTISRDNSKNSLY LQMNSLIIEDTALYYCAKDWVFGVVMTHYWYFGLDVWG QGTTVTVSSGGGGSGGGGSGGGGSDIQMTQSPSSLSASEG DRVTITCRASQSISTYLNWYQQKPGKAPKLLIYGASSLQSG VPSRFSGSGSGTDFTLTISSLQPEDFATYYCQQSYSTPPITFG QGTKVEIKGGGGSIEVMYPPPYLDNEKSNGTIIHVKGKHLC PSPLFPGPSKPFWVLVVVGGVLACYSLLVTVAFIIFWVRSK RSRLLHSDYMNMTPRRPGPTRKHYQPYAPPRDFAAYRSRV KFSRSADAPAYQQGQNQLYNELNLGRREEYDVLDKRRGR DPEMGGKPRRKNPQEGLYNELQKDKMAEAYSEIGMKGER RRGKGHDGLYQGLSTATKDTYDALHMQALPPR |
| 12 | Tyrosinase D11 VL-VH BBz CAR | DIQMTQSPASLSVSVGETVTITCRASDIIYSNLAWYQQKQG KSPQLLVYAATNLAAGVPSRFSGSGSGTQYSLKINSLQSED FGTYYCQHFWGSSISFGSGTKLEIKGGGGSGGGGSGGGGS QVQLKESGPGLVAPSQSLSITCTVSGFSLTSYGVHWVRQPP GKGLEWLGVIWAGGTTNYNSALMSRLSISRDNSKSQVFLE MNSLQTDDTAIYYCARDGHFHFDFWGQGTTLTVSSGGGGS TTTPAPRPPTPAPTIASQPLSLRPEACRPAAGGAVHTRGLDF ACDIYIWAPLAGTCGVLLLSLVITLYCKRGRKKLLYIFKQPF MRPVQTTQEEDGCSCRFPEEEEGGCELRVKFSRSADAPAY QQGQNQLYNELNLGRREEYDVLDKRRGRDPEMGGKPRRK NPQEGLYNELQKDKMAEAYSEIGMKGERRRGKGHDGLYQ GLSTATKDTYDALHMQALPPR |
| 13 | Tyrosinase D11 VL-VH CD28 hinge TM cyto CD3z CAR | DIQMTQSPASLSVSVGETVTITCRASDIIYSNLAWYQQKQG KSPQLLVYAATNLAAGVPSRFSGSGSGTQYSLKINSLQSED FGTYYCQHFWGSSISFGSGTKLEIKGGGGSGGGGSGGGGS QVQLKESGPGLVAPSQSLSITCTVSGFSLTSYGVHWVRQPP GKGLEWLGVIWAGGTTNYNSALMSRLSISRDNSKSQVFLE MNSLQTDDTAIYYCARDGHFHFDFWGQGTTLTVSSGGGGS IEVMYPPPYLDNEKSNGTIIHVKGKHLCPSPLFPGPSKPFWV LVVVGGVLACYSLLVTVAFIIFWVRSKRSRLLHSDYMNMT PRRPGPTRKHYQPYAPPRDFAAYRSRVKFSRSADAPAYQQ GQNQLYNELNLGRREEYDVLDKRRGRDPEMGGKPRRKNP QEGLYNELQKDKMAEAYSEIGMKGERRRGKGHDGLYQGL STATKDTYDALHMQALPPR |
| 29 | MAGEA4 (230-239) 33229 VL-VH BBz CAR | DIQMTQSPSSLSASVGDRVTITCQASQDISNYLNWYQQKRG KAPKLLIYDASILETGVPSRFSGSGSGTDFTFTISSLQPEDIAT YFCQQFDNVPLTFGGGTKVEIKGGGGSGGGGSGGGGSEVQ LVESGGGLVQPGRSLRLSCAASGFTFDDYAMHWVRQAPG KGLEWVSGISWNSGSIAYADSVKGRFTISRDNAKNSLYLQ MNSLRSEDTALYHCAKDWRRTNYYGMDVWGQGTTVTVS SGGGGSTTTPAPRPPTPAPTIASQPLSLRPEACRPAAGGAVH TRGLDFACDIYIWAPLAGTCGVLLLSLVITLYCKRGRKKLL YIFKQPFMRPVQTTQEEDGCSCRFPEEEEGGCELRVKFSRS ADAPAYQQGQNQLYNELNLGRREEYDVLDKRRGRDPEMG GKPRRKNPQEGLYNELQKDKMAEAYSEIGMKGERRRGKG HDGLYQGLSTATKDTYDALHMQALPPRGSGATNFSLLKQ AGDVEENPGPMVSKGEELFTGVVPILVELDGDVNGHKFSV SGEGEGDATYGKLTLKFICTTGKLPVPWPTLVTTLTYGVQC FSRYPDHMKQHDFFKSAMPEGYVQERTIFFKDDGNYKTRA EVKFEGDTLVNRIELKGIDFKEDGNILGHKLEYNYNSHNVY IMADKQKNGIKVNFKIRHNIEDGSVQLADHYQQNTPIGDGP VLLPDNHYLSTQSALSKDPNEKRDHMVLLEFVTAAGITLG MDELYK* |
| 30 | MAGEA4 (230-239) 33229 VL-VH CD28z CAR | DIQMTQSPSSLSASVGDRVTITCQASQDISNYLNWYQQKRG KAPKLLIYDASILETGVPSRFSGSGSGTDFTFTISSLQPEDIAT YFCQQFDNVPLTFGGGTKVEIKGGGGSGGGGSGGGGSEVQ LVESGGGLVQPGRSLRLSCAASGFTFDDYAMHWVRQAPG KGLEWVSGISWNSGSIAYADSVKGRFTISRDNAKNSLYLQ MNSLRSEDTALYHCAKDWRRTNYYGMDVWGQGTTVTVS SGGGGSIEVMYPPPYLDNEKSNGTIIHVKGKHLCPSPLFPGP SKPFWVLVVVGGVLACYSLLVTVAFIIFWVRSKRSRLLHSD YMNMTPRRPGPTRKHYQPYAPPRDFAAYRSRVKFSRSADA PAYQQGQNQLYNELNLGRREEYDVLDKRRGRDPEMGGKP |

TABLE 3-continued

Exemplary CAR Polypeptides

| SEQ ID NO: | CAR ID | Sequence |
|---|---|---|
| | | RRKNPQEGLYNELQKDKMAEAYSEIGMKGERRRGKGHDG<br>LYQGLSTATKDTYDALHMQALPPRGSGATNFSLLKQAGD<br>VEENPGPMVSKGEELFTGVVPILVELDGDVNGHKFSVSGE<br>GEGDATYGKLTLKFICTTGKLPVPWPTLVTTLTYGVQCFSR<br>YPDHMKQHDFFKSAMPEGYVQERTIFFKDDGNYKTRAEV<br>KFEGDTLVNRIELKGIDFKEDGNILGHKLEYNYNSHNVYIM<br>ADKQKNGIKVNFKIRHNIEDGSVQLADHYQQNTPIGDGPV<br>LLPDNHYLSTQSALSKDPNEKRDHMVLLEFVTAAGITLGM<br>DELYK* |
| 33 | MAGEA4 (230-239) 34852 VH-VL BBz CAR P2A-GFP | EVQLLESGGGLVQPGGSLRLTCAASGFTFRSYAMSWVRQA<br>PGKGLEWVSTISGNSDSTYYADSVKGRFTISRENSKNTLYL<br>QMNSLRAEDTAVYYCAKDLHITMVRGAIPADVFDIWGQG<br>TMVTVSSGGGGSGGGGSGGGGSDIQMTQSPSSLSASVGDR<br>VTITCRASQSISFYLNWYQQKPGKAPKLLIYAASSLQSGVPS<br>RFSGSGSETDFTLTISSLQPEDFATYYCQQSYSTPPITFGQGT<br>RLEIKGGGGSTTTPAPRPPTPAPTIASQPLSLRPEACRPAAG<br>GAVHTRGLDFACDIYIWAPLAGTCGVLLLSLVITLYCKRGR<br>KKLLYIFKQPFMRPVQTTQEEDGCSCRFPEEEEGGCELRVK<br>FSRSADAPAYQQGQNQLYNELNLGRREEYDVLDKRRGRD<br>PEMGGKPRRKNPQEGLYNELQKDKMAEAYSEIGMKGERR<br>RGKGHDGLYQGLSTATKDTYDALHMQALPPRGSGATNFS<br>LLKQAGDVEENPGPMVSKGEELFTGVVPILVELDGDVNGH<br>KFSVSGEGEGDATYGKLTLKFICTTGKLPVPWPTLVTTLTY<br>GVQCFSRYPDHMKQHDFFKSAMPEGYVQERTIFFKDDGNY<br>KTRAEVKFEGDTLVNRIELKGIDFKEDGNILGHKLEYNYNS<br>HNVYIMADKQKNGIKVNFKIRHNIEDGSVQLADHYQQNTP<br>IGDGPVLLPDNHYLSTQSALSKDPNEKRDHMVLLEFVTAA<br>GITLGMDELYK* |
| 34 | MAGEA4 (230-239) 34852 VH-VL CD28hinge/TM/cytoCD3z CAR P2A-GFP | EVQLLESGGGLVQPGGSLRLTCAASGFTFRSYAMSWVRQA<br>PGKGLEWVSTISGNSDSTYYADSVKGRFTISRENSKNTLYL<br>QMNSLRAEDTAVYYCAKDLHITMVRGAIPADVFDIWGQG<br>TMVTVSSGGGGSGGGGSGGGGSDIQMTQSPSSLSASVGDR<br>VTITCRASQSISFYLNWYQQKPGKAPKLLIYAASSLQSGVPS<br>RFSGSGSETDFTLTISSLQPEDFATYYCQQSYSTPPITFGQGT<br>RLEIKGGGGSIEVMYPPPYLDNEKSNGTIIHVKGKHLCPSPL<br>FPGPSKPFWVLVVVGGVLACYSLLVTVAFIIFWVRSKRSRL<br>LHSDYMNMTPRRPGPTRKHYQPYAPPRDFAAYRSVKFSR<br>SADAPAYQQGQNQLYNELNLGRREEYDVLDKRRGRDPEM<br>GGKPRRKNPQEGLYNELQKDKMAEAYSEIGMKGERRRGK<br>GHDGLYQGLSTATKDTYDALHMQALPPRGSGATNFSLLK<br>QAGDVEENPGPMVSKGEELFTGVVPILVELDGDVNGHKFS<br>VSGEGEGDATYGKLTLKFICTTGKLPVPWPTLVTTLTYGV<br>QCFSRYPDHMKQHDFFKSAMPEGYVQERTIFFKDDGNYKT<br>RAEVKFEGDTLVNRIELKGIDFKEDGNILGHKLEYNYNSHN<br>VYIMADKQKNGIKVNFKIRHNIEDGSVQLADHYQQNTPIG<br>DGPVLLPDNHYLSTQSALSKDPNEKRDHMVLLEFVTAAGI<br>TLGMDELYK* |

In certain embodiments, the binding domain and/or extracellular domain of a CAR provided herein provides the CAR with the ability to bind to the target antigen of interest. A binding domain (e.g., a ligand-binding domain or antigen-binding domain) can be any protein, polypeptide, oligopeptide, or peptide that possesses the ability to specifically recognize and bind to a biological molecule (e.g., a cell surface receptor or tumor protein, or a component thereof). A binding domain includes any naturally occurring, synthetic, semi-synthetic, or recombinantly produced binding partner for a biological molecule of interest. For example, and as further described herein, a binding domain may be antibody light chain and heavy chain variable regions, or the light and heavy chain variable regions can be joined together in a single chain and in either orientation (e.g., $V_L$-$V_H$ or $V_H$-$V_L$). A variety of assays are known for identifying binding domains of the present disclosure that specifically bind with a particular target, including Western blot, ELISA, flow cytometry, or surface plasmon resonance analysis (e.g., using BIACORE analysis). The target may be an antigen of clinical interest against which it would be desirable to trigger an effector immune response that results in tumor killing. The CAR polypeptide may comprises a variable light chain comprising any one of the amino acid sequences set forth in SEQ ID NO: 16 to 19, 31, or 37. A variable light chain disclosed herein may comprise at least 50%, at least 60%, at least 70%, at least 80%, at least 90%, at least 91%, at least 92%, at least 93%, at least 94%, at least 95%, at least 96%, at least 97%, at least 98%, or at least 99% homology to an amino acid sequence set forth in SEQ ID NO: 16 to 19, 31, or 37. The CAR polypeptide may comprise a variable heavy chain comprising any one of the amino acid sequences set forth in SEQ ID NO: 20 to 23, 32, or 38. A variable heavy chain disclosed herein may comprise at least 50%, at least 60%, at least 70%, at least 80%, at least 90%, at least 91%, at least 92%, at least 93%, at least 94%, at least 95%, at least 96%, at least 97%, at least 98%, or at least 99% homology to an amino acid sequence set forth in SEQ ID NO: 20 to 23, 32, or 38.

TABLE 4

Exemplary Variable Light Chain

| SEQ ID NO: | Construct ID | Sequence |
|---|---|---|
| 16 | HPV (Control CAR) 17363 VL-VH BBz | DIQMTQSPSSLSASVGDRVTITCRASQSISSYLNWYQQKPGKAPKLLIYAVSILQSGVPSRFSGSGSGTDFTLTINSLQPEDFATYSCQQTYSTPPITFGQGTRLEIK |
| 17 | MAGEA4 (286-294) 31345 VL-VH BBz CAR | DIQMTQSPSSLSASVGDRVTITCRASQSISSYLNWYQQKPGKAPKLLIYAASSLQSGVPSRFSGSGSGTDFTLTISSLQPEDFATYYCQQSYSTPPITFGQGTRLEIKR |
| 18 | NY-ESO (157-165) 28105 VH-VL BBz CAR | DIQMTQSPSSLSASEGDRVTITCRASQSISTYLNWYQQKPGKAPKLLIYGASSLQSGVPSRFSGSGSGTDFTLTISSLQPEDFATYYCQQSYSTPPITFGQGTKVEIK |
| 19 | Tyrosinase D11 VL-VH BBz CAR | DIQMTQSPASLSVSVGETVTITCRASDIIYSNLAWYQQKQGKSPQLLVYAATNLAAGVPSRFSGSGSGTQYSLKINSLQSEDFGTYYCQHFWGSSISFGSGTKLEIK |
| 31 | MAGEA4 (230-239) 33229 VL-VH BBz CAR | DIQMTQSPSSLSASVGDRVTITCQASQDISNYLNWYQQKRGKAPKLLIYDASILETGVPSRFSGSGSGTDFTFTISSLQPEDIATYFCQQFDNVPLTFGGGTKVEIK |
| 37 | MAGEA4 (230-239) 34852 VH-VL BBz CAR | DIQMTQSPSSLSASVGDRVTITCRASQSISFYLNWYQQKPGKAPKLLIYAASSLQSGVPSRFSGSGSETDFTLTISSLQPEDFATYYCQQSYSTPPITFGQGTRLEIK |

TABLE 5

Exemplary Variable Heavy Chain

| SEQ ID NO: | Construct ID | Sequence |
|---|---|---|
| 20 | HPV 17363 VL-VH BBz | EVQLLESGGGLVQPGGSLRLSCAASGFTFSSYAMTWVRQAPGMGLEWVSVISGSGSETYYADSVKGRFTISRDNSKNTLYLQMNSLRAEDTAVYYCVKDSSYRSSSRAYYYYGMDVWGLGTTVTVSS |
| 21 | MAGEA4 (286-294) 31345 VL-VH BBz CAR | QVQLVESGGGLVKPGGSLRLSCAASGFTFSEYYMTWIRQAPGQGLEWVSYISSSGFNIYYADSVKGRFTISRDNAKNSLFLQMNSLRVEDTAVYYCAREGVTDGMDVWGQGTTVTVSS |
| 22 | NY-ESO (157-165) 28105 VH-VL BBz CAR | EVQLVESGGGVVQPGGSLRLSCEASGFIFDDYAMHWVRQAPGKGLEWVSLISGDGDIIYYADSVKGRFTISRDNSKNSLYLQMNSLIIEDTALYYCAKDWVFGVVMTHYWYFGLDVWGQGTTVTVSS |
| 23 | Tyrosinase D11 VL-VH BBz CAR | QVQLKESGPGLVAPSQSLSITCTVSGFSLTSYGVHWVRQPPGKGLEWLGVIWAGGTTNYNSALMSRLSISRDNSKSQVFLEMNSLQTDDTAIYYCARDGHFHFDFWGQGTTLTVSS |
| 32 | MAGEA4 (230-239) 33229 VL-VH BBz CAR | EVQLVESGGGLVQPGRSLRLSCAASGFTFDDYAMHWVRQAPGKGLEWVSGISWNSGSIAYADSVKGRFTISRDNAKNSLYLQMNSLRSEDTALYHCAKDWRRTNYYGMDVWGQGTTVTVSS |
| 38 | MAGEA4 (230-239) 34852 VH-VL BBz | RVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |

TABLE 6

Exemplary Variable Light Chain and heavy chain nucleic acid sequences

| SEQ ID NO: | Construct ID | Sequence |
|---|---|---|
| 24 | MAGEA4 (286-294) 31345 VL | ACATCCAGAT GACCCAGTCT CCATCCTCCC TGTCTGCATC TGTAGGAGAC AGAGTCACCA TCACTTGCCG GGCAAGTCAG AGCATTAGCA GCTATTTAAA TTGGTATCAG CAGAAACCAG GGAAAGCCCC TAAGCTCCTG ATCTATGCTG CATCCAGTTT GCAAAGTGGG GTCCCGTCAA GGTTCAGTGG CAGTGGATCT GGGACAGATT TCACTCTCAC CATCAGCAGT CTGCAACCTG AAGATTTTGC AACTTACTAC TGTCAACAGA GTTACAGTAC CCCTCCGATC ACCTTCGGCC AAGGGACACG ACTGGAGATT AAACGA |
| 25 | MAGEA4 (286-294) 31345 VH | AGGTGCAGCT GGTGGAGTCT GGGGGAGGCT TGGTCAAGCC TGGAGGGTCC CTGAGACTCT CCTGTGCAGC CTCTGGATTC ACTTTCAGTG AATACTACAT GACCTGGATC CGCCAGGCTC CAGGGCAGGG GCTGGAGTGG GTTTCATACA TTAGTAGTAG TGGTTTTAAC ATATACTACG CAGACTCTGT GAAGGGCCGA TTCACCATCT CAAGGGACAA CGCCAAGAAC TCACTGTTTC TGCAAATGAA CAGCCTGAGA GTCGAGGACA CGGCCGTATA TTACTGTGCG AGAGAAGGTG TAACGGACGG TATGGACGTC TGGGGCCAAG GGACCACGGT CACCGTCTCC TCA |
| 39 | MAGEA4 (230-239) 34852 VL | GACATCCAGATGACCCAGAGCCCTTCTAGCCTGTCC GCCTCTGTGGGCGATAGAGTGACCATCACATGCAG GGCCAGCCAGTCCATCTCTTTCTACCTGAACTGGTA TCAGCAGAAGCCAGGCAAGGCCCCCAAGCTGCTGA TCTACGCAGCATCCTCTCTGCAGTCTGGAGTGCCAA GCAGGTTCAGCGGATCCGGATCTGAGACCGACTTT ACCCTGACAATCAGCTCCCTGCAGCCTGAGGATTTC GCCACATACTATTGTCAGCAGAGCTATTCCACCCCC CCTATCACATTTGGCCAGGGAACCAGGCTGGAGAT CAAG |
| 40 | MAGEA4 (230-239) 34852 VH | GAGGTGCAGCTGCTGGAGAGCGGAGGAGGCCTGGT GCAGCCTGGAGGATCTCTGAGGCTGACCTGCGCAG CAAGCGGCTTCACATTTCGCTCCTACGCAATGTCTT GGGTGCGGCAGGCACCAGGCAAGGGACTGGAGTGG GTGAGCACCATCTCCGGCAATTCTGACAGCACATAC TATGCCGATTCTGTGAAGGGCCGCTTTACCATCAGC CGGGAGAACTCCAAGAATACACTGTATCTGCAGAT GAACAGCCTGAGGGCCGAGGACACCGCCGTGTACT ATTGTGCCAAGGATCTGCACATCACAATGGTGCGC GGAGCAATCCCAGCAGACGTGTTCGATATCTGGGG CCAGGGCACCATGGTGACAGTGAGCTCC |

In one embodiment, the binding domain of the CAR is a single chain antibody (scFv) specific for a peptide in groove or low density cancer antigen, and may be a murine, human or humanized scFv. Single chain antibodies may be cloned from the V region genes of a hybridoma specific for a desired target. A technique which can be used for cloning the variable region heavy chain (VH) and variable region light chain (VL) has been described, for example, in Orlandi et al., PNAS, 1989; 86:3833-3837. Thus, in certain embodiments, a binding domain comprises an antibody-derived binding domain but can be a non-antibody derived binding domain. An antibody-derived binding domain can be a fragment of an antibody or a genetically engineered product of one or more fragments of the antibody, which fragment is involved in binding with the antigen.

In certain embodiments, the CARs of the present disclosure may comprise a linker between the various domains, added for appropriate spacing and conformation of the molecule. For example, in one embodiment, there may be a linker between the binding domain VH or VL which may be between 1-10 amino acids long. In other embodiments, the linker between any of the domains of the chimeric antigen receptor may be between 1-20 or 20 amino acids long. In this regard, the linker may be 1, 2, 3, 4, 5, 6, 7, 8, 9, 10, 11, 12, 13, 14, 15, 16, 17, 18, 19 or 20 amino acids long. In further embodiments, the linker may be 21, 22, 23, 24, 25, 26, 27, 28, 29 or 30 amino acids long. Ranges including the numbers described herein are also included herein, e.g., a linker 10-30 amino acids long.

In certain embodiments, linkers suitable for use in the CAR described herein are flexible linkers. Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers (G)n, glycine-serine polymers, where n is an integer of at least one, glycine-alanine polymers, alanine-serine polymers, and other flexible linkers known in the art. Glycine and glycine-serine polymers are relatively unstructured, and therefore may be able to serve as a neutral tether between domains of fusion proteins such as the CARs described herein. Glycine accesses significantly more phi-psi space than even alanine, and is much less restricted than residues with longer side chains. The ordinarily skilled artisan will recognize that design of a CAR can include linkers that are all or partially flexible, such that the linker can include a flexible linker as well as one or more portions that confer less flexible structure to provide for a desired CAR structure.

The binding domain of the CAR may be followed by a "spacer," or, "hinge," which refers to the region that moves the antigen binding domain away from the effector cell surface to enable proper cell/cell contact, antigen binding and activation (Patel et al., Gene Therapy, 1999; 6:412-419). The hinge region in a CAR is generally between the transmembrane (TM) and the binding domain. In certain embodiments, a hinge region is an immunoglobulin hinge region and may be a wild type immunoglobulin hinge region or an altered wild type immunoglobulin hinge region. Other exemplary hinge regions used in the CARs described herein include the hinge region derived from the extracellular regions of type 1 membrane proteins such as CD8α, CD4, CD28 and CD7, which may be wild-type hinge regions from these molecules or may be altered.

The "transmembrane" region or domain is the portion of the CAR that anchors the extracellular binding portion to the plasma membrane of the immune effector cell, and facilitates binding of the binding domain to the target antigen. In some embodiments, the transmembrane domain may be a CD3ζ transmembrane domain. Other transmembrane domains that may be employed in some embodiments include those obtained from CD8, CD8α, CD4, CD28, CD45, CD9, CD16, CD22, CD33, CD64, CD80, CD86, CD134, CD137, and CD154. In certain embodiments, the transmembrane domain is synthetic in which case it would comprise predominantly hydrophobic residues such as leucine and valine.

In certain embodiments, the CARs provided herein comprise an intracellular signaling domain. The intracellular signaling domain (also referred to herein as the "signaling domain") comprises the part of the chimeric antigen receptor protein that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain.

In certain embodiments, the CARs provided herein comprise one or more immunoreceptor tyrosine-based activation motifs or ITAMs. Examples of ITAM containing primary cytoplasmic signaling sequences that are of use include those derived from TCRζ, FcRgamma, FcRβ, CD3γ, CD3δ, CD3ε, CD5, CD22, CD79a, CD79b and CD66d. In one embodiment, the intracellular signaling domain of the CARs described herein are derived from CD34.

In certain embodiments, the CARs provided herein further comprise a costimulatory domain. Costimulatory molecules are cell surface molecules other than antigen receptors or Fc receptors that provide a second signal required for efficient activation and function of T lymphocytes upon binding to antigen. Examples of such co-stimulatory molecules include CD27, CD28, 4-1BB (CD137), OX40 (CD134), CD30, CD40, PD-1, ICOS (CD278), LFA-1, CD2, CD7, LIGHT, NKD2C, B7-H2 and a ligand that specifically binds CD83. Accordingly, while the present disclosure provides exemplary costimulatory domains derived from CD28. The inclusion of one or more co-stimulatory signaling domains may enhance the efficacy and expansion of T cells expressing CAR receptors. Also disclosed herein are CAR polypeptides, wherein the intracytoplasmic/costimulatory region of the CAR polypeptide further comprises a 4-1BB domain (e.g., in addition to a CD28/ζ domain). The costimulatory region of such a CAR polypeptide may comprise a complete 4-1BB domain or fragment thereof, and/or a complete CD28/ζ domain or fragment thereof. The intracellular signaling and costimulatory signaling domains may be linked in any order in tandem to the carboxyl terminus of the transmembrane domain.

The CAR polypeptide sequence disclosed herein may comprise any one of the amino acid sequences set forth in SEQ ID NO 26 to 28. A CAR polypeptide disclosed herein may comprise at least amino acid sequence with at least 50%, at least 60%, at least 70%, at least 80%, at least 90%, at least 91%, at least 92%, at least 93%, at least 94%, at least 95%, at least 96%, at least 97%, at least 98%, or at least 99% homology to an amino acid sequence set forth in SEQ ID NO: 26 to 28.

TABLE 7

Additional Exemplary CAR Sequences:

| | | |
|---|---|---|
| SEQ ID NO: 26 | CD3ζ | RVKFSRSADAPAYQQGQNQLYNELNLGR REEYDVLDKRRGRDPEMGGKPRRKNPQE GLYNELQKDKMAEAYSEIGMKGERRRGK GHDGLYQGLSTATKDTYDALHMQALPPR |
| SEQ ID NO: 27 | CD8 | TTTPAPRPPTPAPTIASQPLSLRPEACR PAAGGAVHTRGLDFACDIYIWAPLAGTC GVLLLSLVITLYC |
| SEQ ID NO: 28 | 4-1BB | KRGRKKLLYIFKQPFMRPVQTTQEEDGC SCRFPEEEEGGCEL |

Nucleic Acids and Vectors

In certain aspects, also disclosed are nucleic acids and polynucleotide vectors encoding the CAR polypeptides disclosed herein.

Nucleic acid sequences encoding the disclosed CARs, and regions thereof, can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

Expression of nucleic acids encoding CARs is typically achieved by operably linking a nucleic acid encoding the CAR polypeptide to a promoter, and incorporating the construct into an expression vector. Typical cloning vectors contain transcription and translation terminators, initiation sequences, and promoters useful for regulation of the expression of the desired nucleic acid sequence.

In certain embodiments, the polynucleotide encoding the CAR described herein is inserted into a vector. The vector is a vehicle into which a polynucleotide encoding a protein may be covalently inserted so as to bring about the expression of that protein and/or the cloning of the polynucleotide. Such vectors may also be referred to as "expression vectors". The isolated polynucleotide may be inserted into a vector using any suitable methods known in the art, for example, without limitation, the vector may be digested using appropriate restriction enzymes and then may be ligated with the isolated polynucleotide having matching restriction ends. Expression vectors have the ability to incorporate and express heterologous or modified nucleic acid sequences coding for at least part of a gene product capable of being transcribed in a cell. In most cases, RNA molecules are then translated into a protein. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well and are discussed infra. An expression vector may comprise additional elements, for example, the expression vector may have two replication systems, thus allowing it to be maintained in two organisms, for example in human cells for expression and in a prokaryotic host for cloning and amplification.

The expression vector may have the necessary 5' upstream and 3' downstream regulatory elements such as promoter sequences such as CMV, PGK and EF1alpha. promoters, ribosome recognition and binding TATA box, and 3' UTR AAUAAA transcription termination sequence for the efficient gene transcription and translation in its respective host cell. Other suitable promoters include the constitutive promoter of simian virus 40 (SV40) early promoter, mouse mammary tumor virus (MMTV), HIV LTR promoter, MoMuLV promoter, avian leukemia virus promoter, EBV immediate early promoter, and rous sarcoma virus promoter. Human gene promoters may also be used, including, but not limited to the actin promoter, the myosin promoter, the hemoglobin promoter, and the creatine kinase promoter. In certain embodiments inducible promoters are also contemplated as part of the vectors expressing chimeric antigen receptor. This provides a molecular switch capable of turning on expression of the polynucleotide sequence of interest or turning off expression. Examples of inducible promoters include, but are not limited to a metallothionine promoter, a glucocorticoid promoter, a progesterone promoter, or a tetracycline promoter.

The expression vector may have additional sequence such as 6x-histidine (SEQ ID NO: 41), c-Myc, and FLAG tags which are incorporated into the expressed CARs. Thus, the expression vector may be engineered to contain 5' and 3' untranslated regulatory sequences that sometimes can function as enhancer sequences, promoter regions and/or terminator sequences that can facilitate or enhance efficient transcription of the nucleic acid(s) of interest carried on the expression vector. An expression vector may also be engineered for replication and/or expression functionality (e.g., transcription and translation) in a particular cell type, cell location, or tissue type. Expression vectors may include a selectable marker for maintenance of the vector in the host or recipient cell.

In various embodiments, the vectors are plasmid, autonomously replicating sequences, and transposable elements. Additional exemplary vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Examples of categories of animal viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40). Examples of expression vectors are Lenti-X™ Bicistronic Expression System (Neo) vectors (Clontrch), pClneo vectors (Promega) for expression in mammalian cells; pLenti4/V5-DEST™, pLenti6/V5-DEST™, and pLenti6.2N5-GW/lacZ (Invitrogen) for lentivirus-mediated gene transfer and expression in mammalian cells. The coding sequences of the CARs disclosed herein can be ligated into such expression vectors for the expression of the chimeric protein in mammalian cells.

In certain embodiments, the nucleic acids encoding the CAR are provided in a viral vector. A viral vector can be that derived from, for example, a retrovirus (e.g., a foamy virus) or lentivirus. As used herein, the term, "viral vector," refers to a nucleic acid vector construct that includes at least one element of viral origin and has the capacity to be packaged into a viral vector particle. The viral vector can contain the coding sequence for the various chimeric proteins described herein in place of nonessential viral genes. The vector and/or particle can be utilized for the purpose of transferring DNA, RNA or other nucleic acids into cells either in vitro or in vivo. Numerous forms of viral vectors are known in the art.

In certain embodiments, the viral vector containing the coding sequence for a CAR described herein is a retroviral vector or a lentiviral vector. The term "retroviral vector" refers to a vector containing structural and functional genetic elements that are primarily derived from a retrovirus. The term "lentiviral vector" refers to a vector containing structural and functional genetic elements outside the LTRs that are primarily derived from a lentivirus.

The retroviral vectors for use herein can be derived from any known retrovirus (e.g., type c retroviruses, such as Moloney murine sarcoma virus (MOMSV), Harvey murine sarcoma virus (HaMuSV), murine mammary tumor virus (MuMTV), gibbon ape leukemia virus (GaLV), feline leukemia virus (FLV), spumavirus, Murine Stem Cell Virus (MSCV) and Rous Sarcoma Virus (RSV)). Retroviruses" also include human T cell leukemia viruses, HTLV-1 and HTLV-2, and the lentiviral family of retroviruses, such as Human Immunodeficiency Viruses, HIV-1, HIV-2, simian immunodeficiency virus (SIV), feline immunodeficiency virus (FIV), equine immunodeficiency virus (EIV), and other classes of retroviruses.

A lentiviral vector for use herein refers to a vector derived from a lentivirus, a group (or genus) of retroviruses that give rise to slowly developing disease. Viruses included within this group include HIV (human immunodeficiency virus; including HIV type 1, and HIV type 2); visna-maedi; a caprine arthritis-encephalitis virus; equine infectious anemia virus; feline immunodeficiency virus (FIV); bovine immune deficiency virus (BIV); and simian immunodeficiency virus (SIV). Preparation of the recombinant lentivirus can be achieved using the methods according to Dull et al. and Zufferey et al. (Dull et al., J. Virol., 1998; 72:8463-8471 and Zufferey et al., J. Virol. 1998; 72:9873-9880).

Retroviral vectors (i.e., both lentiviral and non-lentiviral) for use can be formed using standard cloning techniques by combining the desired DNA sequences in the order and orientation described herein (Current Protocols in Molecular Biology, Ausubel, F. M. et al. (eds.) Greene Publishing Associates, (1989), Sections 9.10-9.14 and other standard laboratory manuals; Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992)

Human Gene Therapy 3:641-647; Dai et al. (1992) Proc. Natl. Acad. Sci. USA 89:10892-10895; Hwu et al. (1993) J. Immunol 150:4104-4115; U.S. Pat. Nos. 4,868,116; 4,980,286; PCT Application WO 89/07136; PCT Application WO 89/02468; PCT Application WO 89/05345; and PCT Application WO 92/07573).

Suitable sources for obtaining retroviral (i.e., both lentiviral and non-lentiviral) sequences for use in forming the vectors include, for example, genomic RNA and cDNAs available from commercially available sources, including the Type Culture Collection (ATCC), Rockville, Md. The sequences also can be synthesized chemically.

For expression of a CAR, the vector may be introduced into a host cell to allow expression of the polypeptide within the host cell. The expression vectors may contain a variety of elements for controlling expression, including without limitation, promoter sequences, transcription initiation sequences, enhancer sequences, selectable markers, and signal sequences. These elements may be selected as appropriate by a person of ordinary skill in the art, as described above. For example, the promoter sequences may be selected to promote the transcription of the polynucleotide in the vector. Suitable promoter sequences include, without limitation, T7 promoter, T3 promoter, SP6 promoter, beta-actin promoter, EF1a promoter, CMV promoter, and SV40 promoter. Enhancer sequences may be selected to enhance the transcription of the polynucleotide. Selectable markers may be selected to allow selection of the host cells inserted with the vector from those not, for example, the selectable markers may be genes that confer antibiotic resistance. Signal sequences may be selected to allow the expressed polypeptide to be transported outside of the host cell.

For cloning of the polynucleotide, the vector may be introduced into a host cell (an isolated host cell) to allow replication of the vector itself and thereby amplify the copies of the polynucleotide contained therein. The cloning vectors may contain sequence components generally include, without limitation, an origin of replication, promoter sequences, transcription initiation sequences, enhancer sequences, and selectable markers. These elements may be selected as appropriate by a person of ordinary skill in the art. For example, the origin of replication may be selected to promote autonomous replication of the vector in the host cell.

In certain embodiments, the present disclosure provides isolated host cells containing the vectors provided herein. The host cells containing the vector may be useful in expression or cloning of the polynucleotide contained in the vector. Suitable host cells can include, without limitation, prokaryotic cells, fungal cells, yeast cells, or higher eukaryotic cells such as mammalian cells. Suitable prokaryotic cells for this purpose include, without limitation, eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*.

The CARs are introduced into a host cell using transfection and/or transduction techniques known in the art. As used herein, the terms, "transfection," and, "transduction," refer to the processes by which an exogenous nucleic acid sequence is introduced into a host cell. The nucleic acid may be integrated into the host cell DNA or may be maintained extrachromosomally. The nucleic acid may be maintained transiently or may be a stable introduction. Transfection may be accomplished by a variety of means known in the art including but not limited to calcium phosphate-DNA co-precipitation, DEAE-dextran-mediated transfection, polybrene-mediated transfection, electroporation, microinjection, liposome fusion, lipofection, protoplast fusion, retroviral infection, and biolistics. Transduction refers to the delivery of a gene(s) using a viral or retroviral vector by means of viral infection rather than by transfection. In certain embodiments, retroviral vectors are transduced by packaging the vectors into virions prior to contact with a cell. For example, a nucleic acid encoding a CAR carried by a retroviral vector can be transduced into a cell through infection and pro virus integration.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene. Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well known in the art. See, for example, Sambrook et al. (2001, Molecular Cloning: A Laboratory Manual, Cold Spring Harbor Laboratory, New York).

In the case where a non-viral delivery system is utilized, an exemplary delivery vehicle is a liposome. In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes. Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc, (Birmingham, Ala.).

Immune Effector Cells

In certain aspects, also disclosed herein are immune effector cells that are engineered to express the disclosed CAR polypeptides. In some embodiments, the cells are obtained from the subject to be treated (i.e., are autologous). However, in certain embodiments, immune effector cell lines or donor effector cells (allogeneic) are used.

Immune effector cells can be obtained from a number of sources, including peripheral blood mononuclear cells, bone marrow, lymph node tissue, cord blood, thymus tissue, tissue from a site of infection, ascites, pleural effusion, spleen tissue, and tumors. Immune effector cells can be obtained from blood collected from a subject using any number of techniques known to the skilled artisan, such as Ficoll™ separation. For example, cells from the circulating blood of an individual may be obtained by apheresis. In some embodiments, immune effector cells are isolated from peripheral blood lymphocytes by lysing the red blood cells and depleting the monocytes, for example, by centrifugation through a PERCOLL™ gradient or by counterflow centrifugal elutriation. A specific subpopulation of immune effector cells can be further isolated by positive or negative selection techniques. For example, immune effector cells can be isolated using a combination of antibodies directed to surface markers unique to the positively selected cells, e.g., by incubation with antibody-conjugated beads for a time period sufficient for positive selection of the desired immune effector cells. Alternatively, enrichment of immune effector cells population can be accomplished by negative selection using a combination of antibodies directed to surface markers unique to the negatively selected cells.

The present disclosure provides methods for making the immune effector cells which express the CARs described herein. In one embodiment, the method comprises transfecting or transducing immune effector cells isolated from a subject, such as a subject having a PIG and/or low density cancer antigen expressing tumor cell, such that the immune effector cells express one or more CAR as described herein. In certain embodiments, the immune effector cells are isolated from an individual and genetically modified without further manipulation in vitro. Such cells can then be directly re-administered into the individual. In further embodiments, the immune effector cells are first activated and stimulated to proliferate in vitro prior to being genetically modified to express a CAR. In this regard, the immune effector cells may be cultured before or after being genetically modified (i.e., transduced or transfected to express a CAR as described herein).

Prior to in vitro manipulation or genetic modification of the immune effector cells described herein, the source of cells may be obtained from a subject. In particular, the immune effector cells for use with the CARs as described herein comprise T cells. T cells can be obtained from a number of sources, including peripheral blood mononuclear cells, bone marrow, lymph nodes tissue, cord blood, thymus issue, tissue from a site of infection, ascites, pleural effusion, spleen tissue, and tumors. In certain embodiments, T cell can be obtained from a unit of blood collected from the subject using any number of techniques known to the skilled person, such as FICOLL separation. In one embodiment, cells from the circulating blood of an individual are obtained by apheresis. The apheresis product typically contains lymphocytes, including T cells, monocytes, granulocyte, B cells, other nucleated white blood cells, red blood cells, and platelets. In one embodiment, the cells collected by apheresis may be washed to remove the plasma fraction and to place the cells in an appropriate buffer or media for subsequent processing. In one embodiment, the cells are washed with PBS. In an alternative embodiment, the washed solution lacks calcium, and may lack magnesium or may lack many, if not all, divalent cations. As would be appreciated by those of ordinary skill in the art, a washing step may be accomplished by methods known to those in the art, such as by using a semiautomated flowthrough centrifuge. After washing, the cells may be resuspended in a variety of biocompatible buffers or other saline solution with or without buffer. In certain embodiments, the undesirable components of the apheresis sample may be removed in the cell directly resuspended culture media.

In certain embodiments, T cells are isolated from peripheral blood mononuclear cells (PBMCs) by lysing the red blood cells and depleting the monocytes, for example, by centrifugation through a PERCOLL™ gradient. A specific subpopulation of T cells, such as CD28+, CD4+, CD8+, CD45RA+, and CD45RO+ T cells, can be further isolated by positive or negative selection techniques. For example, enrichment of a T cell population by negative selection can be accomplished with a combination of antibodies directed to surface markers unique to the negatively selected cells. One method for use herein is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD1 b, CD16, HLA-DR, and CD8. Flow cytometry and cell sorting may also be used to isolate cell populations of interest.

PBMCs may be used directly for genetic modification with the CARs using methods as described herein. In certain embodiments, after isolation of PBMC, T lymphocytes are further isolated and in certain embodiments, both cytotoxic and helper T lymphocytes can be sorted into naive, memory, and effector T cell subpopulations either before or after genetic modification and/or expansion. CD8+ cells can be obtained by using standard methods. In some embodiments, CD8+ cells are further sorted into naive, central memory, and effector cells by identifying cell surface antigens that are associated with each of those types of CD8+ cells. In embodiments, memory T cells are present in both CD62L+ and CD62L-subsets of CD8+ peripheral blood lymphocytes. PBMC are sorted into CD62L-CD8+ and CD62L+CD8+ fractions after staining with anti-CD8 and anti-CD62L antibodies. In some embodiments, the expression of phenotypic markers of central memory TCM include CD45RO, CD62L, CCR7, CD28, CD3, and CD127 and are negative for granzyme B. In some embodiments, central memory T cells are CD45RO+, CD62L+, CD8+ T cells. In some embodiments, effector T cells are negative for CD62L, CCR7, CD28, and CD127, and positive for granzyme B and perforin. In some embodiments, naive CD8+T lymphocytes are characterized by the expression of phenotypic markers of naive T cells including CD62L, CCR7, CD28, CD3, CD 127, and CD45RA.

In certain embodiments, CD4+ T cells are further sorted into subpopulations. For example, CD4+T helper cells can be sorted into naive, central memory, and effector cells by identifying cell populations that have cell surface antigens. CD4+ lymphocytes can be obtained by standard methods. In some embodiments, naive CD4+T lymphocytes are CD45RO−, CD45RA+, CD62L+CD4+ T cell. In some embodiments, central memory CD4+ cells are CD62L positive and CD45RO positive. In some embodiments, effector CD4+ cells are CD62L and CD45RO negative.

The immune effector cells, such as T cells, can be genetically modified following isolation using known methods, or the immune effector cells can be activated and expanded (or differentiated in the case of progenitors) in vitro prior to being genetically modified. In another embodiment, the immune effector cells, such as T cells, are genetically modified with the chimeric antigen receptors described herein (e.g., transduced with a viral vector comprising a nucleic acid encoding a CAR) and then are activated and expanded in vitro. Methods for activating and expanding T cells are known in the art and are described, for example, in U.S. Pat. Nos. 6,905,874; 6,867,041; 6,797,514; WO2012079000. Generally, such methods include contacting PBMC or isolated T cells with a stimulatory agent and costimulatory agent, such as anti-CD3 and anti-CD28 antibodies, generally attached to a bead or other surface, in a culture medium with appropriate cytokines, such as IL-2 (e.g., recombinant human IL-2). Anti-CD3 and anti-CD28 antibodies attached to the same bead serve as a "surrogate" antigen presenting cell (APC). In other embodiments, the T cells may be activated and stimulated to proliferate with feeder cells and appropriate antibodies and cytokines using methods such as those described in U.S. Pat. Nos. 6,040,177; 5,827,642; and WO2012129514.

In some embodiments, the immune effector cells comprise any leukocyte involved in defending the body against infectious disease and foreign materials. For example, the immune effector cells can comprise lymphocytes, monocytes, macrophages, dendritic cells, mast cells, neutrophils, basophils, eosinophils, or any combinations thereof. For example, the immune effector cells can comprise T lymphocytes, preferably cytotoxic T lymphocytes (CTLs).

T helper cells ($T_H$ cells) assist other white blood cells in immunologic processes, including maturation of B cells into plasma cells and memory B cells, and activation of cytotoxic T cells and macrophages. These cells are also known as CD4$^+$ T cells because they express the CD4 glycoprotein on their surface. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. These cells can differentiate into one of several subtypes, including $T_H1$, $T_H2$, $T_H3$, $T_H17$, $T_H9$, or $T_{FH}$, which secrete different cytokines to facilitate a different type of immune response.

Cytotoxic T cells (Tc cells, or CTLs) destroy virally infected cells and tumor cells, and are also implicated in transplant rejection. These cells are also known as CD8$^+$ T cells since they express the CD8 glycoprotein at their surface. These cells recognize their targets by binding to antigen associated with MHC class I molecules, which are present on the surface of all nucleated cells. Through IL-10, adenosine and other molecules secreted by regulatory T cells, the CD8+ cells can be inactivated to an anergic state, which prevents autoimmune diseases.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory cells may be either CD4$^+$ or CD8$^+$. Memory T cells typically express the cell surface protein CD45RO.

Regulatory T cells ($T_{reg}$ cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus. Two major classes of CD4$^+$ $T_{reg}$ cells have been described—naturally occurring $T_{reg}$ cells and adaptive $T_{reg}$ cells.

Natural killer T (NKT) cells (not to be confused with natural killer (NK) cells) bridge the adaptive immune system with the innate immune system. Unlike conventional T cells that recognize peptide antigens presented by major histocompatibility complex (MHC) molecules, NKT cells recognize glycolipid antigen presented by a molecule called CD1d.

In some embodiments, the T cells comprise a mixture of CD4$^+$ cells. In other embodiments, the T cells are enriched for one or more subsets based on cell surface expression. For example, in some cases, the T comprise are cytotoxic CD8$^+$ T lymphocytes.

Natural-killer (NK) cells are CD56$^+$CD3$^-$ large granular lymphocytes that can kill virally infected and transformed cells, and constitute a critical cellular subset of the innate immune system (Godfrey J, et al. Leuk Lymphoma 2012 53:1666-1676). Unlike cytotoxic CD8$^+$ T lymphocytes, NK cells launch cytotoxicity against tumor cells without the requirement for prior sensitization, and can eradicate MHC-I-negative cells (Narni-Mancinelli E, et al. Int Immunol 2011 23:427-431). NK cells are safer effector cells, as they may avoid the potentially lethal complications of cytokine storms (Morgan R A, et al. Mol Ther 2010 18:843-851), tumor lysis syndrome (Porter D L, et al. N Engl J Med 2011 365:725-733), and on-target, off-tumor effects.

Binding Properties of the Chimeric Antigen Receptors

As used herein, the term "binding" in the context of the binding of a chimeric antigen receptor to, e.g., a predetermined antigen, such as a cell surface protein or fragment thereof (or to an antigen bound to a cell surface protein such as an HLA molecule). Binding typically refers to an interaction or association between a minimum of two entities or molecular structures, such as an antigen-binding domain: antigen interaction. For instance, binding affinity typically corresponds to a $K_D$ value of about $10^{-7}$ M or less, such as about $10^{-8}$ M or less, such as about $10^{-9}$ M or less when determined by, for instance, surface plasmon resonance (SPR) technology in a BIAcore 3000 instrument using the antigen as the ligand and the antibody or chimeric antigen receptor as the analyte (or antiligand). Cell-based binding strategies, such as fluorescent-activated cell sorting (FACS) binding assays, are also routinely used, and FACS data correlates well with other methods such as radioligand competition binding and SPR (Benedict, C A, *J Immunol Methods.* 1997, 201 (2): 223-31; Geuijen, C A, et al. *J Immunol Methods.* 2005, 302 (1-2): 68-77).

Accordingly, in some embodiments, a chimeric antigen receptor of the present disclosure binds to the predetermined antigen or cell surface molecule (receptor) having an affinity corresponding to a $K_D$ value that is at least ten-fold lower than its affinity for binding to a non-specific antigen (e.g., BSA, casein). As described herein, a chimeric antigen receptor of the present disclosure can bind to an HLA-presented antigen described herein. According to the present disclosure, in some embodiments, the affinity of a chimeric antigen receptor with a $K_D$ value that is equal to or less than ten-fold lower than a non-specific antigen may be considered non-detectable binding.

The term "$K_D$" (M) refers to the dissociation equilibrium constant of a particular antigen-binding domain:antigen interaction. There is an inverse relationship between $K_D$ and binding affinity, therefore the smaller the $K_D$ value, the higher, i.e. stronger, the affinity. Thus, the terms "higher affinity" or "stronger affinity" relate to a higher ability to form an interaction and therefore a smaller $K_D$ value, and conversely the terms "lower affinity" or "weaker affinity" relate to a lower ability to form an interaction and therefore a larger $K_D$ value. In some circumstances, a higher binding affinity (or $K_D$) of a particular molecule (e.g., a chimeric antigen receptor) to its interactive partner molecule (e.g. antigen X) compared to the binding affinity of the molecule (e.g., chimeric antigen receptor) to another interactive partner molecule (e.g. antigen Y) may be expressed as a binding ratio determined by dividing the larger $K_D$ value (lower, or weaker, affinity) by the smaller $K_D$ (higher, or stronger, affinity), for example expressed as 5-fold or 10-fold greater binding affinity, as the case may be The term "$k_d$" (sec−1 or 1/s) refers to the dissociation rate constant of a particular antigen-binding domain:antigen interaction, or the dissociation rate constant of a chimeric antigen receptor. Said value is also referred to as the $k_{off}$ value.

The term "$k_a$" (M−1×sec−1 or 1/M) refers to the association rate constant of a particular antigen-binding domain:antigen interaction, or the association rate constant of a chimeric antigen receptor.

The term "$K_A$" (M−1 or 1/M) refers to the association equilibrium constant of a particular antigen-binding domain:antigen interaction, or the association equilibrium constant of a chimeric antigen receptor. The association equilibrium constant is obtained by dividing the $k_a$ by the $k_d$.

The term "EC50" or "$EC_{50}$" refers to the half maximal effective concentration, which includes the concentration of a chimeric antigen receptor that induces a response halfway between the baseline and maximum after a specified exposure time. The $EC_{50}$ essentially represents the concentration of a chimeric antigen receptor where 50% of its maximal effect is observed. In certain embodiments, the $EC_{50}$ value equals the concentration of a chimeric antigen receptor of the present disclosure that gives half-maximal binding to cells expressing an antigen (e.g., a tumor-associated antigen), as determined by e.g. a FACS binding assay. Thus, reduced or weaker binding is observed with an increased $EC_{50}$, or half maximal effective concentration value.

In one embodiment, decreased binding can be defined as an increased $EC_{50}$ chimeric antigen receptor concentration that enables binding to the half-maximal amount of target cells.

The present disclosure provides chimeric antigen receptors with antigen-binding domains derived from antibodies that bind a human antigen with high affinity (e.g., nanomolar or sub-nanomolar $K_D$ values).

According to certain embodiments, the present disclosure provides chimeric antigen receptors with antigen-binding domains derived from corresponding antibodies that bind human antigen (e.g., at 25° C.) with a $K_D$ of less than about 5 nM as measured by surface plasmon resonance. In certain embodiments, the corresponding antibodies bind an antigenic protein with a $K_D$ of less than about 20 nM, less than about 10 nM, less than about 8 nM, less than about 7 nM, less than about 6 nM, less than about 5 nM, less than about 4 nM, less than about 3 nM, less than about 2 nM, less than about 1 nM, less than about 800 pM, less than about 700 pM, less than about 500 pM, less than about 400 pM, less than about 300 pM, less than about 200 pM, less than about 100 pM, less than about 50 pM, or less than about 25 pM as measured by surface plasmon resonance.

The present disclosure also provides chimeric antigen receptors with antigen-binding domains derived from corresponding antibodies that bind the antigenic protein with a dissociative half-life (t½) of greater than about 10 minutes or greater than about 125 minutes as measured by surface plasmon resonance at 25° C. In certain embodiments, the corresponding antibodies bind the antigenic protein with a t½ of greater than about 3 minutes, greater than about 4 minutes, greater than about 10 minutes, greater than about 20 minutes, greater than about 30 minutes, greater than about 40 minutes, greater than about 50 minutes, greater than about 60 minutes, greater than about 70 minutes, greater than about 80 minutes, greater than about 90 minutes, greater than about 100 minutes, greater than about 110 minutes, or greater than about 120 minutes, as measured by surface plasmon resonance at 25° C.

The present disclosure also provides chimeric antigen receptors with antigen-binding domains derived from corresponding antibodies that bind specifically to human cell lines which express endogenous MAGE-A4, as determined by a FACS binding assay.

Therapeutic Methods

Immune effector cells expressing the CARs disclosed herein elicit a therapeutically beneficial immune response against PIG or low density antigen-expressing cancer cells. For example, an anti-tumor immune response elicited by the disclosed CAR-modified immune effector cells may be an active or a passive immune response. In addition, the CAR-mediated immune response may be part of an adoptive immunotherapy approach in which CAR-modified immune effector cells induce an immune response specific to PIG or low density cancer antigen.

CAR-expressing immune effector cells prepared as described herein can be utilized in methods and compositions for adoptive immunotherapy in accordance with known techniques, or variations thereof that will be apparent to those skilled in the art based on the instant disclosure. See, e.g., US Patent Application Publication No. 2003/0170238 to Gruenberg et al; see also U.S. Pat. No. 4,690,915 to Rosenberg.

In some aspects, provided herein are methods of treating cancer (e.g., a solid tumor) in a subject by administering to the subject a composition comprising cells expressing a CAR polypeptide disclosed herein. In some embodiments, the methods provided herein further comprise conjointly administering to the subject a composition comprising cell that express a second CAR polypeptide comprising a 4-1BB domain in the costimulatory region of the CAR polypeptide. In some embodiments, the second CAR comprises at least one intracytoplasmic signaling region comprising a cluster of differentiation 3 zeta (CD3/ζ) domain. In some embodiments, the second CAR comprises an extracellular domain specific for a low density cancer antigen and/or a peptide in groove cancer antigen. The second CAR polypeptide may comprise a cluster of differentiation 8 alpha (CD8/α) peptide in the hinge/transmembrane region. Without being bound by theory, the immune cells expressing the first CAR (i.e., a CAR polypeptide comprising a CD28/ζ domain in the co-stimulatory domain of the CAR) provides an initial burst to facilitate rapid killing of cancer cells, while the administration of immune cell by the 4-1BB provides sustained cancer cell killing, albeit at a lower level of killing when compared to administration of immune cells expressing the first CAR. 4-1BB/CD3z CAR is associated with persistence of CAR T cells in patients, which will in turn provide sustained cancer cell killing.

In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin.

A treatment-effective amount of cells in the composition is at least 2 cells (for example, at least 1 CD8+ central memory T cell and at least 1 CD4+ helper T cell subset) or is more typically greater than 102 cells, and up to 106 up to and including 108 or 109 cells and can be more than 1010 cells. The number of cells will depend upon the ultimate use for which the composition is intended as will the type of cells included therein.

The cells may be autologous or heterologous to the patient undergoing therapy. The cells may be allogenic. If desired, the treatment may also include administration of mitogens (e.g., PHA) or lymphokines, cytokines, and/or chemokines (e.g., IFN-γ, IL-2, IL-12, TNF-α, IL-18, and TNF-β, GM-CSF, IL-4, IL-13, Flt3-L, RANTES, MIP1α, etc.) as described herein to enhance induction of the immune response.

The CAR expressing immune effector cell populations may be administered either alone, or as a pharmaceutical composition in combination with diluents and/or with other components such as IL-2 or other cytokines or cell populations. Pharmaceutical compositions disclosed herein may comprise a CAR-expressing immune effector cell population, such as T cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions disclosed herein may be formulated for intravenous administration.

The anti-tumor immune response induced in a subject by administering CAR expressing T cells described herein using the methods described herein, or other methods known in the art, may include cellular immune responses mediated by cytotoxic T cells capable of killing infected cells, regulatory T cells, and helper T cell responses. Humoral immune responses, mediated primarily by helper T cells capable of activating B cells thus leading to antibody production, may also be induced. A variety of techniques may be used for analyzing the type of immune responses induced by the compositions disclosed herein, which are well described in the art; e.g., Current Protocols in Immunology, Edited by: John E. Coligan, Ada M. Kruisbeek, David H. Margulies, Ethan M. Shevach, Warren Strober (2001) John Wiley & Sons, N.Y., N.Y.

Thus, provided herein are methods of treating an individual diagnosed with or suspected of having, or at risk of developing a malignancy, comprising administering to the individual a therapeutically effective amount of the CAR-expressing immune effector cells as described herein.

The administration of the disclosed compositions may be carried out in any convenient manner, including by injection, transfusion, or implantation. The compositions described herein may be administered to a patient subcutaneously, intradermally, intratumorally, intranodally, intramedullary, intramuscularly, by intravenous (i.v.) injection, or intraperitoneally. In some embodiments, the disclosed compositions are administered to a patient by intradermal or subcutaneous injection. In some embodiments, the disclosed compositions are administered by i.v. injection. The compositions may also be injected directly into a tumor, lymph node, or site of infection.

Provided herein are methods of conjointly administering to the subject a second CAR polypeptide comprising a 4-1BB domain in the costimulatory region of the CAR polypeptide. The second CAR polypeptide may further comprise at least one intracytoplasmic signaling region comprising a cluster of differentiation 3 zeta (CD3/ζ) domain and/or an extracellular domain specific for a low density cancer antigen and/or a peptide in groove cancer antigen. The second CAR polypeptide may comprise a cluster of differentiation 8 alpha (CD8/α) peptide in the hinge/transmembrane region.

In certain embodiments, the disclosed CAR-modified immune effector cells are administered to a patient in conjunction with (e.g., before, simultaneously or following) any number of relevant treatment modalities, including but not limited to additional cancer treatments. In some embodiments, the CAR-modified immune effector cells may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. In some embodiments, the CAR-modified immune effector cells are administered to a patient in conjunction with (e.g., before, simultaneously or following) bone marrow transplantation, T-cell ablative therapy using either chemotherapy agents such as, fludarabine, external-beam radiation therapy (XRT), cyclophosphamide, or antibodies such as OKT3 or CAM-PATH. In other embodiments, the cell compositions are administered following B-cell ablative therapy such as agents that react with CD20, e.g., Rituxan. For example, in some embodiments, subjects may undergo standard treatment with high dose chemotherapy followed by peripheral blood stem cell transplantation. In certain embodiments, following the transplant, subjects receive an infusion of the expanded immune cells. In additional embodiments, expanded cells are administered before or following surgery to treat cancer or pre-cancerous lesions in the subject.

Administration Regimens

According to certain embodiments of the present disclosure, multiple doses of the engineered cells may be administered to a subject over a defined time course. The methods according to this aspect comprise sequentially administering to a subject multiple doses of the cells. As used herein, "sequentially administering" means that each dose is administered to the subject at a different point in time, e.g., on different days separated by a predetermined interval (e.g., hours, days, weeks or months). The present disclosure provides methods which comprise sequentially administering to the patient a single initial dose, followed by one or more secondary doses, and optionally followed by one or more tertiary doses.

The terms "initial dose," "secondary doses," and "tertiary doses," refer to the temporal sequence of administration of the engineered cells of the present disclosure. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of engineered cells, but generally may differ from one another in terms of frequency of administration. In certain embodiments, however, the amount of engineered cells contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In one embodiment of the present disclosure, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 174/2, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose which is administered to a patient prior to the administration of the very next dose in the sequence with no intervening doses.

The methods according to this aspect of the present disclosure may comprise administering to a patient any number of secondary and/or tertiary doses. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

Indications

In certain aspects, provided herein are methods of treating cancer using a CAR T cell provided herein. In certain embodiments, the cancer to be treated expresses a PIG antigen and/or a low density antigen to which the CAR expressed by the T cells specifically binds.

In some embodiments, cancers that may be treated by methods and compositions provided herein include, but are not limited to, cancer cells from the cervix, anus, vagina, vulva, penis, tongue base, larynx, tonsil, bladder, blood, bone, bone marrow, brain, breast, colon, esophagus, gastrointestine, gum, head, kidney, liver, lung, nasopharynx, neck, ovary, prostate, skin, non-melanoma skin cancer (NMSC), cutaneous squamous cell carcinoma (SCC), stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometrioid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; mammary paget's disease; acinar cell carcinoma; adenosquamous carcinoma; adenocarcinoma w/squamous metaplasia; malignant thymoma; malignant ovarian stromal tumor; malignant thecoma; malignant granulosa cell tumor; and malignant roblastoma; sertoli cell carcinoma; malignant leydig cell tumor; malignant lipid cell tumor; malignant paraganglioma; malignant extra-mammary paraganglioma; pheochromocytoma; glomangiosarcoma; malignant melanoma; amelanotic melanoma; superficial spreading melanoma; malignant melanoma in giant pigmented nevus; epithelioid cell melanoma; malignant blue nevus; sarcoma; fibrosarcoma; malignant fibrous histiocytoma; myxosarcoma; liposarcoma; leiomyosarcoma; rhabdomyosarcoma; embryonal rhabdomyosarcoma; alveolar rhabdomyosarcoma; stromal sarcoma; malignant mixed tumor; mullerian mixed tumor; nephroblastoma; hepatoblastoma; carcinosarcoma; malignant mesenchymoma; malignant brenner tumor; malignant phyllodes tumor; synovial sarcoma; malignant mesothelioma; dysgerminoma; embryonal carcinoma; malignant teratoma; malignant struma ovarii; choriocarcinoma; malignant mesonephroma; hemangiosarcoma; malignant hemangioendothelioma; kaposi's sarcoma; malignant hemangiopericytoma; lymphangiosarcoma; osteosarcoma; juxtacortical osteosarcoma; chondrosarcoma; malignant chondroblastoma; mesenchymal chondrosarcoma; giant cell tumor of bone; ewing's sarcoma; malignant odontogenic tumor; ameloblastic odontosarcoma; malignant ameloblastoma; ameloblastic fibrosarcoma; malignant pinealoma; chordoma; malignant glioma; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; malignant meningioma; neurofibrosarcoma; malignant neurilemmoma; malignant granular cell tumor; malignant lymphoma; Hodgkin's disease; Hodgkin's lymphoma; paragranuloma; small lymphocytic malignant lymphoma; diffuse large cell malignant lymphoma; follicular malignant lymphoma; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In certain embodiments, the disclosed CAR-T cells can be used in combination with any compound, moiety or group that has a cytotoxic or cytostatic effect. Drug moieties include chemotherapeutic agents, which may function as microtubulin inhibitors, mitosis inhibitors, topoisomerase inhibitors, or DNA intercalators, and particularly those which are used for cancer therapy. Exemplary anti-cancer compounds include, but are not limited to, Alemtuzumab (Campath®), Alitretinoin (Panretin®), Anastrozole (Arimidex®), Bevacizumab (Avastin®), Bexarotene (Targretin®), Bortezomib (Velcade®), Bosutinib (Bosulif®), Brentuximab vedotin (Adcetris®), Cabozantinib (Cometriq™), Carfilzomib (Kyprolis™), Cetuximab (Erbitux®), Crizotinib (Xalkori®), Dasatinib (Sprycel®), Denileukin diftitox (Ontak®), Erlotinib hydrochloride (Tarceva®), Everolimus (Afinitor®), Exemestane (Aromasin®), Fulvestrant (Faslodex®), Gefitinib (Iressa®), Ibritumomab tiuxetan (Zevalin®), Imatinib mesylate (Gleevec®), Ipilimumab (Yervoy™), Lapatinib ditosylate (Tykerb®), Letrozole (Femara®), Nilotinib (Tasigna®), Ofatumumab (Arzerra®), Panitumumab (Vectibix®), Pazopanib hydrochloride (Votrient®), Pertuzumab (Perjeta™), Pralatrexate (Folotyn®), Regorafenib (Stivarga®), Rituximab (Rituxan®), Romidepsin (Istodax®), Sorafenib tosylate (Nexavar®), Sunitinib malate (Sutent®), Tamoxifen, Temsirolimus (Torisel®), Toremifene (Fareston®), Tositumomab and 131I-tositumomab (Bexxar®), Trastuzumab (Herceptin®), Tretinoin (Vesanoid®), Vandetanib (Caprelsa®), Vemurafenib (Zelboraf®), Vorinostat (Zolinza®), and Ziv-aflibercept (Zaltrap®). Examples of further chemotherapeutic agents include Examples of such chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimustine; antibiotics such as the enediyne antibiotics (e.g., calicheamicin, especially calicheamicin gammaI1 and calicheamicin omegaI1; dynemicin, including dynemicin A; bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; and pharmaceutically acceptable salts, acids or derivatives of any of the above.

In some embodiments, the subject is also administered an additional immunotherapeutic agent. Immunotherapy refers to a treatment that uses a subject's immune system to treat cancer, e.g., cancer vaccines, cytokines, use of cancer-specific antibodies, T cell therapy, and dendritic cell therapy.

In some embodiments, the subject is also administered an immune modulatory protein. Examples of immune modulatory proteins include, but are not limited to, B lymphocyte chemoattractant ("BLC"), C-C motif chemokine 11 ("Eotaxin-1"), Eosinophil chemotactic protein 2 ("Eotaxin-2"), Granulocyte colony-stimulating factor ("G-CSF"), Granulocyte macrophage colony-stimulating factor ("GM-CSF"), 1-309, Intercellular Adhesion Molecule 1 ("ICAM-1"), Interferon gamma ("IFN-gamma"), Interleukin-1 alpha ("IL-1 alpha"), Interleukin-1 beta ("IL-1 beta"), Interleukin 1 receptor antagonist ("IL-1 ra"), Interleukin-2 ("IL-2"), Interleukin-4 ("IL-4"), Interleukin-5 ("IL-5"), Interleukin-6 ("IL-6"), Interleukin-6 soluble receptor ("IL-6 sR"), Interleukin-7 ("IL-7"), Interleukin-8 ("IL-8"), Interleukin-10 ("IL-10"), Interleukin-11 ("IL-11"), Subunit beta of Interleukin-12 ("IL-12 p40" or "IL-12 p70"), Interleukin-13 ("IL-13"), Interleukin-15 ("IL-15"), Interleukin-16 ("IL-16"), Interleukin-17 ("IL-17"), Chemokine (C-C motif) Ligand 2 ("MCP-1"), Macrophage colony-stimulating factor ("M-CSF"), Monokine induced by gamma interferon ("MIG"), Chemokine (C-C motif) ligand 2 ("MIP-1 alpha"), Chemokine (C-C motif) ligand 4 ("MIP-1 beta"), Macrophase inflammatory protein-1-delta ("MIP-1 delta"), Platelet-derived growth factor subunit B ("PDGF-BB"), Chemokine (C-C motif) ligand 5, Regulated on Activation, Normal T cell Expressed and Secreted ("RANTES"), TIMP metallopeptidase inhibitor 1 ("TIMP-1"), TIMP metallopeptidase inhibitor 2 ("TIMP-2"), Tumor necrosis factor, lymphotoxin-alpha ("TNF alpha"), Tumor necrosis factor, lymphotoxin-beta ("TNF beta"), Soluble TNF receptor type 1 ("sTNFRI"), STNFRIIAR, Brain-derived neurotrophic factor ("BDNF"), Basic fibroblast growth factor ("bFGF"), Bone morphogenetic protein 4 ("BMP-4"), Bone morphogenetic protein 5 ("BMP-5"), Bone morphogenetic protein 7 ("BMP-7"), Nerve growth factor ("b-NGF"), Epidermal growth factor ("EGF"), Epidermal growth factor receptor ("EGFR"), Endocrine-gland-derived vascular endothelial growth factor ("EG-VEGF"), Fibroblast growth factor 4 ("FGF-4"), Keratinocyte growth factor ("FGF-7"), Growth differentiation factor 15 ("GDF-15"), Glial cell-derived neurotrophic factor ("GDNF"), Growth Hormone, Heparin-binding EGF-like growth factor ("HB-EGF"), Hepatocyte growth factor ("HGF"), Insulin-like growth factor binding protein 1 ("IGFBP-1"), Insulin-like growth factor binding protein 2 ("IGFBP-2"), Insulin-like growth factor binding protein 3 ("IGFBP-3"), Insulin-like growth factor binding protein 4 ("IGFBP-4"), Insulin-like growth factor binding protein 6 ("IGFBP-6"), Insulin-like growth factor 1 ("IGF-1"), Insulin, Macrophage colony-stimulating factor ("M-CSF R"), Nerve growth factor receptor ("NGF R"), Neurotrophin-3 ("NT-3"), Neurotrophin-4 ("NT-4"), Osteoclastogenesis inhibitory factor ("Osteoprotegerin"), Platelet-derived growth factor receptors ("PDGF-AA"), Phosphatidylinositol-glycan biosynthesis ("PIGF"), Skp, Cullin, F-box containing complex ("SCF"), Stem cell factor receptor ("SCF R"), Transforming growth factor alpha ("TGFalpha"), Transforming growth factor beta-1 ("TGF beta 1"), Transforming growth factor beta-3 ("TGF beta 3"), Vascular endothelial growth factor ("VEGF"), Vascular endothelial growth factor receptor 2 ("VEGFR2"), Vascular endothelial growth factor receptor 3 ("VEGFR3"), VEGF-D 6Ckine, Tyrosine-protein kinase receptor UFO ("Axl"), Betacellulin ("BTC"), Mucosae-associated epithelial chemokine ("CCL28"), Chemokine (C-C motif) ligand 27 ("CTACK"), Chemokine (C-X-C motif) ligand 16 ("CXCL16"), C-X-C motif chemokine 5 ("ENA-78"), Chemokine (C-C motif) ligand 26 ("Eotaxin-3"), Granulocyte chemotactic protein 2 ("GCP-2"), GRO, Chemokine (C-C motif) ligand 14 ("HCC-1"), Chemokine (C-C motif) ligand 16 ("HCC-4"), Interleukin-9 ("IL-9"), Interleukin-17F ("IL-17F"), Interleukin-18-binding protein ("IL-18 BPa"), Interleukin-28 A ("IL-28A"), Interleukin 29 ("IL-29"), Interleukin 31 ("IL-31"), C-X-C motif chemokine 10 ("IP-10"), Chemokine receptor CXCR3 ("I-TAC"), Leukemia inhibitory factor ("LIF"), Light, Chemokine (C motif) ligand ("Lymphotactin"), Monocyte chemoattractant protein 2 ("MCP-2"), Monocyte chemoattractant protein 3 ("MCP-3"), Monocyte chemoattractant protein 4 ("MCP-4"), Macrophage-derived chemokine ("MDC"), Macrophage migration inhibitory factor ("MIF"), Chemokine (C-C motif) ligand 20 ("MIP-3 alpha"), C-C motif chemokine 19 ("MIP-3 beta"), Chemokine (C-C motif) ligand 23 ("MPIF-1"), Macrophage stimulating protein alpha chain ("MSPalpha"), Nucleosome assembly protein 1-like 4 ("NAP-2"), Secreted phosphoprotein 1 ("Osteopontin"), Pulmonary and activation-regulated cytokine ("PARC"), Platelet factor 4 ("PF4"), Stroma cell-derived factor-1 alpha ("SDF-1 alpha"), Chemokine (C-C motif) ligand 17 ("TARC"), Thymus-expressed chemokine ("TECK"), Thymic stromal lymphopoietin ("TSLP 4-IBB"), CD 166 antigen ("ALCAM"), Cluster of Differentiation 80 ("B7-1"), Tumor necrosis factor receptor superfamily member 17 ("BCMA"), Cluster of Differentiation 14 ("CD14"), Cluster of Differentiation 30 ("CD30"), Cluster of Differentiation 40 ("CD40 Ligand"), Carcinoembryonic antigen-related cell adhesion molecule 1 (biliary glycoprotein) ("CEACAM-1"), Death Receptor 6 ("DR6"), Deoxythymidine kinase ("Dtk"), Type 1 membrane glycoprotein ("Endoglin"), Receptor tyrosine-protein kinase erbB-3 ("ErbB3"), Endothelial-leukocyte adhesion molecule 1 ("E-Selectin"), Apoptosis antigen 1 ("Fas"), Fms-like tyrosine kinase 3 ("Flt-3L"), Tumor necrosis factor receptor superfamily member 1 ("GITR"), Tumor necrosis factor receptor superfamily member 14 ("HVEM"), Intercellular adhesion molecule 3 ("ICAM-3"), IL-1 R4, IL-1 RI, IL-10 Rbeta, IL-17R, IL-2Rgamma, IL-21R, Lysosome membrane protein 2 ("LIMPII"), Neutrophil gelatinase-associated lipocalin ("Lipocalin-2"), CD62L ("L-Selectin"), Lymphatic endothelium ("LYVE-1"), MHC class I polypeptide-related sequence A ("MICA"), MHC class I polypeptide-related sequence B ("MICB"), NRGl-betal, Beta-type platelet-derived growth factor receptor ("PDGF Rbeta"), Platelet endothelial cell adhesion molecule ("PECAM-1"), RAGE, Hepatitis A virus cellular receptor 1 ("TIM-1"), Tumor necrosis factor receptor superfamily member IOC ("TRAIL R3"), Trappin protein transglutaminase binding domain ("Trappin-2"), Urokinase receptor ("uPAR"), Vascular cell adhesion protein 1 ("VCAM-1"), XEDAR, Activin A, Agouti-related protein ("AgRP"), Ribonuclease 5 ("Angiogenin"), Angiopoietin 1, Angiostatin, Cathepsin S, CD40, Cryptic family protein IB ("Cripto-1"), DAN, Dickkopf-related protein 1 ("DKK-1"), E-Cadherin, Epithelial cell adhesion molecule ("EpCAM"), Fas Ligand (FasL or CD95L), Fcg RIIB/C, FoUistatin, Galectin-7, Intercellular adhesion molecule 2 ("ICAM-2"), IL-13 RI, IL-13R2, IL-17B, IL-2 Ra, IL-2 Rb, IL-23, LAP, Neuronal cell adhesion molecule ("NrCAM"), Plasminogen activator inhibitor-1 ("PAI-1"), Platelet derived growth factor receptors ("PDGF-AB"), Resistin, stromal cell-derived factor 1 ("SDF-1 beta"), sgp130, Secreted frizzled-related protein 2 ("ShhN"), Sialic acid-binding immunoglobulin-type lectins ("Siglec-5"), ST2, Transforming growth factor-beta 2 ("TGF beta 2"), Tie-2, Thrombopoietin ("TPO"), Tumor necrosis factor receptor superfamily member 10D ("TRAIL R4"), Triggering receptor expressed on myeloid cells 1 ("TREM- 1"), Vascular endothelial growth factor C ("VEGF-C"), VEGFR1, Adiponectin, Adipsin ("AND"), Alpha-fetoprotein ("AFP"), Angiopoietin-like 4 ("ANGPTL4"), Beta-2-microglobulin ("B2M"), Basal cell adhesion molecule ("BCAM"), Carbohydrate antigen 125 ("CA125"), Cancer Antigen 15-3 ("CA15-3"), Carcinoembryonic antigen ("CEA"), cAMP receptor protein ("CRP"), Human Epidermal Growth Factor Receptor 2 ("ErbB2"), Follistatin, Follicle-stimulating hormone ("FSH"), Chemokine (C-X-C motif) ligand 1 ("GRO alpha"), human chorionic gonadotropin ("beta HCG"), Insulin-like growth factor 1 receptor ("IGF-1 sR"), IL-1 sRII, IL-3, IL-18 Rb, IL-21, Leptin, Matrix metalloproteinase-1 ("MMP-1"), Matrix metalloproteinase-2 ("MMP-2"), Matrix metalloproteinase-3 ("MMP-3"), Matrix metalloproteinase-8 ("MMP-8"), Matrix metalloproteinase-9 ("MMP-9"), Matrix metalloproteinase-10 ("MMP-10"), Matrix metalloproteinase-13 ("MMP-13"), Neural Cell Adhesion Molecule ("NCAM-1"), Entactin ("Nidogen-1"), Neuron specific enolase ("NSE"), Oncostatin M ("OSM"), Procalcitonin, Prolactin, Prostate specific antigen ("PSA"), Sialic acid-binding Ig-like lectin 9 ("Siglec-9"), ADAM 17 endopeptidase ("TACE"), Thyroglobulin, Metalloproteinase inhibitor 4 ("TIMP-4"), TSH2B4, Disintegrin and metalloproteinase domain-containing protein 9 ("ADAM-9"), Angiopoietin 2, Tumor necrosis factor ligand superfamily member 13/Acidic leucine-rich nuclear phosphoprotein 32 family member B ("APRIL"), Bone morphogenetic protein 2 ("BMP-2"), Bone morphogenetic protein 9 ("BMP-9"), Complement component 5a ("C5a"), Cathepsin L, CD200, CD97, Chemerin, Tumor necrosis factor receptor superfamily member 6B ("DcR3"), Fatty acid-binding protein 2 ("FABP2"), Fibroblast activation protein, alpha ("FAP"), Fibroblast growth factor 19 ("FGF-19"), Galectin-3, Hepatocyte growth factor receptor ("HGF R"), IFN-alpha/beta R2, Insulin-like growth factor 2 ("IGF-2"), Insulin-like growth factor 2 receptor ("IGF-2 R"), Interleukin-1 receptor 6 ("IL-1R6"), Interleukin 24 ("IL-24"), Interleukin 33 ("IL-33", Kallikrein 14, Asparaginyl endopeptidase ("Legumain"), Oxidized low-density lipoprotein receptor 1 ("LOX-1"), Mannose-binding lectin ("MBL"), Neprilysin ("NEP"), Notch homolog 1, translocation-associated (*Drosophila*) ("Notch-1"), Nephroblastoma overexpressed ("NOV"), Osteoactivin, Programmed cell death protein 1 ("PD-1"), N-acetylmuramoyl-L-alanine amidase ("PGRP-5"), Serpin A4, Secreted frizzled related protein 3 ("sFRP-3"), Thrombomodulin, Toll-like receptor 2 ("TLR2"), Tumor necrosis factor receptor superfamily member 10A ("TRAIL RI"), Transferrin ("TRF"), WIF-1ACE-2, Albumin, AMICA, Angiopoietin 4, B-cell activating factor ("BAFF"), Carbohydrate antigen 19-9 ("CA19-9"), CD 163, Clusterin, CRT AM, Chemokine (C-X-C motif) ligand 14 ("CXCL14"), Cystatin C, Decorin ("DCN"), Dickkopf-related protein 3 ("Dkk-3"), Delta-like protein 1 ("DLL1"), Fetuin A, Heparin-binding growth factor 1 ("aFGF"), Folate receptor alpha ("FOLR1"), Furin, GPCR-associated sorting protein 1 ("GASP-1"), GPCR-associated sorting protein 2 ("GASP-2"), Granulocyte colony-stimulating factor receptor ("GCSF R"), Serine protease hepsin ("HAI-2"), Interleukin-17B Receptor ("IL-17B R"), Interleukin 27 ("IL-27"), Lymphocyte-activation gene 3 ("LAG-3"), Apolipoprotein A-V ("LDL R"), Pepsinogen I, Retinol binding protein 4 ("RBP4"), SOST, Heparan sulfate proteoglycan ("Syndecan-1"), Tumor necrosis factor receptor superfamily member 13B ("TACI"), Tissue factor pathway inhibitor ("TFPI"), TSP-1, Tumor necrosis factor receptor superfamily, member 10b ("TRAIL R2"), TRANCE, Troponin I, Urokinase Plasminogen Activator ("uPA"), Cadherin 5, type 2 or VE-cadherin (vascular endothelial) also known as CD144 ("VE-Cadherin"), WNT1-inducible-signaling pathway protein 1 ("WISP-1"), and Receptor Activator of Nuclear Factor κ B ("RANK").

The disclosed CARs and immune cells expressing CARs can be used in combination with an immune checkpoint inhibitor. Immune Checkpoint inhibition broadly refers to inhibiting the checkpoints that cancer cells can produce to prevent or downregulate an immune response. Two known immune checkpoint pathways involve signaling through the cytotoxic T-lymphocyte antigen-4 (CTLA-4) and programmed-death 1 (PD-1) receptors. These proteins are members of the CD28-B7 family of co-signaling molecules that play important roles throughout all stages of T cell function. The PD-1 receptor (also known as CD279) is expressed on the surface of activated T cells. Its ligands, PD-L1 (B7-H1; CD274) and PD-L2 (B7-DC; CD273), are expressed on the surface of APCs such as dendritic cells or macrophages. PD-L1 is the predominant ligand, while PD-L2 has a much more restricted expression pattern. When the ligands bind to PD-1, an inhibitory signal is transmitted into the T cell, which reduces cytokine production and suppresses T cell proliferation. Checkpoint inhibitors include, but are not limited to aptamers and antibodies that block PD-1 (Nivolumab (BMS-936558 or MDX1106), CT-011, MK-3475, AMP-514), PD-L1 (MDX-1105 (BMS-936559), MPDL3280A, MSB0010718C), PD-L2 (rHIgM12B7, AMP-224), CTLA-4 (Ipilimumab (MDX-010), Tremelimumab (CP-675,206)), IDO, B7-H3 (MGA271), B7-H4, TIM3, LAG-3 (BMS-986016). The immune checkpoint inhibitor may be cemiplimab (REGN2810), nivolumab (BMS-936558, MDX-1106, ONO-4538), pembrolizumab (MK-3475, SCH 900475), atezolizumab (MPDL3280A, RG7446, RO5541267), durvalumab (MEDI4736, MEDI-4736), avelumab (MSB0010718C), ipilimumab (BMS-734016, IBI310, MDX-010), SHR1210, sintilimab (IBI308), spartalizumab (PDR001), tislelizumab (BGB-A317), pidilizumab, BCD-100, toripalimab (JS001), BAY 1905254, ASP 8374, PF-06801591, AMP-224, AB122, AK105, AMG 404, BCD-100, BI 754091, F520, HLX10, HX008, JTX-4014, LZM009, MEDI0680, MGA012, Sym021, TSR-042, PSB205, MGD019, MGD013, AK104, XmAb20717, RO7121661, CX-188, INCB086550, FS118, BCD-135, BGB-A333, CBT-502, CK-301, CS1001, FAZ053, HLX20, KN035, MDX-1105, MSB2311, SHR-1316, TG-1501, ZKAB001, INBRX-105, MCLA-145, KN046, M7824, LY3415244, INCB086550, CA-170, CX-072, ADU-1604, AGEN1181, AGEN1884, MK-1308, REGN4659, XmAb22841, ATOR-1015, PSB205, MGD019, AK104, XmAb20717, BMS-986249, tremelimumab, BMS-986258, BGB-A425, INCAGN02390, Sym023, JNJ 61610588, BI 754111, LAG525, MK-4280, REGN3767, Sym022, TSR-033, relatlimab, JTX-2011, MGD009, BMS-986207, OMP-313M32, MK-7684 or TSR-022.

Human monoclonal antibodies to programmed death 1 (PD-1) and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

In some embodiments, the PD-L1 inhibitor comprises an antibody that specifically binds PDL1, such as BMS-936559 (Bristol-Myers Squibb) or MPDL3280A (Roche). In some embodiments, the PD-1 inhibitor comprises an antibody that specifically binds PD-1, such as lambrolizumab (Merck), nivolumab (Bristol-Myers Squibb), or MEDI4736 (Astra-Zeneca). Human monoclonal antibodies to PD-1 and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

Generating optimal "killer" CD8 T cell responses also requires T cell receptor activation plus co-stimulation, which can be provided through ligation of tumor necrosis factor receptor family members, including OX40 (CD134) and 4-1BB (CD137). OX40 is of particular interest as treatment with an activating (agonist) anti-OX40 mAb augments T cell differentiation and cytolytic function leading to enhanced anti-tumor immunity against a variety of tumors.

In some embodiments, such an additional therapeutic agent may be selected from an antimetabolite, such as methotrexate, 6-mercaptopurine, 6-thioguanine, cytarabine, fludarabine, 5-fluorouracil, decarbazine, hydroxyurea, asparaginase, gemcitabine or cladribine.

In some embodiments, such an additional therapeutic agent may be selected from an alkylating agent, such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin.

In some embodiments, such an additional therapeutic agent may be selected from an anti-mitotic agent, such as taxanes, for instance docetaxel, and paclitaxel, and *vinca* alkaloids, for instance vindesine, vincristine, vinblastine, and vinorelbine.

In some embodiments, such an additional therapeutic agent may be selected from a topoisomerase inhibitor, such as topotecan or irinotecan, or a cytostatic drug, such as etoposide and teniposide.

In some embodiments, such an additional therapeutic agent may be selected from a growth factor inhibitor, such as an inhibitor of ErbB1 (EGFR) (such as an EGFR antibody, e.g. zalutumumab, cetuximab, panitumumab or nimotuzumab or other EGFR inhibitors, such as gefitinib or erlotinib), another inhibitor of ErbB2 (HER2/neu) (such as a HER2 antibody, e.g. trastuzumab, trastuzumab-DM 1 or pertuzumab) or an inhibitor of both EGFR and HER2, such as lapatinib).

In some embodiments, such an additional therapeutic agent may be selected from a tyrosine kinase inhibitor, such as imatinib (Glivec, Gleevec STI571) or lapatinib.

Therefore, in some embodiments, a disclosed antibody is used in combination with ofatumumab, zanolimumab, daratumumab, ranibizumab, nimotuzumab, panitumumab, hu806, daclizumab (Zenapax), basiliximab (Simulect), infliximab (Remicade), adalimumab (Humira), natalizumab (Tysabri), omalizumab (Xolair), efalizumab (Raptiva), and/or rituximab.

In some embodiments, a therapeutic agent for use in combination with CARs (e.g., the CARs disclosed herein and immune cells expressing such CARs) for treating the disorders as described above may be an anti-cancer cytokine, chemokine, or combination thereof. Examples of suitable cytokines and growth factors include IFNy, IL-2, IL-4, IL-6, IL-7, IL-10, IL-12, IL-13, IL-15, IL-18, IL-23, IL-24, IL-27, IL-28a, IL-28b, IL-29, KGF, IFNa (e.g., INFa2b), IFN, GM-CSF, CD40L, Flt3 ligand, stem cell factor, ancestim, and TNFa. Suitable chemokines may include Glu-Leu-Arg (ELR)-negative chemokines such as IP-10, MCP-3, MIG, and SDF-la from the human CXC and C-C chemokine families. Suitable cytokines include cytokine derivatives, cytokine variants, cytokine fragments, and cytokine fusion proteins.

In some embodiments, a therapeutic agent for use in combination with a CARs for treating the disorders as described above may be a cell cycle control/apoptosis regulator (or ""regulating agent""). A cell cycle control/apoptosis regulator may include molecules that target and modulate cell cycle control/apoptosis regulators such as (i) cdc-25 (such as NSC 663284), (ii) cyclin-dependent kinases that overstimulate the cell cycle (such as flavopiridol (L868275, HMR1275), 7-hydroxystaurosporine (UCN-01, KW-2401), and roscovitine (R-roscovitine, CYC202)), and (iii) telomerase modulators (such as BIBR1532, SOT-095, GRN163 and compositions described in for instance U.S. Pat. Nos. 6,440,735 and 6,713,055). Non-limiting examples of molecules that interfere with apoptotic pathways include TNF-related apoptosis-inducing ligand (TRAIL)/apoptosis-2 ligand (Apo-2L), antibodies that activate TRAIL receptors, IFNs, and antisense Bc1-2.

In some embodiments, a therapeutic agent for use in combination with CARs (e.g., the CARs disclosed herein and immune cells expressing such CARs) for treating the disorders as described above may be a hormonal regulating agent, such as agents useful for anti-androgen and anti-estrogen therapy. Examples of such hormonal regulating agents are tamoxifen, idoxifene, fulvestrant, droloxifene, toremifene, raloxifene, diethylstilbestrol, ethinyl estradiol/estinyl, an antiandrogene (such as flutaminde/eulexin), a progestin (such as such as hydroxyprogesterone caproate, medroxyprogesterone/provera, megestrol acepate/megace), an adrenocorticosteroid (such as hydrocortisone, prednisone), luteinizing hormone-releasing hormone (and analogs thereof and other LHRH agonists such as buserelin and goserelin), an aromatase inhibitor (such as anastrazole/arimidex, aminoglutethimide/cytraden, exemestane) or a hormone inhibitor (such as octreotide/sandostatin).

Combined administration, as described above, may be simultaneous, separate, or sequential. For simultaneous administration the agents may be administered as one composition or as separate compositions, as appropriate.

EXEMPLIFICATION

Figure 1B:
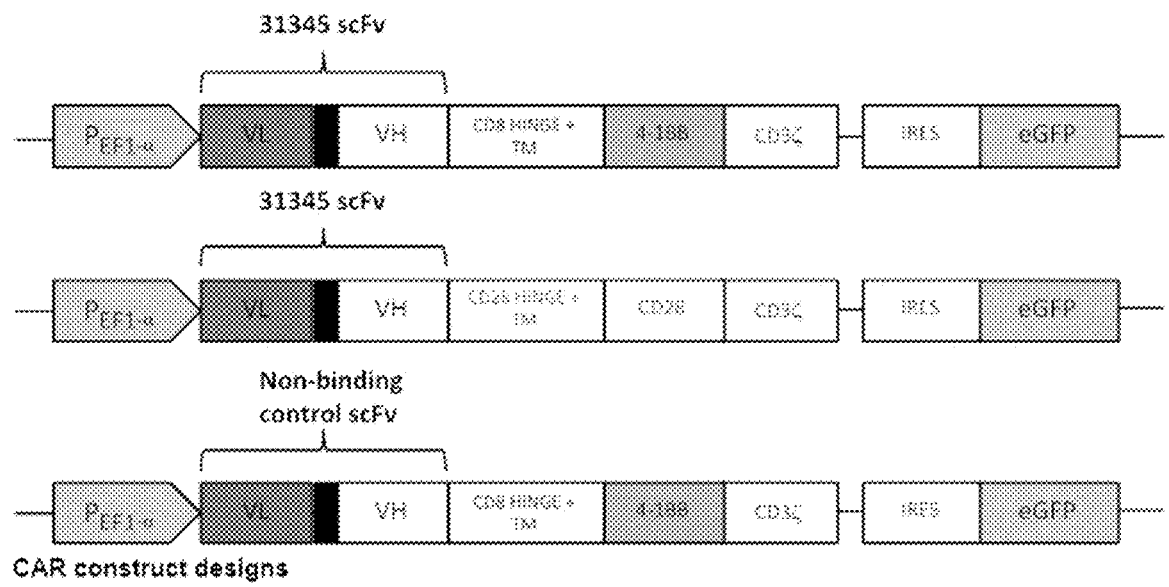

Example 1: SK-MEL-37 Tumors and Chimeric Antigen Receptors Containing an Anti-HLA-A2/MAGEA4$_{286-294}$ scFv Generation of CARS:

Chimeric antigen receptors containing either an anti-HLA-A2/MAGEA4$_{286-294}$ SCFV in the $V_L$-$V_H$ orientation plus either 1) a huCD8 hinge/transmembrane domain, a 4-1BB co-stimulatory domain, and a CD3z signaling domain (BB/z CAR), or 2) huCD28 hinge/transmembrane/costimulatory domains and a CD3z signaling domain (28/z CAR) were constructed using the $V_L$ and $V_H$ sequences of an anti-HLA-A2/MAGEA4$_{286-294}$ antibody, 31345 As a non-binding control, a BB/z CAR was designed using a different scFv plus a huCD8 hinge/transmembrane domain, a 4-1BB co-stimulatory domain, and a CD3z signaling domain. These CARs were cloned into a pLVX lentiviral vector with an EF1a promoter and IRES:eGFP sequence (for tracking CAR-transduced cells), and VSV-pseudotyped lentivirus was produced. See FIG. 1B, for construct schematics.

CD3+ T cells were isolated from human peripheral blood mononuclear cells (PBMCs) from two normal donors ('Donor 1' and 'Donor 2'), stimulated with CD3/CD28 microbeads plus 100 U/ml recombinant human IL-2, and transduced with the lentivirus at an MOI=5. The transduced cells were expanded for 19 days with CD3/CD28 microbeads plus 100 U/ml recombinant human IL-2 before being cryopreserved until use during the in vivo experiment.

Implantation and Measurement of Xenogenic Tumors

To determine the in vivo efficacy of HLA-A2/MAGEA4$_{286-294}$-targeted chimeric antigen receptor (CAR) T cells, a xenogenic tumor study was performed. On day 0, immunodeficient NOD.Cg-Prkdc$^{scid}$Il2rg$^{tm1Wjl}$/SzJ (NSG) mice were subcutaneously injected with 5×10$^6$ HLA-A2$^+$ MAGEA4$^+$ SK-MEL-37 human melanoma tumor cells. Using mass spectrometry techniques have been used to determined that SK-MEL-37 melanoma cells express approximately 1,326 cell-surface copies of the MAGEA4$_{286-294}$ peptide. On day 7 after tumors were established, the mice (n=5 per group) were intravenously injected with 4×10$^6$ T cells that express either the non-binding control BB/z CAR (Control CAR T), the anti-HLA-A2/MAGEA4$_{286-294}$ BB/z CAR, or the anti-HLA-A2/MAGEA4$_{286-294}$ 28/z CAR (as determined by the frequency of cells expressing GFP, which is a marker for those cells that have been transduced with CAR) from two different donors. Tumor growth was assessed through day 64 by measuring tumor volumes.

Calculation of Xenogenic Tumor Growth and Inhibition

In order to determine tumor volume by external caliper, the greatest longitudinal diameter (length in mm) and the greatest transverse diameter (width in mm) were determined. Tumor volumes based on caliper measurements were calculated by the formula: Volume (mm$^3$)=(length×width$^2$)/2.

Collectively, the results demonstrate that MAGEA4$_{286-294}$ 28/z CAR T cells from two donors demonstrate superior in vivo anti-tumor activity and anti-tumor kinetics compared to MAGEA4$_{286-294}$ BB/z CAR T cells.

TABLE 8

| | | | Description of CARs: |
|---|---|---|---|
| AbPID | AbPID | Specificity | Description |
| 17363 | 17363 | Non-binding control | Anti-HLA-A2/HPV16E7$_{11-19}$ scFv 17363 in VL-VH orientation with huCD8 hinge/transmembrane domain, a 4-1BB co-stimulatory domain, and a CD3z signaling domain (Control CAR) |
| 31345 | 31345 | HLA-A2/MAGEA4$_{286-294}$ | Anti-MAGEA4$_{286-294}$ scFv 31345 in VL-VH orientation with huCD8 hinge/transmembrane domain, a 4-1BB co-stimulatory domain, and a CD3z signaling domain (BB/z CAR) |
| 31345 | 31345 | HLA-A2/MAGEA4$_{286-294}$ | Anti-MAGEA4$_{286-294}$ scFv 31345 in VL-VH orientation with huCD28 hinge/transmembrane/costimulatory domains and a CD3z signaling domain (28/z CAR) |

Experimental Procedure: Results Summary and Conclusions

Figure 2A:
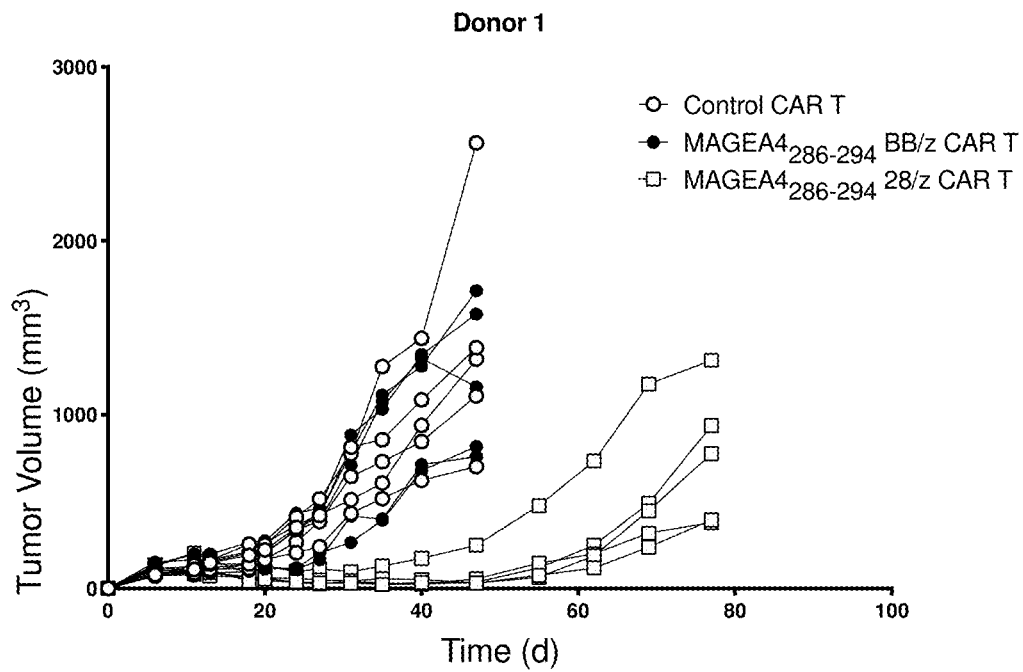
FIGS. 2A-2D show MAGEA4$_{286-294}$ 28/z CAR T cells from two donors demonstrate superior in vivo anti-tumor activity and anti-tumor kinetics compared to MAGEA4$_{286-294}$ BB/z CAR T cells in the SK-MEL-37 melanoma tumor model. NSG mice were subcutaneously implanted with HLA-A2$^+$MAGEA4$^+$ SK-MEL-37 human melanoma tumor cells. On day 7 after tumors were established, the mice (n=5 per group) were intravenously injected with 4×10$^6$ T cells that express either the non-binding control BB/z CAR (Control CAR T), the anti-HLA-A2/MAGEA4$_{286-294}$ BB/z CAR, or the anti-HLA-A2/MAGEA4$_{286-294}$ 28/z CAR from two different donors. Tumor growth was assessed by measuring tumor volumes. Data shown from Donor 1 in FIGS. 2A and 2B and Donor 2 FIGS. 2C and 2D.
Figure 2B:
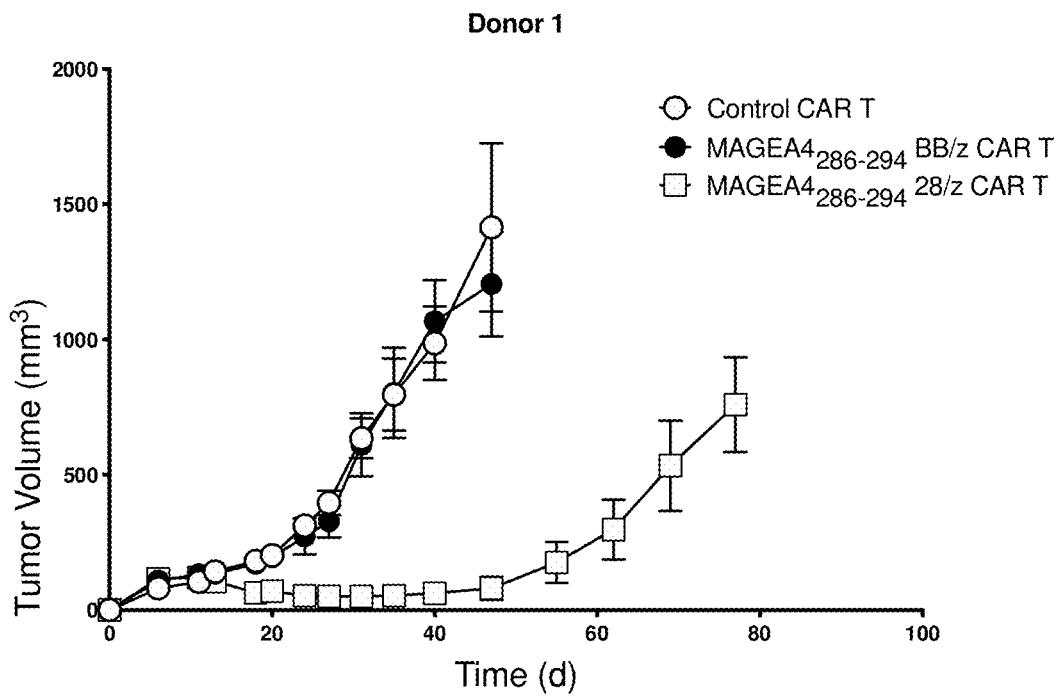

Donor 1: SK-MEL-37 tumors grew progressively in mice receiving either Control CAR T cells or MAGEA4$_{286-294}$ BB/z CAR T cells. By contrast, MAGEA4$_{286-294}$ 28/z suppressed the growth of established SK-MEL-37 tumors in vivo. Enhanced efficacy of MAGEA4$_{286-294}$ 28/z CAR vs. MAGEA4$_{286-294}$ BB/z CAR is confirmed, as tumor sizes on days 31, 35, 40, 47, 55, and 62 are statistically significant, with p<0.0001 by 2-way ANOVA test. See FIGS. 2A and 2B.

Figure 2C:
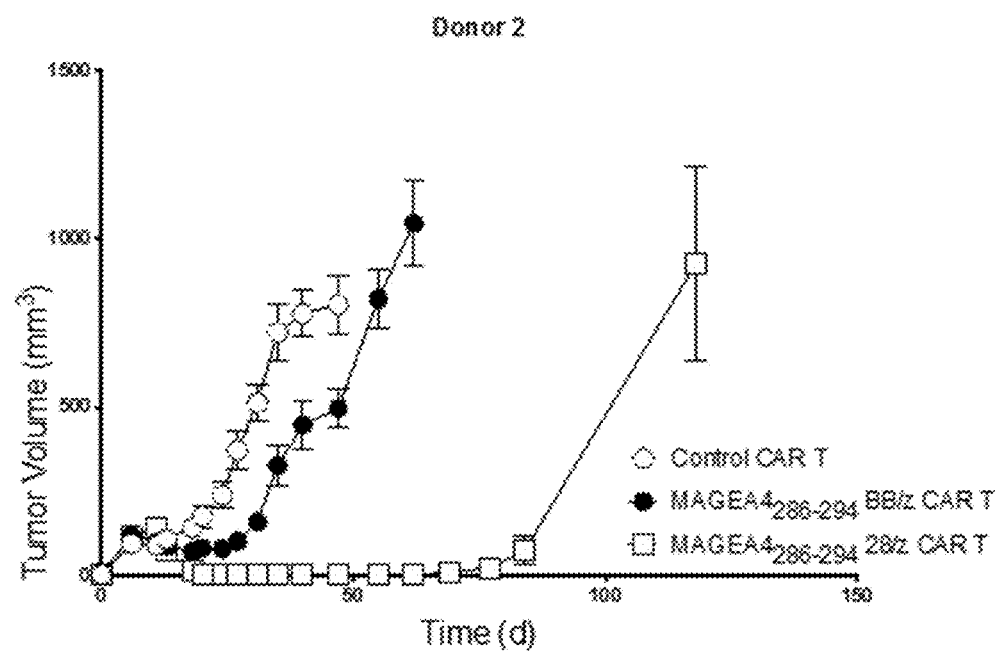
Figure 2D:
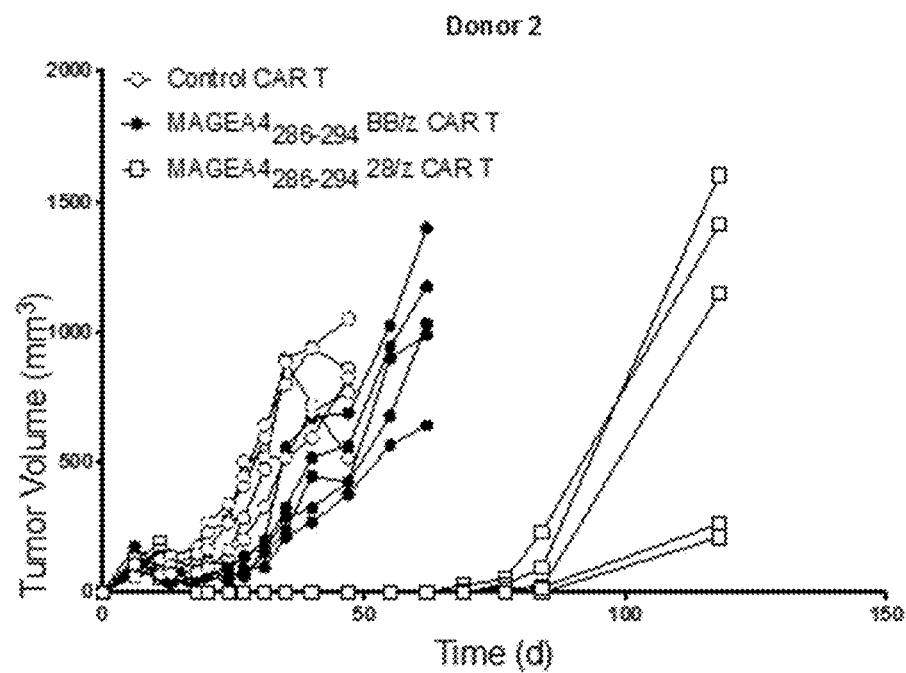
Figure 3A:
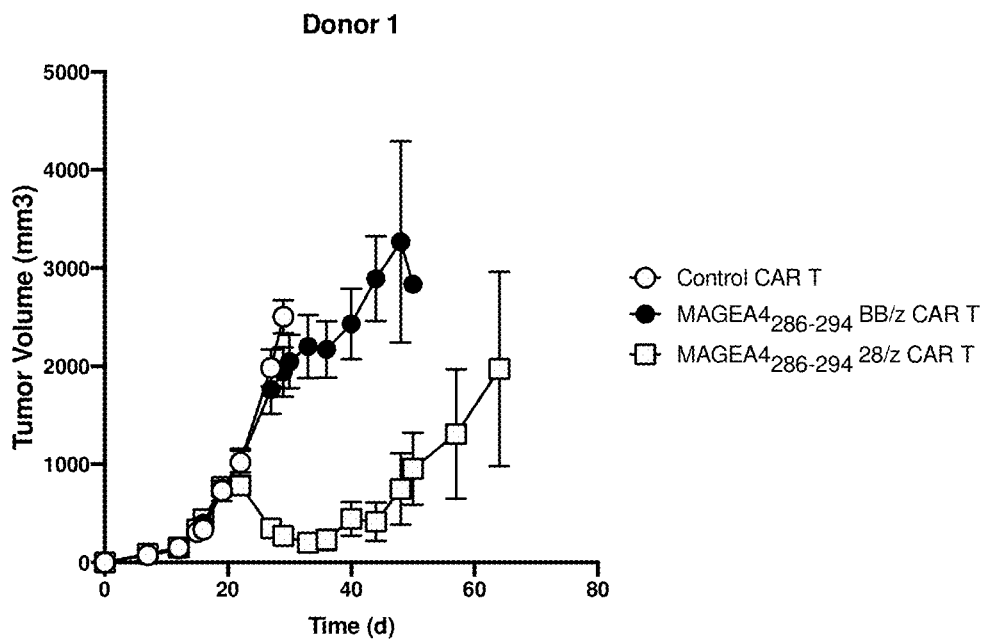
FIGS. 3A-3D show MAGEA4$_{286-294}$ 28/z CAR T cells from two donors demonstrate superior in vivo anti-tumor activity and anti-tumor kinetics compared to MAGEA4$_{286-294}$ BB/z CAR T cells in the A375 melanoma tumor model. NSG mice were subcutaneously injected with HLA-A2$^+$MAGEA4$^+$ A375 human melanoma tumor cells. On day 13 after tumors were established, the mice (n=5 per group) were intravenously injected with 4×10$^6$ T cells that express either the non-binding control BB/z CAR (Control CAR T), the anti-HLA-A2/MAGEA4$_{286-294}$ BB/z CAR, or the anti-HLA-A2/MAGEA4$_{286-294}$ 28/z CAR from two different donors. Tumor growth was assessed through day 64 by measuring tumor volumes. Data shown from Donor 1 in FIGS. 3A and 3B and Donor 2 in FIGS. 3C and 3D.
Figure 3B:
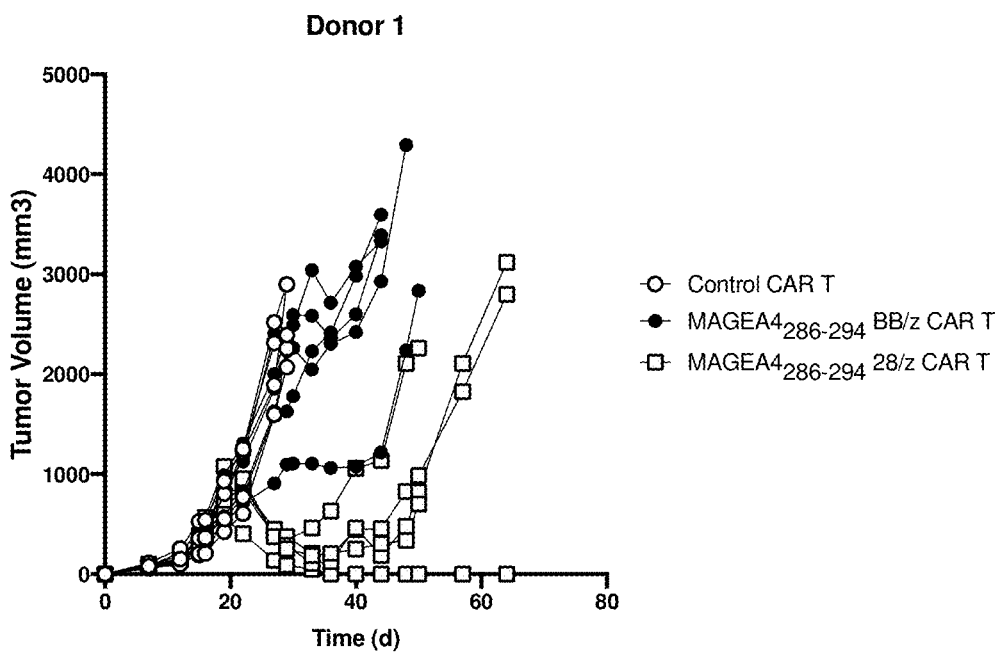
Figure 3C:
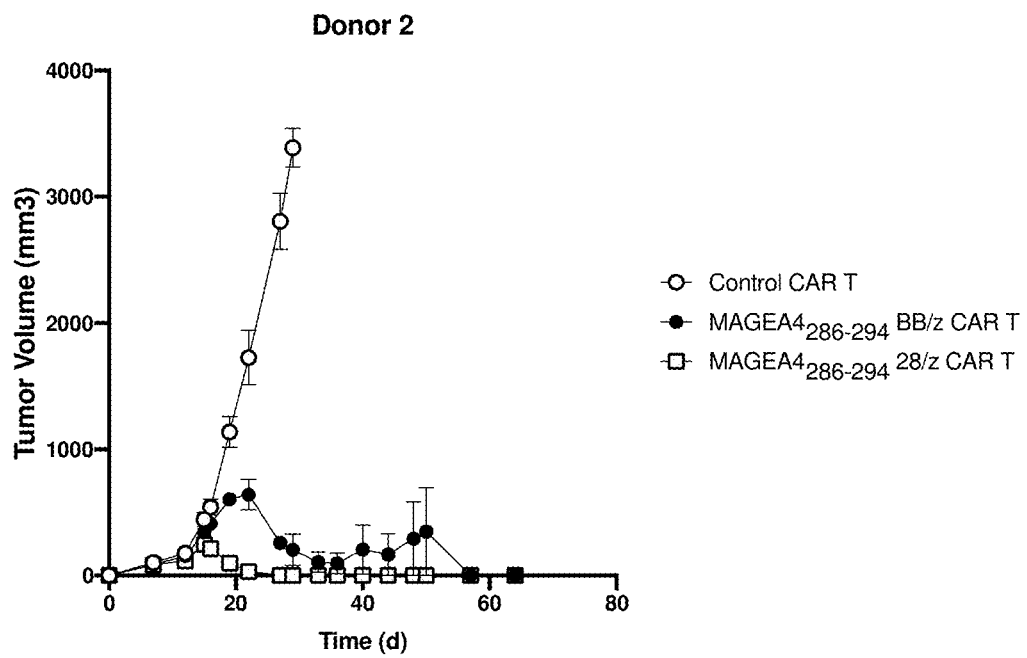
Figure 3D:
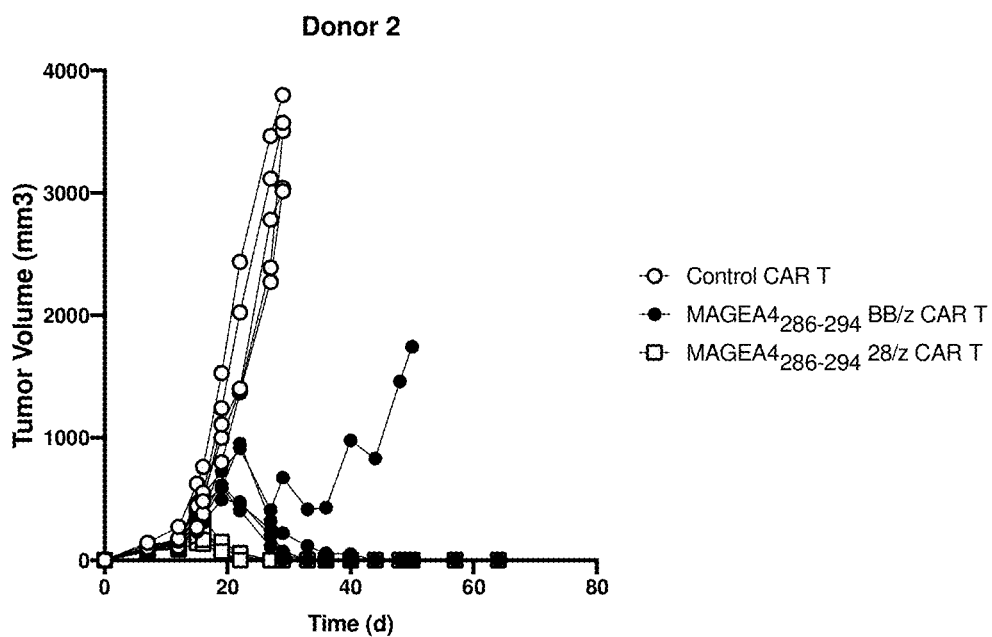

Donor 2: SK-MEL-37 tumors grew progressively in mice receiving Control CAR T cells. Treatment with MAGEA4$_{286-294}$ BB/z CAR T cells demonstrated efficacy and delayed tumor growth by approximately one week. However, MAGEA4$_{286-294}$ 28/z CAR T cells strongly suppressed SK-MEL-37 tumor growth, bringing tumors to undetectable (unpalpable) levels in 5 of 5 mice by day 20. These tumors remained undetectable through days 62-69, upon which time tumors recurred. Enhanced anti-tumor activity of MAGEA4$_{286-294}$ 28/z CAR vs. MAGEA4$_{286-294}$ BB/z CAR is confirmed, as tumor sizes on days 35 are statistically significant (p=0.0037) and tumor sizes on days 40, 47, 55, and 62 are statistically significant, with p<0.0001 by 2-way ANOVA test. See FIGS. 2C and 2D.

TABLE 9

| Data Summary: | | |
|---|---|---|
| CAR T Treatment | Average Tumor Size (mm$^3$) ± SEM on Day 6 | Number of mice still alive (of 5) on day 6 |
| Donor 1: Control CAR T | 80.6 ± 4.2 | 5 |
| Donor 1: MAGEA4$_{286-294}$ BB/z CAR T | 109.4 ± 14.6 | 5 |
| Donor 1: MAGEA4$_{286-294}$ 28/z CAR T | 115.3 ± 7.0 | 5 |
| Donor 2: Control CAR T | 92.6 ± 12.4 | 5 |
| Donor 2: MAGEA4$_{286-294}$ BB/z CAR T | 115.4 ± 16.7 | 5 |
| Donor 2: MAGEA4$_{286-294}$ 28/z CAR T | 112.8 ± 5.5 | 5 |
| CAR T Treatment | Average Tumor Size (mm$^3$) ± SEM on Day 11 | Number of mice still alive (of 5) on day 11 |
| Donor 1: Control CAR T | 104.0 ± 9.4 | 5 |
| Donor 1: MAGEA4$_{286-294}$ BB/z CAR T | 133.5 ± 21.1 | 5 |
| Donor 1: MAGEA4$_{286-294}$ 28/z CAR T | 120.8 ± 22.0 | 5 |
| Donor 2: Control CAR T | 87.7 ± 10.6 | 5 |
| Donor 2: MAGEA4$_{286-294}$ BB/z CAR T | 97.3 ± 12.9 | 5 |
| Donor 2: MAGEA4$_{286-294}$ 28/z CAR T | 136.9 ± 23.3 | 5 |
| CAR T Treatment | Average Tumor Size (mm$^3$) ± SEM on Day 13 | Number of mice still alive (of 5) on day 13 |
| Donor 1: Control CAR T | 142.2 ± 9.0 | 5 |
| Donor 1: MAGEA4$_{286-294}$ BB/z CAR T | 133.7 ± 20.1 | 5 |
| Donor 1: MAGEA4$_{286-294}$ 28/z CAR T | 106.4 ± 17.0 | 5 |
| Donor 2: Control CAR T | 106.4 ± 14.7 | 5 |
| Donor 2: MAGEA4$_{286-294}$ BB/z CAR T | 83.5 ± 16.4 | 5 |
| Donor 2: MAGEA4$_{286-294}$ 28/z CAR T | 72.7 ± 14.8 | 5 |
| CAR T Treatment | Average Tumor Size (mm$^3$) ± SEM on Day 18 | Number of mice still alive (of 5) on day 18 |
| Donor 1: Control CAR T | 181.3 ± 24.4 | 5 |
| Donor 1: MAGEA4$_{286-294}$ BB/z CAR T | 171.3 ± 29.3 | 5 |
| Donor 1: MAGEA4$_{286-294}$ 28/z CAR T | 63.7 ± 6.8 | 5 |
| Donor 2: Control CAR T | 139.8 ± 17.6 | 5 |
| Donor 2: MAGEA4$_{286-294}$ BB/z CAR T | 70.7 ± 6.6 | 5 |
| Donor 2: MAGEA4$_{286-294}$ 28/z CAR T | 14.1 ± 6.5 | 5 |
| CAR T Treatment | Average Tumor Size (mm$^3$) ± SEM on Day 20 | Number of mice still alive (of 5) on day 20 |
| Donor 1: Control CAR T | 202.7 ± 16.5 | 5 |
| Donor 1: MAGEA4$_{286-294}$ BB/z CAR T | 194.5 ± 33.0 | 5 |
| Donor 1: MAGEA4$_{286-294}$ 28/z CAR T | 70.0 ± 15.6 | 5 |
| Donor 2: Control CAR T | 174.3 ± 33.7 | 5 |
| Donor 2: MAGEA4$_{286-294}$ BB/z CAR T | 79.4 ± 11.0 | 5 |
| Donor 2: MAGEA4$_{286-294}$ 28/z CAR T | 0.0 ± 0.0 | 5 |
| CAR T Treatment | Average Tumor Size (mm$^3$) ± SEM on Day 24 | Number of mice still alive (of 5) on day 24 |
| Donor 1: Control CAR T | 312.5 ± 35.3 | 5 |
| Donor 1: MAGEA4$_{286-294}$ BB/z CAR T | 272.3 ± 66.8 | 5 |
| Donor 1: MAGEA4$_{286-294}$ 28/z CAR T | 52.9 ± 12.2 | 5 |
| Donor 2: Control CAR T | 237.3 ± 37.7 | 5 |
| Donor 2: MAGEA4$_{286-294}$ BB/z CAR T | 78.2 ± 11.2 | 5 |
| Donor 2: MAGEA4$_{286-294}$ 28/z CAR T | 0.0 ± 0.0 | 5 |
| CAR T Treatment | Average Tumor Size (mm$^3$) ± SEM on Day 27 | Number of mice still alive (of 5) on day 27 |
| Donor 1: Control CAR T | 396.5 ± 44.7 | 5 |
| Donor 1: MAGEA4$_{286-294}$ BB/z CAR T | 328.0 ± 60.3 | 5 |
| Donor 1: MAGEA4$_{286-294}$ 28/z CAR T | 49.9 ± 16.1 | 5 |
| Donor 2: Control CAR T | 371.0 ± 54.6 | 5 |
| Donor 2: MAGEA4$_{286-294}$ BB/z CAR T | 100.0 ± 15.9 | 5 |
| Donor 2: MAGEA4$_{286-294}$ 28/z CAR T | 0.0 ± 0.0 | 5 |

TABLE 9-continued

| Data Summary: | | |
|---|---|---|
| CAR T Treatment | Average Tumor Size (mm$^3$) ± SEM on Day 31 | Number of mice still alive (of 5) on day 31 |
| Donor 1: Control CAR T | 635.0 ± 73.7 | 5 |
| Donor 1: MAGEA4$_{286-294}$ BB/z CAR T | 610.4 ± 116.4 | 5 |
| Donor 1: MAGEA4$_{286-294}$ 28/z CAR T | 50.5 ± 11.8 | 5 |
| Donor 2: Control CAR T | 512.6 ± 54.2 | 5 |
| Donor 2: MAGEA4$_{286-294}$ BB/z CAR T | 158.0 ± 17.2 | 5 |
| Donor 2: MAGEA4$_{286-294}$ 28/z CAR T | 0.0 ± 0.0 | 5 |
| CAR T Treatment | Average Tumor Size (mm$^3$) ± SEM on Day 35 | Number of mice still alive (of 5) on day 35 |
| Donor 1: Control CAR T | 796.8 ± 132.7 | 5 |
| Donor 1: MAGEA4$_{286-294}$ BB/z CAR T | 803.1 ± 166.7 | 5 |
| Donor 1: MAGEA4$_{286-294}$ 28/z CAR T | 52.6 ± 19.8 | 5 |
| Donor 2: Control CAR T | 724.1 ± 85.7 | 5 |
| Donor 2: MAGEA4$_{286-294}$ BB/z CAR T | 325.4 ± 61.1 | 5 |
| Donor 2: MAGEA4$_{286-294}$ 28/z CAR T | 0.0 ± 0.0 | 5 |
| CAR T Treatment | Average Tumor Size (mm$^3$) ± SEM on Day 40 | Number of mice still alive (of 5) on day 40 |
| Donor 1: Control CAR T | 986.3 ± 136.1 | 5 |
| Donor 1: MAGEA4$_{286-294}$ BB/z CAR T | 1067.8 ± 152.5 | 5 |
| Donor 1: MAGEA4$_{286-294}$ 28/z CAR T | 62.2 ± 28.2 | 5 |
| Donor 2: Control CAR T | 778.5 ± 69.8 | 5 |
| Donor 2: MAGEA4$_{286-294}$ BB/z CAR T | 446.5 ± 71.1 | 5 |
| Donor 2: MAGEA4$_{286-294}$ 28/z CAR T | 0.0 ± 0.0 | 5 |
| CAR T Treatment | Average Tumor Size (mm$^3$) ± SEM on Day 47 | Number of mice still alive (of 5) on day 47 |
| Donor 1: Control CAR T | 1414.9 ± 311.2 | 5 |
| Donor 1: MAGEA4$_{286-294}$ BB/z CAR T | 1205.2 ± 193.7 | 5 |
| Donor 1: MAGEA4$_{286-294}$ 28/z CAR T | 80.5 ± 42.3 | 5 |
| Donor 2: Control CAR T | 804.6 ± 85.8 | 5 |
| Donor 2: MAGEA4$_{286-294}$ BB/z CAR T | 496.7 ± 57.6 | 5 |
| Donor 2: MAGEA4$_{286-294}$ 28/z CAR T | 0.0 ± 0.0 | 5 |
| CAR T Treatment | Average Tumor Size (mm$^3$) ± SEM on Day 55 | Number of mice still alive (of 5) on day 55 |
| Donor 1: Control CAR T | Animals Euthanized | 0 |
| Donor 1: MAGEA4$_{286-294}$ BB/z CAR T | Animals Euthanized | 0 |
| Donor 1: MAGEA4$_{286-294}$ 28/z CAR T | 175.9 ± 76.5 | 5 |
| Donor 2: Control CAR T | Animals Euthanized | 0 |
| Donor 2: MAGEA4$_{286-294}$ BB/z CAR T | 823.1 ± 85.8 | 5 |
| Donor 2: MAGEA4$_{286-294}$ 28/z CAR T | 0.0 ± 0.0 | 5 |
| CAR T Treatment | Average Tumor Size (mm$^3$) ± SEM on Day 62 | Number of mice still alive (of 5) on day 62 |
| Donor 1: Control CAR T | Animals Euthanized | 0 |
| Donor 1: MAGEA4$_{286-294}$ BB/z CAR T | Animals Euthanized | 0 |
| Donor 1: MAGEA4$_{286-294}$ 28/z CAR T | 298.0 ± 110.8 | 5 |
| Donor 2: Control CAR T | Animals Euthanized | 0 |
| Donor 2: MAGEA4$_{286-294}$ BB/z CAR T | 1048.0 ± 124.3 | 5 |
| Donor 2: MAGEA4$_{286-294}$ 28/z CAR T | 0.0 ± 0.0 | 5 |
| CAR T Treatment | Average Tumor Size (mm$^3$) ± SEM on Day 69 | Number of mice still alive (of 5) on day 69 |
| Donor 1: Control CAR T | Animals Euthanized | 0 |
| Donor 1: MAGEA4$_{286-294}$ BB/z CAR T | Animals Euthanized | 0 |
| Donor 1: MAGEA4$_{286-294}$ 28/z CAR T | 533.3 ± 166.8 | 5 |
| Donor 2: Control CAR T | Animals Euthanized | 0 |
| Donor 2: MAGEA4$_{286-294}$ BB/z CAR T | Animals Euthanized | 0 |
| Donor 2: MAGEA4$_{286-294}$ 28/z CAR T | 7.3 ± 5.6 | 5 |

TABLE 9-continued

Data Summary:

| CAR T Treatment | Average Tumor Size (mm³) ± SEM on Day 77 | Number of mice still alive (of 5) on day 77 |
|---|---|---|
| Donor 1: Control CAR T | Animals Euthanized | 0 |
| Donor 1: MAGEA4$_{286-294}$ BB/z CAR T | Animals Euthanized | 0 |
| Donor 1: MAGEA4$_{286-294}$ 28/z CAR T | 759.6 ± 175.7 | 5 |
| Donor 2: Control CAR T | Animals Euthanized | 0 |
| Donor 2: MAGEA4$_{286-294}$ BB/z CAR T | Animals Euthanized | 0 |
| Donor 2: MAGEA4$_{286-294}$ 28/z CAR T | 20.6 ± 10.1 | 5 |

| CAR T Treatment | Average Tumor Size (mm³) ± SEM on Day 84 | Number of mice still alive (of 5) on day 84 |
|---|---|---|
| Donor 1: Control CAR T | Animals Euthanized | 0 |
| Donor 1: MAGEA4$_{286-294}$ BB/z CAR T | Animals Euthanized | 0 |
| Donor 1: MAGEA4$_{286-294}$ 28/z CAR T | Animals Euthanized | 0 |
| Donor 2: Control CAR T | Animals Euthanized | 0 |
| Donor 2: MAGEA4$_{286-294}$ BB/z CAR T | Animals Euthanized | 0 |
| Donor 2: MAGEA4$_{286-294}$ 28/z CAR T | 73.0 ± 42.6 | 5 |

| CAR T Treatment | Average Tumor Size (mm³) ± SEM on Day 118 | Number of mice still alive (of 5) on day 118 |
|---|---|---|
| Donor 1: Control CAR T | Animals Euthanized | 0 |
| Donor 1: MAGEA4$_{286-294}$ BB/z CAR T | Animals Euthanized | 0 |
| Donor 1: MAGEA4$_{286-294}$ 28/z CAR T | Animals Euthanized | 0 |
| Donor 2: Control CAR T | Animals Euthanized | 0 |
| Donor 2: MAGEA4$_{286-294}$ BB/z CAR T | Animals Euthanized | 0 |
| Donor 2: MAGEA4$_{286-294}$ 28/z CAR T | 928.2 ± 291.1 | 5 |

Example 2: A375 Tumors and Chimeric Antigen Receptors Containing an Anti-HLA-A2/MAGEA4$_{286-294}$ scFv Constructs and CAR T Cells Chimeric antigen receptors containing either an anti-HLA-A2/MAGEA4$_{286-294}$ SCFV in the $V_L$-$V_H$ orientation plus either 1) a huCD8 hinge/transmembrane domain, a 4-1BB co-stimulatory domain, and a CD3z signaling domain (BB/z CAR), or 2) huCD28 hinge/transmembrane/costimulatory domains and a CD3z signaling domain (28/z CAR) were constructed using the $V_L$ and $V_H$ sequences of an anti-HLA-A2/MAGEA4$_{286-294}$ antibody, 31345. As a non-binding control, a BB/z CAR was designed using a scFv plus a huCD8 hinge/transmembrane domain, a 4-1BB co-stimulatory domain, and a CD3z signaling domain. These CARs were cloned into a pLVX lentiviral vector with an EF1a promoter and IRES:eGFP sequence (for tracking CAR-transduced cells), and VSV-pseudotyped lentivirus was produced. See FIG. 1B for construct schematics, and FIGS. 3A-3D for the results.

CD3+ T cells were isolated from human peripheral blood mononuclear cells (PBMCs) from two normal donors ('Donor 1' and 'Donor 2'), stimulated with CD3/CD28 microbeads plus 100 U/ml recombinant human IL-2, and transduced with the lentivirus at an MOI=5. The transduced cells were expanded for 19 days with CD3/CD28 microbeads plus 100 U/ml recombinant human IL-2 before being cryopreserved until use during the in vivo experiment.

Implantation and Measurement of Xenogenic Tumors

To determine the in vivo efficacy of HLA-A2/MAGEA4$_{286-294}$-targeted chimeric antigen receptor (CAR) T cells, a xenogenic tumor study was performed. On day 0, immunodeficient NOD.Cg-Prkdc$^{scid}$Il2rg$^{tm1Wjl}$/SzJ (NSG) mice were subcutaneously injected with 5×10⁶ HLA-A2⁺ MAGEA4⁺ A375 human melanoma tumor cells. Using mass spectrometry techniques have determined that A375 melanoma cells express approximately 424 cell-surface copies of the MAGEA4$_{286-294}$ peptide. On day 13 after tumors were established, the mice (n=5 per group) were intravenously injected with 4×10⁶ T cells that express either the non-binding control BB/z CAR (Control CAR T), the anti-HLA-A2/MAGEA4$_{286-294}$ BB/z CAR, or the anti-HLA-A2/MAGEA4$_{286-294}$ 28/z CAR (as determined by the frequency of cells expressing GFP, which is a marker for those cells that have been transduced with CAR) from two different donors. Tumor growth was assessed through day 64 by measuring tumor volumes.

Calculation of Xenogenic Tumor Growth and Inhibition

In order to determine tumor volume by external caliper, the greatest longitudinal diameter (length in mm) and the greatest transverse diameter (width in mm) were determined. Tumor volumes based on caliper measurements were calculated by the formula: Volume (mm³)=(length×width²)/2.

Results Summary and Conclusions

Donor 1: A375 tumors grew progressively in mice receiving either Control CAR T cells or MAGEA4$_{286-294}$ BB/z CAR T cells. By contrast, MAGEA4$_{286-294}$ 28/z suppressed the growth of established A375 tumors in vivo, with 1 of 5 mice tumor-free at day 64. Enhanced efficacy of MAGEA4$_{286-294}$ 28/z CAR vs. MAGEA4$_{286-294}$ BB/z CAR is confirmed, as tumor sizes on days 27, 29, 33, 36, 40 and 44 are statistically significant, with p<0.0001 by 2-way ANOVA test. See FIGS. 3A and 3B.

Donor 2: A375 tumors grew progressively in mice receiving Control CAR T cells. Treatment with both MAGEA4$_{286-294}$ BB/z and MAGEA4$_{286-294}$ 28/z CAR T cells suppressed A375 tumor growth, but with different kinetics. MAGEA4$_{286-294}$ 28/z CAR T cells acted with faster kinetics, eradicating tumors in 5 of 5 mice by day 27. MAGEA4$_{286-294}$ BB/z CAR T cells worked with slower kinetics, eradicating tumors in 4 of 5 mice by day 44. Enhanced kinetics of anti-tumor activity of MAGEA4$_{286-294}$ 28/z CAR vs. MAGEA4$_{286-294}$ BB/z CAR is confirmed, as tumor sizes on days 19 and 22 are statistically significant, with p=0.0071 and p=0.0008, respectively, by 2-way ANOVA test. See FIGS. 3C and 3D.

TABLE 10

Summary of Data

| CAR T Treatment | Average Tumor Size (mm³) ± SEM on Day 7 | Number of mice still alive (of 5) on day 7 |
| --- | --- | --- |
| Donor 1: Control CAR T | 76.5 ± 9.6 | 5 |
| Donor 1: MAGEA4$_{286-294}$ BB/z CAR T | 73.8 ± 4.0 | 5 |
| Donor 1: MAGEA4$_{286-294}$ 28/z CAR T | 89.9 ± 4.4 | 5 |
| Donor 2: Control CAR T | 102.8 ± .6 | 5 |
| Donor 2: MAGEA4$_{286-294}$ BB/z CAR T | 87.1 ± 9.7 | 5 |
| Donor 2: MAGEA4$_{286-294}$ 28/z CAR T | 83.7 ± 4.0 | 5 |
| CAR T Treatment | Average Tumor Size (mm³) ± SEM on Day 12 | Number of mice still alive (of 5) on day 12 |
| Donor 1: Control CAR T | 152.1 ± 27.7 | 5 |
| Donor 1: MAGEA4$_{286-294}$ BB/z CAR T | 131.2 ± 22.1 | 5 |
| Donor 1: MAGEA4$_{286-294}$ 28/z CAR T | 153.0 ± 7.0 | 5 |
| Donor 2: Control CAR T | 177.1 ± 26.4 | 5 |
| Donor 2: MAGEA4$_{286-294}$ BB/z CAR T | 154.9 ± 7.3 | 5 |
| Donor 2: MAGEA4$_{286-294}$ 28/z CAR T | 117.2 ± 9.3 | 5 |
| CAR T Treatment | Average Tumor Size (mm³) ± SEM on Day 15 | Number of mice still alive (of 5) on day 15 |
| Donor 1: Control CAR T | 311.7 ± 61.7 | 5 |
| Donor 1: MAGEA4$_{286-294}$ BB/z CAR T | 308.8 ± 33.2 | 5 |
| Donor 1: MAGEA4$_{286-294}$ 28/z CAR T | 337.9 ± 16.5 | 5 |
| Donor 2: Control CAR T | 443.5 ± 56.9 | 5 |
| Donor 2: MAGEA4$_{286-294}$ BB/z CAR T | 343.2 ± 41.2 | 5 |
| Donor 2: MAGEA4$_{286-294}$ 28/z CAR T | 247.2 ± 42.3 | 5 |
| CAR T Treatment | Average Tumor Size (mm³) ± SEM on Day 16 | Number of mice still alive (of 5) on day 16 |
| Donor 1: Control CAR T | 336.2 ± 60.9 | 5 |
| Donor 1: MAGEA4$_{286-294}$ BB/z CAR T | 402.6 ± 35.7 | 5 |
| Donor 1: MAGEA4$_{286-294}$ 28/z CAR T | 440.6 ± 36.4 | 5 |
| Donor 2: Control CAR T | 541.7 ± 62.6 | 5 |
| Donor 2: MAGEA4$_{286-294}$ BB/z CAR T | 409.9 ± 40.7 | 5 |
| Donor 2: MAGEA4$_{286-294}$ 28/z CAR T | 212.8 ± 33.8 | 5 |
| CAR T Treatment | Average Tumor Size (mm³) ± SEM on Day 19 | Number of mice still alive (of 5) on day 19 |
| Donor 1: Control CAR T | 731.6 ± 103.9 | 5 |
| Donor 1: MAGEA4$_{286-294}$ BB/z CAR T | 755.6 ± 92.2 | 5 |
| Donor 1: MAGEA4$_{286-294}$ 28/z CAR T | 769.7 ± 86.6 | 5 |
| Donor 2: Control CAR T | 1136.3 ± 122.1 | 5 |
| Donor 2: MAGEA4$_{286-294}$ BB/z CAR T | 603.9 ± 36.8 | 5 |
| Donor 2: MAGEA4$_{286-294}$ 28/z CAR T | 98.4 ± 15.6 | 5 |
| CAR T Treatment | Average Tumor Size (mm³) ± SEM on Day 22 | Number of mice still alive (of 5) on day 22 |
| Donor 1: Control CAR T | 1021.3 ± 138.5 | 5 |
| Donor 1: MAGEA4$_{286-294}$ BB/z CAR T | 1027.8 ± 111.5 | 5 |
| Donor 1: MAGEA4$_{286-294}$ 28/z CAR T | 785.7 ± 97.4 | 5 |
| Donor 2: Control CAR T | 1725.9 ± 216.2 | 5 |
| Donor 2: MAGEA4$_{286-294}$ BB/z CAR T | 641.5 ± 119.9 | 5 |
| Donor 2: MAGEA4$_{286-294}$ 28/z CAR T | 30.2 ± 13.0 | 5 |

TABLE 10-continued

Summary of Data

| CAR T Treatment | Average Tumor Size (mm$^3$) ± SEM on Day 27 | Number of mice still alive (of 5) on day 27 |
|---|---|---|
| Donor 1: Control CAR T | 1983.6 ± 187.3 | 5 |
| Donor 1: MAGEA4$_{286-294}$ BB/z CAR T | 1759.7 ± 247.6 | 5 |
| Donor 1: MAGEA4$_{286-294}$ 28/z CAR T | 347.9 ± 54.2 | 5 |
| Donor 2: Control CAR T | 2806.0 ± 222.7 | 5 |
| Donor 2: MAGEA4$_{286-294}$ BB/z CAR T | 258.2 ± 50.5 | 5 |
| Donor 2: MAGEA4$_{286-294}$ 28/z CAR T | 0.0 ± 0.0 | 5 |

| CAR T Treatment | Average Tumor Size (mm$^3$) ± SEM on Day 29 | Number of mice still alive (of 5) on day 29 |
|---|---|---|
| Donor 1: Control CAR T | 2503.7 ± 169.4 | 5 |
| Donor 1: MAGEA4$_{286-294}$ BB/z CAR T | 1941.9 ± 252.1 | 5 |
| Donor 1: MAGEA4$_{286-294}$ 28/z CAR T | 270.3 ± 49.9 | 5 |
| Donor 2: Control CAR T | 3387.0 ± 154.8 | 5 |
| Donor 2: MAGEA4$_{286-294}$ BB/z CAR T | 203.6 ± 123.4 | 5 |
| Donor 2: MAGEA4$_{286-294}$ 28/z CAR T | 0.0 ± 0.0 | 5 |

| CAR T Treatment | Average Tumor Size (mm$^3$) ± SEM on Day 33 | Number of mice still alive (of 5) on day 33 |
|---|---|---|
| Donor 1: Control CAR T | Animals Euthanized | 0 |
| Donor 1: MAGEA4$_{286-294}$ BB/z CAR T | 2201.9 ± 321.9 | 5 |
| Donor 1: MAGEA4$_{286-294}$ 28/z CAR T | 202.7 ± 70.7 | 5 |
| Donor 2: Control CAR T | Animals Euthanized | 0 |
| Donor 2: MAGEA4$_{286-294}$ BB/z CAR T | 106.2 ± 80.5 | 5 |
| Donor 2: MAGEA4$_{286-294}$ 28/z CAR T | 0.0 ± 0.0 | 5 |

| CAR T Treatment | Average Tumor Size (mm$^3$) ± SEM on Day 40 | Number of mice still alive (of 5) on day 36 |
|---|---|---|
| Donor 1: Control CAR T | Animals Euthanized | 0 |
| Donor 1: MAGEA4$_{286-294}$ BB/z CAR T | 2171.2 ± 286.1 | 5 |
| Donor 1: MAGEA4$_{286-294}$ 28/z CAR T | 230.9 ± 106.4 | 5 |
| Donor 2: Control CAR T | Animals Euthanized | 0 |
| Donor 2: MAGEA4$_{286-294}$ BB/z CAR T | 97.1 ± 83.8 | 5 |
| Donor 2: MAGEA4$_{286-294}$ 28/z CAR T | 0.0 ± 0.0 | 5 |

| CAR T Treatment | Average Tumor Size (mm$^3$) ± SEM on Day 40 | Number of mice still alive (of 5) on day 40 |
|---|---|---|
| Donor 1: Control CAR T | Animals Euthanized | 0 |
| Donor 1: MAGEA4$_{286-294}$ BB/z CAR T | 2431.9 ± 359.6 | |
| Donor 1: MAGEA4$_{286-294}$ 28/z CAR T | 443.9 ± 175.3 | |
| Donor 2: Control CAR T | Animals Euthanized | 0 |
| Donor 2: MAGEA4$_{286-294}$ BB/z CAR T | 205.7 ± 193.7 | |
| Donor 2: MAGEA4$_{286-294}$ 28/z CAR T | 0.0 ± 0.0 | 5 |

| CAR T Treatment | Average Tumor Size (mm$^3$) ± SEM on Day 44 | Number of mice still alive (of 5) on day 44 |
|---|---|---|
| Donor 1: Control CAR T | Animals Euthanized | 0 |
| Donor 1: MAGEA4$_{286-294}$ BB/z CAR T | 2892.7 ± 432.7 | 5 |
| Donor 1: MAGEA4$_{286-294}$ 28/z CAR T | 416.7 ± 195.0 | 5 |
| Donor 2: Control CAR T | Animals Euthanized | 0 |
| Donor 2: MAGEA4$_{286-294}$ BB/z CAR T | 166.0 ± 166.0 | 5 |
| Donor 2: MAGEA4$_{286-294}$ 28/z CAR T | 0.0 ± 0.0 | 5 |

| CAR T Treatment | Average Tumor Size (mm$^3$) ± SEM on Day 48 | Number of mice still alive (of 5) on day 48 |
|---|---|---|
| Donor 1: Control CAR T | Animals Euthanized | 0 |
| Donor 1: MAGEA4$_{286-294}$ BB/z CAR T | 3266.4 ± 1026.4 | 2 |
| Donor 1: MAGEA4$_{286-294}$ 28/z CAR T | 749.7 ± 364.4 | 5 |
| Donor 2: Control CAR T | Animals Euthanized | 0 |
| Donor 2: MAGEA4$_{286-294}$ BB/z CAR T | 292.0 ± 292.0 | 5 |
| Donor 2: MAGEA4$_{286-294}$ 28/z CAR T | 0.0 ± 0.0 | 5 |

TABLE 10-continued

Summary of Data

| CAR T Treatment | Average Tumor Size (mm³) ± SEM on Day 50 | Number of mice still alive (of 5) on day 50 |
| --- | --- | --- |
| Donor 1: Control CAR T | Animals Euthanized | 0 |
| Donor 1: MAGEA4$_{286-294}$ BB/z CAR T | 2835.7 ± 0.0 | 1 |
| Donor 1: MAGEA4$_{286-294}$ 28/z CAR T | 955.8 ± 367.2 | 5 |
| Donor 2: Control CAR T | Animals Euthanized | 0 |
| Donor 2: MAGEA4$_{286-294}$ BB/z CAR T | 349.0 ± 349.0 | 5 |
| Donor 2: MAGEA4$_{286-294}$ 28/z CAR T | 0.0 ± 0.0 | 5 |

| CAR T Treatment | Average Tumor Size (mm³) ± SEM on Day 57 | Number of mice still alive (of 5) on day 57 |
| --- | --- | --- |
| Donor 1: Control CAR T | Animals Euthanized | 0 |
| Donor 1: MAGEA4$_{286-294}$ BB/z CAR T | Animals Euthanized | 0 |
| Donor 1: MAGEA4$_{286-294}$ 28/z CAR T | 1311.0 ± 660.5 | 3 |
| Donor 2: Control CAR T | Animals Euthanized | 0 |
| Donor 2: MAGEA4$_{286-294}$ BB/z CAR T | 0.0 ± 0.0 | 4 |
| Donor 2: MAGEA4$_{286-294}$ 28/z CAR T | 0.0 ± 0.0 | 5 |

| CAR T Treatment | Average Tumor Size (mm³) ± SEM on Day 64 | Number of mice still alive (of 5) on day 64 |
| --- | --- | --- |
| Donor 1: Control CAR T | Animals Euthanized | 0 |
| Donor 1: MAGEA4$_{286-294}$ BB/z CAR T | Animals Euthanized | 0 |
| Donor 1: MAGEA4$_{286-294}$ 28/z CAR T | 1973.0 ± 990.8 | 3 |
| Donor 2: Control CAR T | Animals Euthanized | 0 |
| Donor 2: MAGEA4$_{286-294}$ BB/z CAR T | 0.0 ± 0.0 | 4 |
| Donor 2: MAGEA4$_{286-294}$ 28/z CAR T | 0.0 ± 0.0 | 5 |

Collectively, the results in Examples 1 and 2 demonstrate that MAGEA4$_{286-294}$ 28/z CAR T cells from two donors demonstrate superior in vivo anti-tumor activity and anti-tumor kinetics compared to MAGEA4$_{286-294}$ BB/z CAR T cells. (FIGS. 2A-2D, and FIGS. 3A-3D).

Figure 4A:
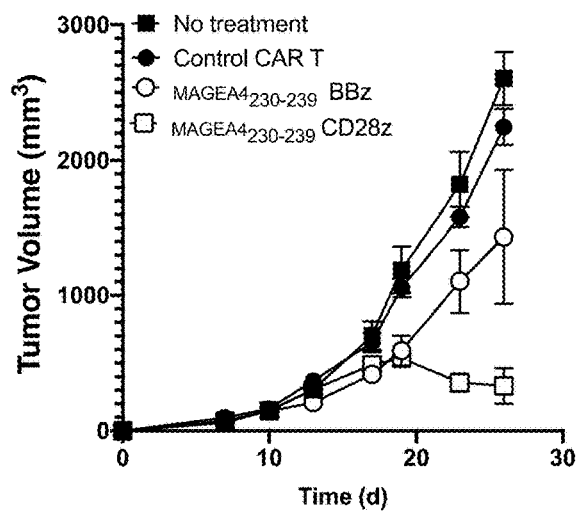
FIGS. 4A-4D show exemplary CAR constructs used in Example 3 and that MAGEA4$_{230-239}$ 28/z CAR T cells demonstrate superior in vivo anti-tumor activity and anti-tumor kinetics compared to MAGEA4$_{230-239}$ BB/z CAR T cells in the A375 melanoma tumor model.
Figure 4B:
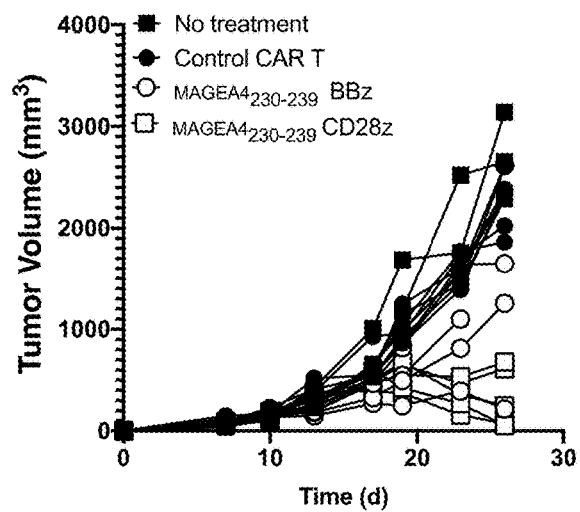
Figure 4C:
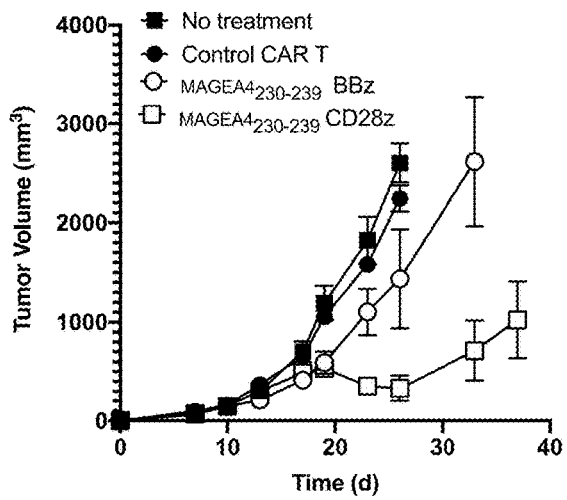
Figure 4D:
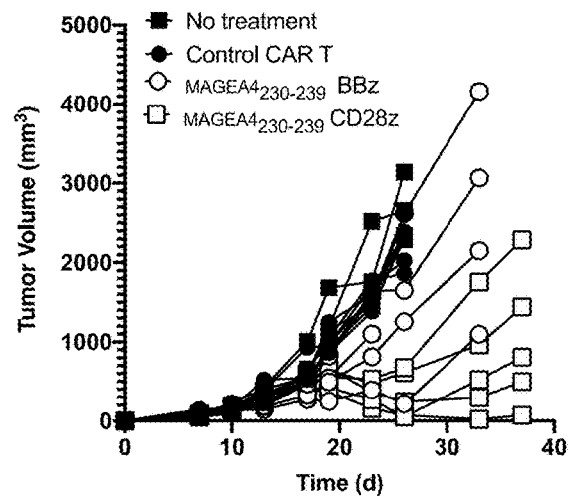
Figure 4E:
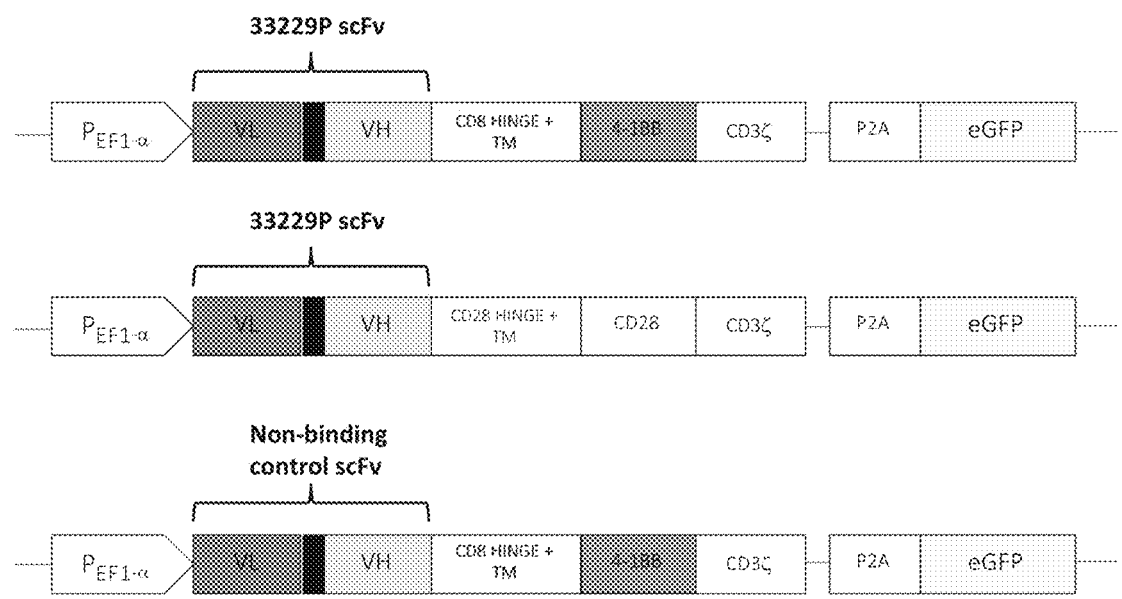
FIG. 4E shows chimeric antigen receptors containing an anti-HLA-A2/MAGEA4$_{230-239}$ 33229P scFv plus either (top) a huCD8 hinge/transmembrane domain, a 4-1BB co-stimulatory domain, and a CD3z signaling domain (BB/z CAR), or (middle) huCD28 hinge/transmembrane/costimulatory domains and a CD3z signaling domain (28/z CAR). (Bottom) An irrelevant scFv plus a huCD8 hinge/transmembrane domain, a 4-1BB co-stimulatory domain and a CD3z signaling domain served as a control CAR.

Example 3: Chimeric Antigen Receptors Containing an Anti-HLA-A2/MAGEA4$_{230-239}$ scFv Chimeric antigen receptors containing either an anti-HLA-A2/MAGEA4$_{230-239}$ SCFV in the $V_L$-$V_H$ orientation plus either 1) a huCD8 hinge/transmembrane domain, a 4-1BB co-stimulatory domain, and a CD3z signaling domain (BB/z CAR), or 2) huCD28 hinge/transmembrane/costimulatory domains and a CD3z signaling domain (28/z CAR) were constructed using the $V_L$ and $V_H$ sequences of an anti-HLA-A2/MAGEA4$_{230-239}$ antibody, 33229P. As a non-binding control, a 28/z CAR was designed using an irrelevant scFv plus a huCD28 hinge/transmembrane/costimulatory domains and a CD3z signaling domain. These CARs were cloned into a pLVX lentiviral vector with an EF1a promoter and P2A:eGFP sequence (for tracking CAR-transduced cells), and VSV-pseudotyped lentivirus was produced. See FIG. 4E for constructs and FIGS. 4A-4D for results.

TABLE 11

CAR scFv IDs:

| AbPID | AbPID | Specificity | Description |
| --- | --- | --- | --- |
| 17363 | 17363N | Non-binding control | Anti-HLA-A2/HPV16E7$_{11-19}$ scFv 17363N in VL-VH orientation with huCD28 hinge/transmembrane/costimulatory domains and a CD3z signaling domain (Control CAR) |
| 33229P | 33229P | HLA-A2/MAGEA4$_{230-239}$ | anti-HLA-A2/MAGEA4$_{230-239}$ scFv 33229P in VL-VH orientation with huCD8 hinge/transmembrane domain, a 4-1BB co-stimulatory domain, and a CD3z signaling domain (MAGEA4$_{230-239}$ BB/z CAR) |
| 33229P | 33229P | HLA-A2/MAGEA4$_{230-239}$ | anti-HLA-A2/MAGEA4$_{230-239}$ scFv 33229P in VL-VH orientation with huCD28 hinge/transmembrane/costimulatory domains and a CD3z signaling domain (MAGEA4$_{230-239}$ 28/z CAR) |

TABLE 12

Lentivirus prep IDs:

| Lentivirus Prep # | AbPID | Description |
|---|---|---|
| VVT-Lentivirus-500-001 | 17363N | Anti-HLA-A2/HPV16E7$_{11-19}$ scFv 17363N in VL-VH orientation with huCD28 hinge/transmembrane/co stimulatory domains and a CD3z signaling domain (Control CAR) |
| VVT-Lentivirus-595-001 | 33229P | anti-HLA-A2/MAGEA4$_{230-239}$ scFv 33229P in VL-VH orientation with huCD8 hinge/transmembrane domain, a 4-1BB co-stimulatory domain, and a CD3z signaling domain (MAGEA4$_{230-239}$ BB/z CAR) |
| VVT-Lentivirus-596-001 | 33229P | anti-HLA-A2/MAGEA4$_{230-239}$ scFv 33229P in VL-VH orientation with huCD28 hinge/transmembrane/co stimulatory domains and a CD3z signaling domain (MAGEA4$_{230-239}$ 28/z CAR) |

Experimental Procedure

Generation of CAR Constructs and CAR T Cells

Chimeric antigen receptors containing either an anti-HLA-A2/MAGEA4$_{230-239}$ SCFV in the $V_L$-$V_H$ orientation plus either 1) a huCD8 hinge/transmembrane domain, a 4-1BB co-stimulatory domain, and a CD3z signaling domain (BB/z CAR), or 2) huCD28 hinge/transmembrane/costimulatory domains and a CD3z signaling domain (28/z CAR) were constructed using the $V_L$ and $V_H$ sequences of an anti-HLA-A2/MAGEA4$_{230-239}$ antibody, 33229P. As a non-binding control, a 28/z CAR was designed using an irrelevant scFv plus a huCD28 hinge/transmembrane/costimulatory domains and a CD3z signaling domain. These CARs were cloned into a pLVX lentiviral vector with an EF1a promoter and P2A:eGFP sequence (for tracking CAR-transduced cells), and VSV-pseudotyped lentivirus was produced.

CD3+ T cells were isolated from human peripheral blood mononuclear cells (PBMCs) from a normal donor, stimulated with CD3/CD28 microbeads plus 100 U/ml recombinant human IL-2, and transduced with the lentivirus at an MOI=5. The transduced cells were expanded for approximately 14 days with CD3/CD28 microbeads plus 100 U/ml recombinant human IL-2 before being cryopreserved until use during the in vivo experiment.

Implantation and Measurement of Xenogenic Tumors

To determine the in vivo efficacy of anti-HLA-A2/MAGEA4$_{230-239}$-targeted chimeric antigen receptor (CAR) T cells, a xenogenic tumor study was performed. On day 0, immunodeficient NOD.Cg-Prkdc$^{scid}$Il2rg$^{tm1Wjl}$/SzJ (NSG) mice were subcutaneously injected with 5×10$^6$ HLA-A2$^+$ MAGEA4$^+$ A375 human melanoma tumor cells. Using mass spectrometry techniques it was determined that A375 melanoma cells express approximately 553 cell-surface copies of the HLA-A2/MAGEA4$_{230-239}$ peptide. On day 13 after tumors were established, the mice (n=4 or 5 per group) were intravenously injected with 4×10$^6$ T cells that express either the non-binding control BB/z CAR (Control CAR T), the anti-HLA-A2/MAGEA4$_{230-239}$ BB/z CAR, or the anti-HLA-A2/MAGEA4$_{230-239}$ 28/z CAR (as determined by the frequency of cells expressing either GFP, which is a marker for those cells that have been transduced with CAR). Tumor growth was assessed through day 28 by measuring tumor volumes.

Calculation of Xenogenic Tumor Growth and Inhibition

In order to determine tumor volume by external caliper, the greatest longitudinal diameter (length in mm) and the greatest transverse diameter (width in mm) were determined. Tumor volumes based on caliper measurements were calculated by the formula: Volume (mm$^3$)=(length×width$^2$)/2.

Results Summary and Conclusions

A375 tumors grew progressively in untreated mice and mice receiving Control CAR T cells. Mice receiving anti-HLA-A2/MAGEA4$_{230-239}$ BB/z CAR T cells demonstrated some tumor control, with reduced tumor growth compared to Control CAR T-treated mice on days 19 (p<0.02), 23 (p<0.02), and 26 (p<0.0001) (statistics analyzed by 2-way ANOVA). Anti-HLA-A2/MAGEA4$_{230-239}$ 28/z CAR T treatment also led to suppression of established A375 tumor growth on days 19 (p=0.007), 23 (p<0.0001), and 26 (p<0.0001) (statistics analyzed by 2-way ANOVA). Enhanced efficacy of anti-anti-HLA-A2/MAGEA4$_{230-239}$ 28/z CAR vs. anti-HLA-A2/MAGEA4$_{230-239}$ BB/z CAR is confirmed, as tumor sizes on days 23 (p<0.0001) and 26 (p<0.0001) are statistically significant by 2-way ANOVA. See FIGS. 4A-4D.

Collectively, the results demonstrate that anti-HLA-A2/MAGEA4$_{230-239}$ 28/z CAR T cells demonstrate superior in vivo anti-tumor activity and anti-tumor kinetics compared to anti-HLA-A2/MAGEA4$_{230-239}$ BB/z CAR T cells.

TABLE 13

Data Summary

| CAR T Treatment | Average Tumor Size (mm$^3$) on Day 7 | Tumor size standard error of the mean (SEM) | Number of mice still alive (of 5) on day 7 |
|---|---|---|---|
| Untreated | 59.7 | 9.7 | 4 |
| Control CAR T | 98.1 | 16.2 | 5 |
| MAGEA4$_{230-239}$ BB/z CAR T | 72.8 | 3.9 | 5 |
| MAGEA4$_{230-239}$ 28/z CAR T | 72.3 | 5.9 | 5 |

| CAR T Treatment | Average Tumor Size (mm$^3$) on Day 10 | Tumor size standard error of the mean (SEM) | Number of mice still alive (of 5) on day 10 |
|---|---|---|---|
| Untreated | 154.0 | 16.1 | 4 |
| Control CAR T | 163.0 | 21.6 | 5 |
| MAGEA4$_{230-239}$ BB/z CAR T | 146.1 | 4.9 | 5 |
| MAGEA4$_{230-239}$ 28/z CAR T | 148.9 | 14.1 | 5 |

| CAR T Treatment | Average Tumor Size (mm$^3$) on Day 13 | Tumor size standard error of the mean (SEM) | Number of mice still alive (of 5) on day 13 |
|---|---|---|---|
| Untreated | 302.9 | 47.2 | 4 |
| Control CAR T | 369.4 | 47.3 | 5 |
| MAGEA4$_{230-239}$ BB/z CAR T | 209.9 | 30.3 | 5 |
| MAGEA4$_{230-239}$ 28/z CAR T | 304.4 | 25.7 | 5 |

TABLE 13-continued

Data Summary

| CAR T Treatment | Average Tumor Size (mm³) on Day 17 | Tumor size standard error of the mean (SEM) | Number of mice still alive (of 5) on day 17 |
|---|---|---|---|
| Untreated | 702.5 | 105.7 | 4 |
| Control CAR T | 652.7 | 71.3 | 5 |
| MAGEA4$_{230-239}$ BB/z CAR T | 416.1 | 51.4 | 5 |
| MAGEA4$_{230-239}$ 28/z CAR T | 487.1 | 32.0 | 5 |

| CAR T Treatment | Average Tumor Size (mm³) on Day 19 | Tumor size standard error of the mean (SEM) | Number of mice still alive (of 5) on day 19 |
|---|---|---|---|
| Untreated | 1191.9 | 174.2 | 4 |
| Control CAR T | 1055.6 | 68.2 | 5 |
| MAGEA4$_{230-239}$ BB/z CAR T | 590.9 | 111.2 | 5 |
| MAGEA4$_{230-239}$ 28/z CAR T | 535.4 | 60.6 | 5 |

| CAR T Treatment | Average Tumor Size (mm³) on Day 23 | Tumor size standard error of the mean (SEM) | Number of mice still alive (of 5) on day 23 |
|---|---|---|---|
| Untreated | 1823.6 | 240.4 | 4 |
| Control CAR T | 1583.3 | 74.6 | 5 |
| MAGEA4$_{230-239}$ BB/z CAR T | 1103.7 | 234.8 | 5 |
| MAGEA4$_{230-239}$ 28/z CAR T | 356.2 | 67.3 | 5 |

| CAR T Treatment | Average Tumor Size (mm³) on Day 26 | Tumor size standard error of the mean (SEM) | Number of mice still alive (of 5) on day 26 |
|---|---|---|---|
| Untreated | 2605.5 | 196.9 | 4 |
| Control CAR T | 2246.8 | 132.9 | 5 |
| MAGEA4$_{230-239}$ BB/z CAR T | 1435.5 | 498.0 | 4 |
| MAGEA4$_{230-239}$ 28/z CAR T | 332.1 | 132.4 | 5 |

| CAR T Treatment | Average Tumor Size (mm³) on Day 33 | Tumor size standard error of the mean (SEM) | Number of mice still alive (of 5) on day 33 |
|---|---|---|---|
| Untreated | Euthanized | Euthanized | 0 |
| Control CAR T | Euthanized | Euthanized | 0 |
| MAGEA4$_{230-239}$ BB/z CAR T | 2618.3 | 652.4 | 4 |
| MAGEA4$_{230-239}$ 28/z CAR T | 712.1 | 302.9 | 5 |

| CAR T Treatment | Average Tumor Size (mm³) on Day 37 | Tumor size standard error of the mean (SEM) | Number of mice still alive (of 5) on day 37 |
|---|---|---|---|
| Untreated | Euthanized | Euthanized | 0 |
| Control CAR T | Euthanized | Euthanized | 0 |
| MAGEA4$_{230-239}$ BB/z CAR T | Euthanized | Euthanized | 0 |
| MAGEA4$_{230-239}$ 28/z CAR T | 1021.8 | 387.1 | 5 |

Figure 5A:
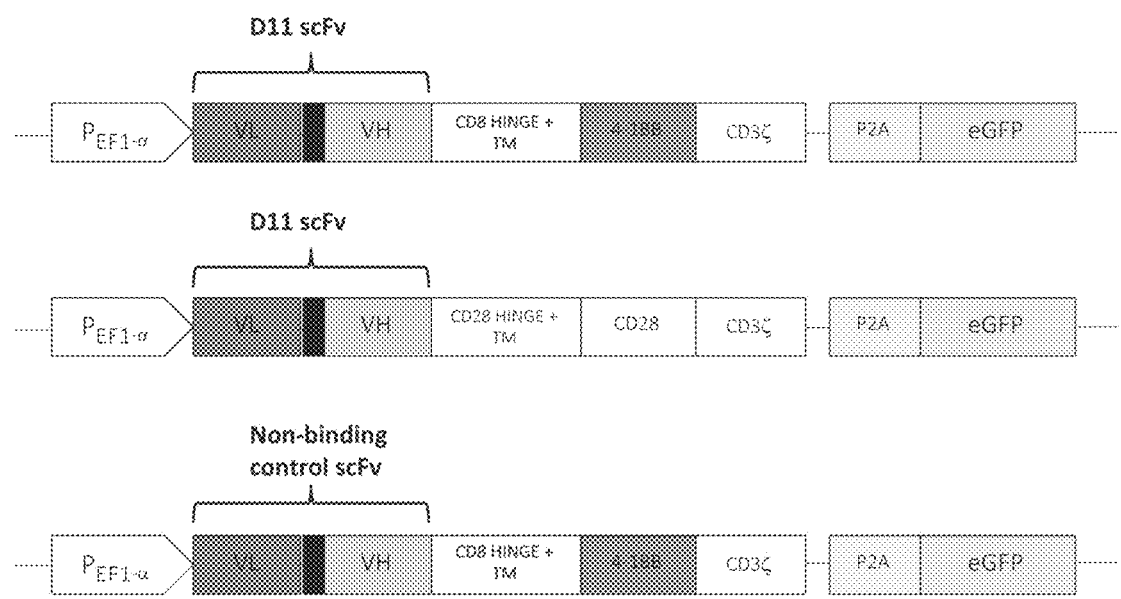
Figure 5B:
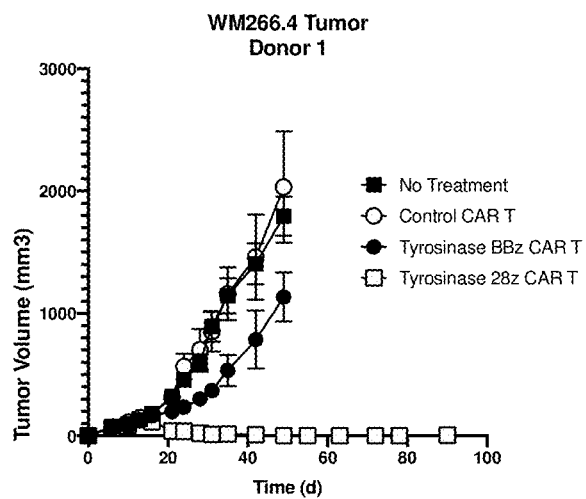
Figure 5C:
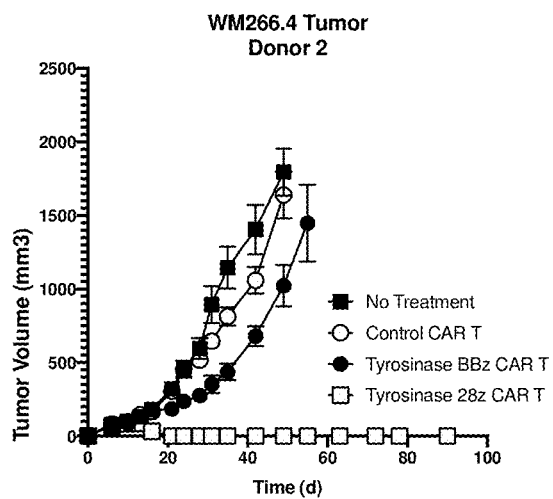
Figure 5D:
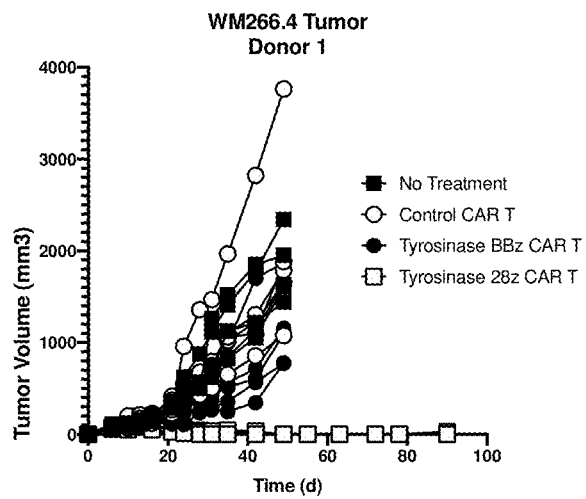
Figure 5E:
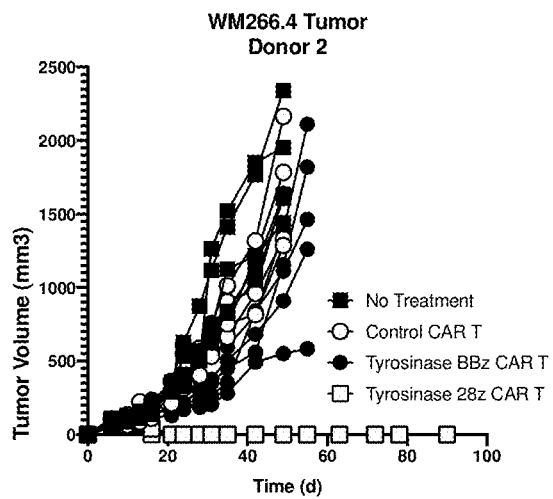

Example 4: Chimeric Antigen Receptors Containing Anti-HLA-A2/Tyrosinase$_{369-377}$ scFv Chimeric antigen receptors containing either an anti-HLA-A2/Tyrosinase$_{369-377}$ SCFV in the $V_L$-$V_H$ orientation plus either 1) a huCD8 hinge/transmembrane domain, a 4-1BB co-stimulatory domain, and a CD3z signaling domain (BB/z CAR), or 2) huCD28 hinge/transmembrane/costimulatory domains and a CD3z signaling domain (28/z CAR) were constructed using the $V_L$ and $V_H$ sequences of an anti-HLA-A2/Tyrosinase$_{369-377}$ antibody, D11 (identified from Patent WO/2016/199141). The anti-HLA-A2/Tyrosinase$_{369-377}$ antibody binds to both HLA-A2/Tyrosinase$_{369-377}$ as well as HLA-A2/Tyrosinase$_{369-377\,(N371D)}$, in which N371 is deamidated to D371. As a non-binding control, a BB/z CAR was designed using an irrelevant scFv plus a huCD8 hinge/transmembrane domain, a 4-1BB co-stimulatory domain, and a CD3z signaling domain. These CARs were cloned into a pLVX lentiviral vector with an EF1a promoter and P2A:eGFP sequence (for tracking CAR-transduced cells), and VSV-pseudotyped lentivirus was produced. See FIG. 5A for construct schematics.

Collectively, the results demonstrate that anti-HLA-A2/Tyrosinase$_{369-377}$ 28/z CAR T cells from two donors demonstrate superior in vivo anti-tumor activity and anti-tumor kinetics compared to anti-HLA-A2/Tyrosinase$_{369-377}$ BB/z CAR T cells.

TABLE 14

CAR scFv IDs:

| AbPID | AbPID | Specificity | Description |
|---|---|---|---|
| 17363 | 17363 | Non-binding control | Anti-HLA-A2/HPV16E7$_{11-19}$ scFv 17363 in VL-VH orientation with huCD8 hinge/transmembrane domain, a 4-1BB co-stimulatory domain, and a CD3z signaling domain (Control CAR) |
| D11 | D11 | HLA-A2/Tyrosinase$_{369-377}$ | Anti-HLA-A2/Tyrosinase$_{369-377}$ scFv D11 in VL-VH orientation with huCD8 hinge/transmembrane domain, a 4-1BB co-stimulatory domain, and a CD3z signaling domain (Tyrosinase$_{369-377}$ BB/z CAR) |
| D11 | D11 | HLA-A2/Tyrosinase$_{369-377}$ | Anti-HLA-A2/Tyrosinase$_{369-377}$ scFv D11 in VL-VH orientation with huCD28 hinge/transmembrane/co stimulatory domains and a CD3z signaling domain (Tyrosinase$_{369-377}$ 28/z CAR) |

TABLE 15

Lentivirus prep IDs:

| Lentivirus Prep # | AbPID | Date | Description |
|---|---|---|---|
| | 17363 | | Anti-HLA-A2/HPV16E7$_{11-19}$ scFv 17363 in VL-VH orientation with huCD8 hinge/transmembrane domain, a 4-1BB co-stimulatory domain, and a CD3z signaling domain (Control CAR) |
| | D11 | | Anti-HLA-A2/Tyrosinase$_{369-377}$ scFv D11 in VL-VH orientation with huCD8 hinge/transmembrane domain, a 4-1BB co-stimulatory domain, and a CD3z signaling domain (Tyrosinase$_{369-377}$ BB/z CAR) |
| | D11 | | Anti-HLA-A2/Tyrosinase$_{369-377}$ scFv D11 in VL-VH orientation with huCD28 hinge/transmembrane/costimulatory domains and a CD3z signaling domain (Tyrosinase$_{369-377}$ 28/z CAR) |

Experimental Procedure

Generation of CAR Constructs and CAR T Cells

Chimeric antigen receptors containing either an anti-HLA-A2/Tyrosinase$_{369-377}$ SCFV in the $V_L$-$V_H$ orientation plus either 1) a huCD8 hinge/transmembrane domain, a 4-1BB co-stimulatory domain, and a CD3z signaling domain (BB/z CAR), or 2) huCD28 hinge/transmembrane/costimulatory domains and a CD3z signaling domain (28/z CAR) were constructed using the $V_L$ and $V_H$ sequences of an anti-HLA-A2/Tyrosinase$_{369-377}$ antibody, D11 (identified from Patent WO/2016/199141). As a non-binding control, a BB/z CAR was designed using an irrelevant scFv plus a huCD8 hinge/transmembrane domain, a 4-1BB co-stimulatory domain, and a CD3z signaling domain. These CARs were cloned into a pLVX lentiviral vector with an EF1a promoter and P2A:eGFP sequence (for tracking CAR-transduced cells), and VSV-pseudotyped lentivirus was produced. See FIG. 5A for construct schematics.

CD3+ T cells were isolated from human peripheral blood mononuclear cells (PBMCs) from two normal donors ('Donor 1' and 'Donor 2'), stimulated with CD3/CD28 microbeads plus 100 U/ml recombinant human IL-2, and transduced with the lentivirus at an MOI=5. The transduced cells were expanded for 19 days with CD3/CD28 microbeads plus 100 U/ml recombinant human IL-2 before being cryopreserved until use during the in vivo experiment.

Implantation and Measurement of Xenogenic Tumors

To determine the in vivo efficacy of anti-HLA-A2/Tyrosinase$_{369-377}$-targeted chimeric antigen receptor (CAR) T cells, a xenogenic tumor study was performed. On day 0, immunodeficient NOD.Cg-Prkdc$^{scid}$Il2rg$^{tm1Wjl}$/SzJ (NSG) mice were subcutaneously injected with 4×10$^6$ HLA-A2$^+$Tyrosinase$^+$ WM266.4 human melanoma tumor cells. Using mass spectrometry techniques, it was determined that WM266.4 melanoma cells express approximately 4,500 cell-surface copies of the HLA-A2/Tyrosinase$_{369-377}$ peptide. On day 7 after tumors were established, the mice (n=5 per group) were intravenously injected with 2×10$^6$ T cells that express either the non-binding control BB/z CAR (Control CAR T), the anti-HLA-A2/Tyrosinase$_{369-377}$ BB/z CAR, or the anti-HLA-A2/Tyrosinase$_{369-377}$ 28/z CAR (as determined by the frequency of cells expressing GFP, which is a marker for those cells that have been transduced with CAR) from two different donors. Tumor growth was assessed through day 90 by measuring tumor volumes.

A second xenogenic tumor study was performed with a different tumor cell line. On day 0, immunodeficient NOD.Cg-Prkdc$^{scid}$Il2rg$^{tm1Wjl}$/SzJ (NSG) mice were subcutaneously injected with 5×10$^6$ HLA-A2$^+$Tyrosinase$^+$ SK-MEL-23 human melanoma tumor cells. Using mass spectrometry techniques, it was determined that SK-MEL-23 melanoma cells express approximately 2,000-3,000 cell-surface copies of the HLA-A2/Tyrosinase$_{369-377}$ peptide. On day 7 after tumors were established, the mice (n=5 per group) were intravenously injected with 4×10$^6$ T cells that express either the non-binding control BB/z CAR (Control CAR T), the anti-HLA-A2/Tyrosinase$_{369-377}$ BB/z CAR, or the anti-HLA-A2/Tyrosinase$_{369-377}$ 28/z CAR (as determined by the frequency of cells expressing GFP, which is a marker for those cells that have been transduced with CAR) from two different donors. Tumor growth was assessed through day 90 by measuring tumor volumes.

Calculation of Xenogenic Tumor Growth and Inhibition

In order to determine tumor volume by external caliper, the greatest longitudinal diameter (length in mm) and the greatest transverse diameter (width in mm) were determined. Tumor volumes based on caliper measurements were calculated by the formula: Volume (mm$^3$)=(length×width$^2$)/2.

Results Summary and Conclusions

WM266.4 Tumor Model:

Donor 1: WM266.4 tumors grew progressively in mice receiving no treatment and mice receiving Control CAR T cells. Mice receiving anti-HLA-A2/Tyrosinase$_{369-377}$ BB/z CAR T cells demonstrated modest efficacy, with reduced tumor growth compared to control on days 31 (p=0.02), 35 (p=0.001), 42 (p=0.0004), and 49 (p<0.0001) (statistics analyzed by 2-way ANOVA). By contrast, anti-HLA-A2/Tyrosinase$_{369-377}$ 28/z CAR T treatment led to regression of established WM266.4 tumors, with 4 of 5 mice remaining tumor-free through day 90. Enhanced efficacy of anti-HLA-A2/Tyrosinase$_{369-377}$ 28/z CAR vs. anti-HLA-A2/Tyrosinase$_{369-377}$ BB/z CAR is confirmed, as tumor sizes on days 35, 42, and 49 are statistically significant, (p=0.01, p<0.0001, and p<0.000, respectively) by 2-way ANOVA. See FIGS. 5B-5E.

Donor 2: WM266.4 tumors grew progressively in mice receiving no treatment and mice receiving Control CAR T cells. Mice receiving anti-HLA-A2/Tyrosinase$_{369-377}$ BB/z CAR T cells demonstrated modest efficacy, with reduced tumor growth compared to control on days 28 (p=0.03), 31 (p=0.004), 35 (p=0.0001), 42 (p=0.0001), and 49 (p<0.0001) (statistics analyzed by 2-way ANOVA). By contrast, anti-HLA-A2/Tyrosinase$_{369-377}$ 28/z CAR T treatment led to regression of established WM266.4 tumors, with 5 of 5 mice remaining tumor-free through day 90. Enhanced efficacy of anti-HLA-A2/Tyrosinase$_{369-377}$ 28/z CAR vs. anti-HLA-A2/Tyrosinase$_{369-377}$ BB/z CAR is confirmed, as tumor sizes on days 24, 28, 31, 35, 42, and 49 are statistically significant, (p=0.03, p=0.008, p=0.0004, p<0.0001, p<0.0001, and p<0.0001, respectively) by 2-way ANOVA. See FIGS. 5B-5E.

SK-MEL-23 Tumor Model:

Donor 1: SK-MEL-23 tumors grew progressively in mice receiving no treatment, and mice receiving Control CAR T cells. Mice receiving anti-HLA-A2/Tyrosinase$_{369-377}$ BB/z CAR T cells also grew progressively in a manner similar to the controls. By contrast, anti-HLA-A2/Tyrosinase$_{369-377}$ 28/z CAR T treatment led to significant inhibition of established SK-MEL-23 tumor growth on days 31 (p=0.02), 35 (p=0.004), 42 (p=0.0003), as well as days 49, 55, 63, 72, 78, and 90 (p<0.0001 for these days), compared to animals receiving Control CAR T cells (statistics analyzed by 2-way ANOVA). Enhanced efficacy of anti-HLA-A2/Tyrosinase$_{369-377}$ 28/z CAR vs. anti-HLA-A2/Tyrosinase$_{369-377}$ BB/z CAR is confirmed, as tumor sizes on days 35, 42, 49, 55, 63, 72, 78, and 90 are statistically significant (p=0.04 and p=0.004 on days 35 and 42; p<0.0001 for all other days) by 2-way ANOVA test. See FIGS. 5F-5I.

Donor 2: SK-MEL-23 tumors grew progressively in mice receiving no treatment, and mice receiving Control CAR T cells. Mice receiving anti-HLA-A2/Tyrosinase$_{369-377}$ BB/z CAR T cells also grew progressively in a manner similar to the controls. By contrast, anti-HLA-A2/Tyrosinase$_{369-377}$ 28/z CAR T treatment led to a reduction in size of established SK-MEL-23 tumors and suppression of tumor growth on days 21 (p=0.02), 24 (p=0.004), and 28 (p=0.0004), as well as days 31, 35, 42, 49, 55, 63, 72, 78, and 90 (p<0.0001 for these days), compared to animals receiving Control CAR T cells (statistics analyzed by 2-way ANOVA). Enhanced efficacy of anti-HLA-A2/Tyrosinase$_{369-377}$ 28/z CAR vs. anti-HLA-A2/Tyrosinase$_{369-377}$ BB/z CAR is confirmed, as tumor sizes on days 21, 24, 28, 31, 35, 42, 49, 55, 63, 72, 78, and 90 are statistically significant (p=0.01 and p=0.005 on days 21 and 24; p<0.0001 for all other days) by 2-way ANOVA test.

TABLE 16

Data Summary:

| CAR T Treatment | Average Tumor Size (mm³) on Day 6 | Tumor size standard error of the mean (SEM) | Number of mice still alive (of 5) on day 6 |
| --- | --- | --- | --- |
| WM266.4: No Treatment | 75.8 | 10.4 | 5 |
| WM266.4: Donor 1: Control CAR T | 72.0 | 4.5 | 5 |
| WM266.4: Donor 1: Tyrosinase$_{369-377}$ BB/z CAR T | 75.3 | 6.7 | 5 |
| WM266.4: Donor 1: Tyrosinase$_{369-377}$ 28/z CAR T | 66.0 | 2.9 | 5 |
| WM266.4: Donor 2: Control CAR T | 79.7 | 8.9 | 5 |
| WM266.4: Donor 2: Tyrosinase$_{369-377}$ BB/z CAR T | 73.6 | 6.7 | 5 |
| WM266.4: Donor 2: Tyrosinase$_{369-377}$ 28/z CAR T | 71.8 | 6.5 | 5 |
| SK-MEL-23: No Treatment | 50.8 | 4.9 | 5 |
| SK-MEL-23: Donor 1: Control CAR T | 46.9 | 3.0 | 5 |
| SK-MEL-23: Donor 1: Tyrosinase$_{369-377}$ BB/z CAR T | 46.3 | 1.2 | 5 |
| SK-MEL-23: Donor 1: Tyrosinase$_{369-377}$ 28/z CAR T | 48.9 | 6.7 | 5 |
| SK-MEL-23: Donor 2: Control CAR T | 48.7 | 5.4 | 5 |
| SK-MEL-23: Donor 2: Tyrosinase$_{369-377}$ BB/z CAR T | 54.0 | 4.8 | 5 |
| SK-MEL-23: Donor 2: Tyrosinase$_{369-377}$ 28/z CAR T | 49.4 | 5.7 | 5 |

| CAR T Treatment | Average Tumor Size (mm³) on Day 10 | Tumor size standard error of the mean (SEM) | Number of mice still alive (of 5) on day 0 |
| --- | --- | --- | --- |
| WM266.4: No Treatment | 99.6 | 6.7 | 5 |
| WM266.4: Donor 1: Control CAR T | 111.7 | 23.2 | 5 |
| WM266.4: Donor 1: Tyrosinase$_{369-377}$ BB/z CAR T | 79.6 | 8.3 | 5 |
| WM266.4: Donor 1: Tyrosinase$_{369-377}$ 28/z CAR T | 78.6 | 7.0 | 5 |
| WM266.4: Donor 2: Control CAR T | 96.1 | 14.8 | 5 |
| WM266.4: Donor 2: Tyrosinase$_{369-377}$ BB/z CAR T | 88.7 | 4.5 | 5 |
| WM266.4: Donor 2: Tyrosinase$_{369-377}$ 28/z CAR T | 83.3 | 11.1 | 5 |
| SK-MEL-23: No Treatment | 58.5 | 4.0 | 5 |
| SK-MEL-23: Donor 1: Control CAR T | 55.8 | 5.2 | 5 |

TABLE 16-continued

Data Summary:

| | | | |
|---|---|---|---|
| SK-MEL-23: Donor 1: Tyrosinase$_{369-377}$ BB/z CAR T | 51.5 | 2.5 | 5 |
| SK-MEL-23: Donor 1: Tyrosinase$_{369-377}$ 28/z CAR T | 51.0 | 8.4 | 5 |
| SK-MEL-23: Donor 2: Control CAR T | 54.0 | 8.2 | 5 |
| SK-MEL-23: Donor 2: Tyrosinase$_{369-377}$ BB/z CAR T | 58.3 | 2.4 | 5 |
| SK-MEL-23: Donor 2: Tyrosinase$_{369-377}$ 28/z CAR T | 53.7 | 7.1 | 5 |

| CAR T Treatment | Average Tumor Size (mm$^3$) on Day 3 | Tumor size standard error of the mean (SEM) | Number of mice still alive (of 5) on day 3 |
|---|---|---|---|
| WM266.4: No Treatment | 132.0 | 7.6 | 5 |
| WM266.4: Donor 1: Control CAR T | 149.3 | 19.4 | 5 |
| WM266.4: Donor 1: Tyrosinase$_{369-377}$ BB/z CAR T | 123.5 | 10.5 | 5 |
| WM266.4: Donor 1: Tyrosinase$_{369-377}$ 28/z CAR T | 132.3 | 19.4 | 5 |
| WM266.4: Donor 2: Control CAR T | 143.9 | 22.8 | 5 |
| WM266.4: Donor 2: Tyrosinase$_{369-377}$ BB/z CAR T | 145.8 | 7.2 | 5 |
| WM266.4: Donor 2: Tyrosinase$_{369-377}$ 28/z CAR T | 86.7 | 6.5 | 5 |
| SK-MEL-23: No Treatment | 90.3 | 12.9 | 5 |
| SK-MEL-23: Donor 1: Control CAR T | 76.5 | 4.6 | 5 |
| SK-MEL-23: Donor 1: Tyrosinase$_{369-377}$ BB/z CAR T | 87.0 | 5.0 | 5 |
| SK-MEL-23: Donor 1: Tyrosinase$_{369-377}$ 28/z CAR T | 69.1 | 7.3 | 5 |
| SK-MEL-23: Donor 2: Control CAR T | 73.9 | 7.1 | 5 |
| SK-MEL-23: Donor 2: Tyrosinase$_{369-377}$ BB/z CAR T | 88.3 | 3.8 | 5 |
| SK-MEL-23: Donor 2: Tyrosinase$_{369-377}$ 28/z CAR T | 47.5 | 6.5 | 5 |

| CAR T Treatment | Average Tumor Size (mm$^3$) on Day 16 | Tumor size standard error of the mean (SEM) | Number of mice still alive (of 5) on day 16 |
|---|---|---|---|
| WM266.4: No Treatment | 180.1 | 11.9 | 5 |
| WM266.4: Donor 1: Control CAR T | 172.5 | 15.1 | 5 |
| WM266.4: Donor 1: Tyrosinase$_{369-377}$ BB/z CAR T | 168.7 | 20.9 | 5 |
| WM266.4: Donor 1: Tyrosinase$_{369-377}$ 28/z CAR T | 114.2 | 22.5 | 5 |
| WM266.4: Donor 2: Control CAR T | 167.0 | 18.1 | 5 |
| WM266.4: Donor 2: Tyrosinase$_{369-377}$ BB/z CAR T | 175.5 | 20.5 | 5 |
| WM266.4: Donor 2: Tyrosinase$_{369-377}$ 28/z CAR T | 32.2 | 9.3 | 5 |
| SK-MEL-23: No Treatment | 120.2 | 18.3 | 5 |
| SK-MEL-23: Donor 1: Control CAR T | 107.1 | 12.2 | 5 |
| SK-MEL-23: Donor 1: Tyrosinase$_{369-377}$ BB/z CAR T | 98.0 | 9.8 | 5 |
| SK-MEL-23: Donor 1: Tyrosinase$_{369-377}$ 28/z CAR T | 65.9 | 7.7 | 5 |
| SK-MEL-23: Donor 2: Control CAR T | 89.9 | 13.2 | 5 |
| SK-MEL-23: Donor 2: Tyrosinase$_{369-377}$ BB/z CAR T | 100.5 | 6.4 | 5 |
| SK-MEL-23: Donor 2: Tyrosinase$_{369-377}$ 28/z CAR T | 29.9 | 3.8 | 5 |

| CAR T Treatment | Average Tumor Size (mm$^3$) on Day 21 | Tumor size standard error of the mean (SEM) | Number of mice still alive (of 5) on day 21 |
|---|---|---|---|
| WM266.4: No Treatment | 320.9 | 11.8 | 5 |
| WM266.4: Donor 1: Control CAR T | 312.7 | 34.8 | 5 |
| WM266.4: Donor 1: Tyrosinase$_{369-377}$ BB/z CAR T | 197.4 | 25.5 | 5 |

TABLE 16-continued

Data Summary:

| | | | |
|---|---|---|---|
| WM266.4: Donor 1: Tyrosinase$_{369-377}$ 28/z CAR T | 39.2 | 5.8 | 5 |
| WM266.4: Donor 2: Control CAR T | 303.6 | 27.9 | 5 |
| WM266.4: Donor 2: Tyrosinase$_{369-377}$ BB/z CAR T | 184.2 | 22.9 | 5 |
| WM266.4: Donor 2: Tyrosinase$_{369-377}$ 28/z CAR T | 0.0 | 0.0 | 5 |
| SK-MEL-23: No Treatment | 146.9 | 14.5 | 5 |
| SK-MEL-23: Donor 1: Control CAR T | 148.9 | 18.6 | 5 |
| SK-MEL-23: Donor 1: Tyrosinase$_{369-377}$ BB/z CAR T | 105.7 | 13.6 | 5 |
| SK-MEL-23: Donor 1: Tyrosinase$_{369-377}$ 28/z CAR T | 49.9 | 5.1 | 5 |
| SK-MEL-23: Donor 2: Control CAR T | 125.5 | 14.3 | 5 |
| SK-MEL-23: Donor 2: Tyrosinase$_{369-377}$ BB/z CAR T | 135.4 | 9.5 | 5 |
| SK-MEL-23: Donor 2: Tyrosinase$_{369-377}$ 28/z CAR T | 11.0 | 6.8 | 5 |

| CAR T Treatment | Average Tumor Size (mm$^3$) on Day 24 | Tumor size standard error of the mean (SEM) | Number of mice still alive (of 5) on day 24 |
|---|---|---|---|
| WM266.4: No Treatment | 457.8 | 53.3 | 5 |
| WM266.4: Donor 1: Control CAR T | 566.0 | 103.8 | 5 |
| WM266.4: Donor 1: Tyrosinase$_{369-377}$ BB/z CAR T | 234.8 | 35.4 | 5 |
| WM266.4: Donor 1: Tyrosinase$_{369-377}$ 28/z CAR T | 37.4 | 9.2 | 5 |
| WM266.4: Donor 2: Control CAR T | 455.4 | 57.0 | 5 |
| WM266.4: Donor 2: Tyrosinase$_{369-377}$ BB/z CAR T | 235.9 | 38.4 | 5 |
| WM266.4: Donor 2: Tyrosinase$_{369-377}$ 28/z CAR T | 0.0 | 0.0 | 5 |
| SK-MEL-23: No Treatment | 180.4 | 14.5 | 5 |
| SK-MEL-23: Donor 1: Control CAR T | 195.1 | 29.7 | 5 |
| SK-MEL-23: Donor 1: Tyrosinase$_{369-377}$ BB/z CAR T | 132.6 | 15.0 | 5 |
| SK-MEL-23: Donor 1: Tyrosinase$_{369-377}$ 28/z CAR T | 57.3 | 6.7 | 5 |
| SK-MEL-23: Donor 2: Control CAR T | 144.5 | 17.1 | 5 |
| SK-MEL-23: Donor 2: Tyrosinase$_{369-377}$ BB/z CAR T | 165.4 | 9.9 | 5 |
| SK-MEL-23: Donor 2: Tyrosinase$_{369-377}$ 28/z CAR T | 7.9 | 7.9 | 5 |

| CAR T Treatment | Average Tumor Size (mm$^3$) on Day 28 | Tumor size standard error of the mean (SEM) | Number of mice still alive (of 5) on day 28 |
|---|---|---|---|
| WM266.4: No Treatment | 594.7 | 71.0 | 5 |
| WM266.4: Donor 1: Control CAR T | 705.0 | 168.3 | 5 |
| WM266.4: Donor 1: Tyrosinase$_{369-377}$ BB/z CAR T | 301.7 | 37.5 | 5 |
| WM266.4: Donor 1: Tyrosinase$_{369-377}$ 28/z CAR T | 21.2 | 9.3 | 5 |
| WM266.4: Donor 2: Control CAR T | 517.3 | 30.7 | 5 |
| WM266.4: Donor 2: Tyrosinase$_{369-377}$ BB/z CAR T | 276.9 | 32.2 | 5 |
| WM266.4: Donor 2: Tyrosinase$_{369-377}$ 28/z CAR T | 0.0 | 0.0 | 5 |
| SK-MEL-23: No Treatment | 207.9 | 16.1 | 5 |
| SK-MEL-23: Donor 1: Control CAR T | 217.0 | 47.0 | 5 |
| SK-MEL-23: Donor 1: Tyrosinase$_{369-377}$ BB/z CAR T | 153.7 | 22.6 | 5 |
| SK-MEL-23: Donor 1: Tyrosinase$_{369-377}$ 28/z CAR T | 68.1 | 16.1 | 5 |
| SK-MEL-23: Donor 2: Control CAR T | 160.5 | 18.6 | 5 |
| SK-MEL-23: Donor 2: Tyrosinase$_{369-377}$ BB/z CAR T | 197.8 | 16.5 | 5 |
| SK-MEL-23: Donor 2: Tyrosinase$_{369-377}$ 28/z CAR T | 0.0 | 0.0 | 5 |

TABLE 16-continued

Data Summary:

| CAR T Treatment | Average Tumor Size (mm³) on Day 31 | Tumor size standard error of the mean (SEM) | Number of mice still alive (of 5) on day 31 |
|---|---|---|---|
| WM266.4: No Treatment | 893.7 | 124.8 | 5 |
| WM266.4: Donor 1: Control CAR T | 850.9 | 162.0 | 5 |
| WM266.4: Donor 1: Tyrosinase$_{369-377}$ BB/z CAR T | 369.1 | 40.1 | 5 |
| WM266.4: Donor 1: Tyrosinase$_{369-377}$ 28/z CAR T | 12.9 | 7.9 | 5 |
| WM266.4: Donor 2: Control CAR T | 646.0 | 42.2 | 5 |
| WM266.4: Donor 2: Tyrosinase$_{369-377}$ BB/z CAR T | 352.2 | 60.6 | 5 |
| WM266.4: Donor 2: Tyrosinase$_{369-377}$ 28/z CAR T | 0.0 | 0.0 | 5 |
| SK-MEL-23: No Treatment | 232.8 | 13.0 | 5 |
| SK-MEL-23: Donor 1: Control CAR T | 271.1 | 24.9 | 5 |
| SK-MEL-23: Donor 1: Tyrosinase$_{369-377}$ BB/z CAR T | 196.1 | 16.0 | 5 |
| SK-MEL-23: Donor 1: Tyrosinase$_{369-377}$ 28/z CAR T | 79.9 | 21.7 | 5 |
| SK-MEL-23: Donor 2: Control CAR T | 192.5 | 17.8 | 5 |
| SK-MEL-23: Donor 2: Tyrosinase$_{369-377}$ BB/z CAR T | 256.1 | 19.6 | 5 |
| SK-MEL-23: Donor 2: Tyrosinase$_{369-377}$ 28/z CAR T | 0.0 | 0.0 | 5 |

| CAR T Treatment | Average Tumor Size (mm³) on Day 35 | Tumor size standard error of the mean (SEM) | Number of mice still alive (of 5) on day 35 |
|---|---|---|---|
| WM266.4: No Treatment | 1145.0 | 143.1 | 5 |
| WM266.4: Donor 1: Control CAR T | 1160.0 | 216.4 | 5 |
| WM266.4: Donor 1: Tyrosinase$_{369-377}$ BB/z CAR T | 533.6 | 127.4 | 5 |
| WM266.4: Donor 1: Tyrosinase$_{369-377}$ 28/z CAR T | 13.7 | 9.0 | 5 |
| WM266.4: Donor 2: Control CAR T | 813.2 | 63.1 | 5 |
| WM266.4: Donor 2: Tyrosinase$_{369-377}$ BB/z CAR T | 436.8 | 55.2 | 5 |
| WM266.4: Donor 2: Tyrosinase$_{369-377}$ 28/z CAR T | 0.0 | 0.0 | 5 |
| SK-MEL-23: No Treatment | 258.3 | 25.0 | 5 |
| SK-MEL-23: Donor 1: Control CAR T | 320.4 | 42.4 | 5 |
| SK-MEL-23: Donor 1: Tyrosinase$_{369-377}$ BB/z CAR T | 265.3 | 19.8 | 5 |
| SK-MEL-23: Donor 1: Tyrosinase$_{369-377}$ 28/z CAR T | 88.1 | 21.9 | 5 |
| SK-MEL-23: Donor 2: Control CAR T | 205.7 | 16.0 | 5 |
| SK-MEL-23: Donor 2: Tyrosinase$_{369-377}$ BB/z CAR T | 289.9 | 15.0 | 5 |
| SK-MEL-23: Donor 2: Tyrosinase$_{369-377}$ 28/z CAR T | 0.0 | 0.0 | 5 |

| CAR T Treatment | Average Tumor Size (mm³) on Day 42 | Tumor size standard error of the mean (SEM) | Number of mice still alive (of 5) on day 42 |
|---|---|---|---|
| WM266.4: No Treatment | 1405.3 | 167.6 | 5 |
| WM266.4: Donor 1: Control CAR T | 1460.2 | 348.8 | 5 |
| WM266.4: Donor 1: Tyrosinase$_{369-377}$ BB/z CAR T | 787.1 | 235.7 | 5 |
| WM266.4: Donor 1: Tyrosinase$_{369-377}$ 28/z CAR T | 9.8 | 6.7 | 5 |
| WM266.4: Donor 2: Control CAR T | 1058.5 | 90.7 | 5 |
| WM266.4: Donor 2: Tyrosinase$_{369-377}$ BB/z CAR T | 679.0 | 68.9 | 5 |
| WM266.4: Donor 2: Tyrosinase$_{369-377}$ 28/z CAR T | 0.0 | 0.0 | 5 |
| SK-MEL-23: No Treatment | 323.8 | 46.1 | 5 |
| SK-MEL-23: Donor 1: Control CAR T | 367.8 | 47.4 | 5 |

TABLE 16-continued

Data Summary:

| | | | |
|---|---|---|---|
| SK-MEL-23: Donor 1: Tyrosinase$_{369-377}$ BB/z CAR T | 321.2 | 12.2 | 5 |
| SK-MEL-23: Donor 1: Tyrosinase$_{369-377}$ 28/z CAR T | 89.8 | 21.3 | 5 |
| SK-MEL-23: Donor 2: Control CAR T | 231.4 | 22.7 | 5 |
| SK-MEL-23: Donor 2: Tyrosinase$_{369-377}$ BB/z CAR T | 353.3 | 20.3 | 5 |
| SK-MEL-23: Donor 2: Tyrosinase$_{369-377}$ 28/z CAR T | 13.3 | 8.6 | 5 |

| CAR T Treatment | Average Tumor Size (mm$^3$) on Day 49 | Tumor size standard error of the mean (SEM) | Number of mice still alive (of 5) on day 49 |
|---|---|---|---|
| WM266.4: No Treatment | 1795.4 | 159.4 | 5 |
| WM266.4: Donor 1: Control CAR T | 2031.6 | 455.2 | 5 |
| WM266.4: Donor 1: Tyrosinase$_{369-377}$ BB/z CAR T | 1134.8 | 200.1 | 5 |
| WM266.4: Donor 1: Tyrosinase$_{369-377}$ 28/z CAR T | 0.0 | 0.0 | 5 |
| WM266.4: Donor 2: Control CAR T | 1639.4 | 160.8 | 5 |
| WM266.4: Donor 2: Tyrosinase$_{369-377}$ BB/z CAR T | 1022.2 | 139.6 | 5 |
| WM266.4: Donor 2: Tyrosinase$_{369-377}$ 28/z CAR T | 0.0 | 0.0 | 5 |
| SK-MEL-23: No Treatment | 378.4 | 36.3 | 5 |
| SK-MEL-23: Donor 1: Control CAR T | 443.9 | 69.3 | 5 |
| SK-MEL-23: Donor 1: Tyrosinase$_{369-377}$ BB/z CAR T | 410.7 | 34.4 | 5 |
| SK-MEL-23: Donor 1: Tyrosinase$_{369-377}$ 28/z CAR T | 114.3 | 27.5 | 5 |
| SK-MEL-23: Donor 2: Control CAR T | 288.8 | 18.6 | 5 |
| SK-MEL-23: Donor 2: Tyrosinase$_{369-377}$ BB/z CAR T | 467.6 | 47.4 | 5 |
| SK-MEL-23: Donor 2: Tyrosinase$_{369-377}$ 28/z CAR T | 28.2 | 7.3 | 5 |

| CAR T Treatment | Average Tumor Size (mm$^3$) on Day 55 | Tumor size standard error of the mean (SEM) | Number of mice still alive (of 5) on day 55 |
|---|---|---|---|
| WM266.4: No Treatment | Euthanized | Euthanized | 0 |
| WM266.4: Donor 1: Control CAR T | Euthanized | Euthanized | 0 |
| WM266.4: Donor 1: Tyrosinase$_{369-377}$ BB/z CAR T | Euthanized | Euthanized | 0 |
| WM266.4: Donor 1: Tyrosinase$_{369-377}$ 28/z CAR T | 0.0 | 0.0 | 5 |
| WM266.4: Donor 2: Control CAR T | Euthanized | Euthanized | 0 |
| WM266.4: Donor 2: Tyrosinase$_{369-377}$ BB/z CAR T | 1448.1 | 261.0 | 5 |
| WM266.4: Donor 2: Tyrosinase$_{369-377}$ 28/z CAR T | 0.0 | 0.0 | 5 |
| SK-MEL-23: No Treatment | 452.8 | 37.4 | 5 |
| SK-MEL-23: Donor 1: Control CAR T | 467.6 | 56.5 | 5 |
| SK-MEL-23: Donor 1: Tyrosinase$_{369-377}$ BB/z CAR T | 500.0 | 21.1 | 5 |
| SK-MEL-23: Donor 1: Tyrosinase$_{369-377}$ 28/z CAR T | 141.5 | 53.8 | 5 |
| SK-MEL-23: Donor 2: Control CAR T | 341.3 | 28.1 | 5 |
| SK-MEL-23: Donor 2: Tyrosinase$_{369-377}$ BB/z CAR T | 596.7 | 40.0 | 5 |
| SK-MEL-23: Donor 2: Tyrosinase$_{369-377}$ 28/z CAR T | 53.2 | 17.0 | 5 |

| CAR T Treatment | Average Tumor Size (mm$^3$) on Day 63 | Tumor size standard error of the mean (SEM) | Number of mice still alive (of 5) on day 63 |
|---|---|---|---|
| WM266.4: No Treatment | Euthanized | Euthanized | 0 |
| WM266.4: Donor 1: Control CAR T | Euthanized | Euthanized | 0 |
| WM266.4: Donor 1: Tyrosinase$_{369-377}$ BB/z CAR T | Euthanized | Euthanized | 0 |

TABLE 16-continued

Data Summary:

| Treatment | | | |
|---|---|---|---|
| WM266.4: Donor 1: Tyrosinase$_{369-377}$ 28/z CAR T | 0 | 0 | 5 |
| WM266.4: Donor 2: Control CAR T | Euthanized | Euthanized | 0 |
| WM266.4: Donor 2: Tyrosinase$_{369-377}$ BB/z CAR T | Euthanized | Euthanized | 0 |
| WM266.4: Donor 2: Tyrosinase$_{369-377}$ 28/z CAR T | 0 | 0 | 5 |
| SK-MEL-23: No Treatment | 516.4 | 34.1 | 5 |
| SK-MEL-23: Donor 1: Control CAR T | 537.1 | 63.5 | 5 |
| SK-MEL-23: Donor 1: Tyrosinase$_{369-377}$ BB/z CAR T | 602.4 | 30.9 | 5 |
| SK-MEL-23: Donor 1: Tyrosinase$_{369-377}$ 28/z CAR T | 214.2 | 81.8 | 5 |
| SK-MEL-23: Donor 2: Control CAR T | 487.6 | 41.4 | 5 |
| SK-MEL-23: Donor 2: Tyrosinase$_{369-377}$ BB/z CAR T | 767.7 | 45.5 | 5 |
| SK-MEL-23: Donor 2: Tyrosinase$_{369-377}$ 28/z CAR T | 111.6 | 38.2 | 5 |

| CAR T Treatment | Average Tumor Size (mm$^3$) on Day 72 | Tumor size standard error of the mean (SEM) | Number of mice still alive (of 5) on day 72 |
|---|---|---|---|
| WM266.4: No Treatment | Euthanized | Euthanized | 0 |
| WM266.4: Donor 1: Control CAR T | Euthanized | Euthanized | 0 |
| WM266.4: Donor 1: Tyrosinase$_{369-377}$ BB/z CAR T | Euthanized | Euthanized | 0 |
| WM266.4: Donor 1: Tyrosinase$_{369-377}$ 28/z CAR T | 0 | 0 | 5 |
| WM266.4: Donor 2: Control CAR T | Euthanized | Euthanized | 0 |
| WM266.4: Donor 2: Tyrosinase$_{369-377}$ BB/z CAR T | Euthanized | Euthanized | 0 |
| WM266.4: Donor 2: Tyrosinase$_{369-377}$ 28/z CAR T | 0 | 0 | 5 |
| SK-MEL-23: No Treatment | 521.4 | 20.0 | 5 |
| SK-MEL-23: Donor 1: Control CAR T | 716.6 | 94.7 | 5 |
| SK-MEL-23: Donor 1: Tyrosinase$_{369-377}$ BB/z CAR T | 747.2 | 30.5 | 5 |
| SK-MEL-23: Donor 1: Tyrosinase$_{369-377}$ 28/z CAR T | 281.7 | 106.0 | 5 |
| SK-MEL-23: Donor 2: Control CAR T | 546.2 | 38.4 | 5 |
| SK-MEL-23: Donor 2: Tyrosinase$_{369-377}$ BB/z CAR T | 856.0 | 45.5 | 5 |
| SK-MEL-23: Donor 2: Tyrosinase$_{369-377}$ 28/z CAR T | 136.9 | 49.1 | 5 |

| CAR T Treatment | Average Tumor Size (mm$^3$) on Day 78 | Tumor size standard error of the mean (SEM) | Number of mice still alive (of 5) on day 78 |
|---|---|---|---|
| WM266.4: No Treatment | Euthanized | Euthanized | 0 |
| WM266.4: Donor 1: Control CAR T | Euthanized | Euthanized | 0 |
| WM266.4: Donor 1: Tyrosinase$_{369-377}$ BB/z CAR T | Euthanized | Euthanized | 0 |
| WM266.4: Donor 1: Tyrosinase$_{369-377}$ 28/z CAR T | 0 | 0 | 5 |
| WM266.4: Donor 2: Control CAR T | Euthanized | Euthanized | 0 |
| WM266.4: Donor 2: Tyrosinase$_{369-377}$ BB/z CAR T | Euthanized | Euthanized | 0 |
| WM266.4: Donor 2: Tyrosinase$_{369-377}$ 28/z CAR T | 0 | 0 | 5 |
| SK-MEL-23: No Treatment | 671.6 | 37.6 | 5 |
| SK-MEL-23: Donor 1: Control CAR T | 806.8 | 87.2 | 5 |
| SK-MEL-23: Donor 1: Tyrosinase$_{369-377}$ BB/z CAR T | 855.2 | 50.2 | 5 |
| SK-MEL-23: Donor 1: Tyrosinase$_{369-377}$ 28/z CAR T | 374.6 | 119.6 | 5 |
| SK-MEL-23: Donor 2: Control CAR T | 637.2 | 34.8 | 5 |
| SK-MEL-23: Donor 2: Tyrosinase$_{369-377}$ BB/z CAR T | 988.5 | 47.0 | 5 |
| SK-MEL-23: Donor 2: Tyrosinase$_{369-377}$ 28/z CAR T | 152.0 | 42.6 | 5 |

TABLE 16-continued

Data Summary:

| CAR T Treatment | Average Tumor Size (mm$^3$) on Day 90 | Tumor size standard error of the mean (SEM) | Number of mice still alive (of 5) on day 90 |
|---|---|---|---|
| WM266.4: No Treatment | Euthanized | Euthanized | 0 |
| WM266.4: Donor 1: Control CAR T | Euthanized | Euthanized | 0 |
| WM266.4: Donor 1: Tyrosinase$_{369-377}$ BB/z CAR T | Euthanized | Euthanized | 0 |
| WM266.4: Donor 1: Tyrosinase$_{369-377}$ 28/z CAR T | 0 | 0 | 5 |
| WM266.4: Donor 2: Control CAR T | Euthanized | Euthanized | 0 |
| WM266.4: Donor 2: Tyrosinase$_{369-377}$ BB/z CAR T | Euthanized | Euthanized | 0 |
| WM266.4: Donor 2: Tyrosinase$_{369-377}$ 28/z CAR T | 0 | 0 | 5 |
| SK-MEL-23: No Treatment | 826.9 | 44.7 | 5 |
| SK-MEL-23: Donor 1: Control CAR T | 977.9 | 114.0 | 5 |
| SK-MEL-23: Donor 1: Tyrosinase$_{369-377}$ BB/z CAR T | 1193.5 | 97.3 | 5 |
| SK-MEL-23: Donor 1: Tyrosinase$_{369-377}$ 28/z CAR T | 600.9 | 191.1 | 5 |
| SK-MEL-23: Donor 2: Control CAR T | 917.2 | 80.1 | 5 |
| SK-MEL-23: Donor 2: Tyrosinase$_{369-377}$ BB/z CAR T | 1208.2 | 71.4 | 5 |
| SK-MEL-23: Donor 2: Tyrosinase$_{369-377}$ 28/z CAR T | 258.9 | 62.6 | 5 |

Figure 6A:
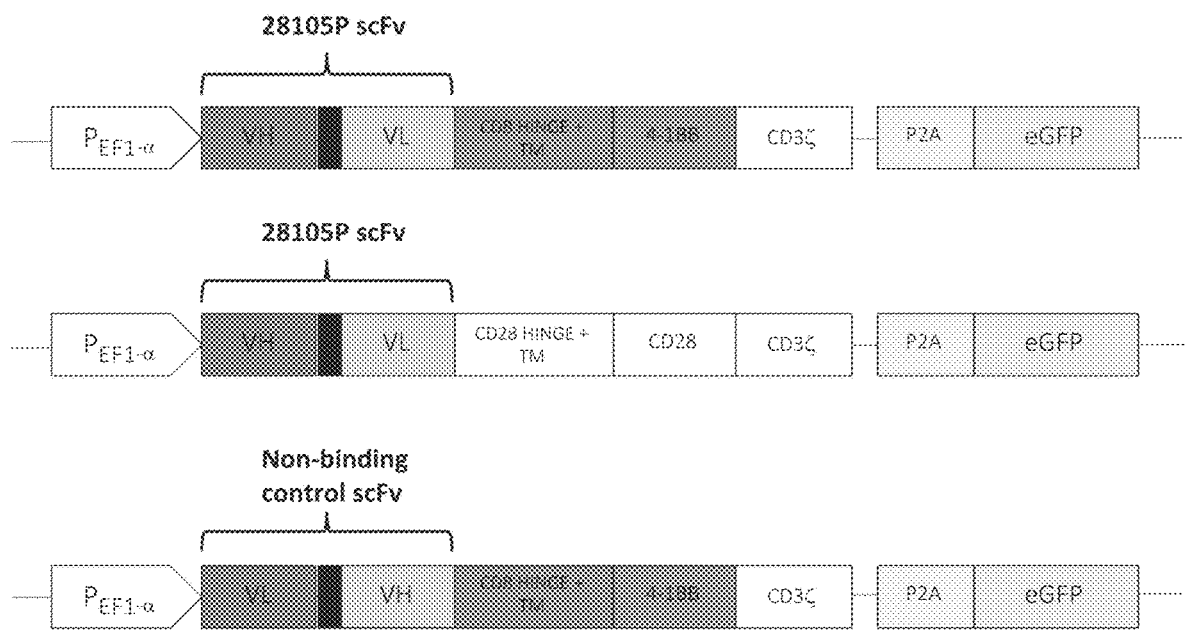
FIGS. 6A-6E show exemplary CAR constructs used in Example 5 and that NY-ESO-1$_{157-165}$ 28/z CAR T cells demonstrate superior in vivo anti-tumor activity and anti-tumor kinetics compared to NY-ESO-1$_{157-165}$ BB/z CAR T cells in the A375 melanoma tumor model.
Figure 6B:
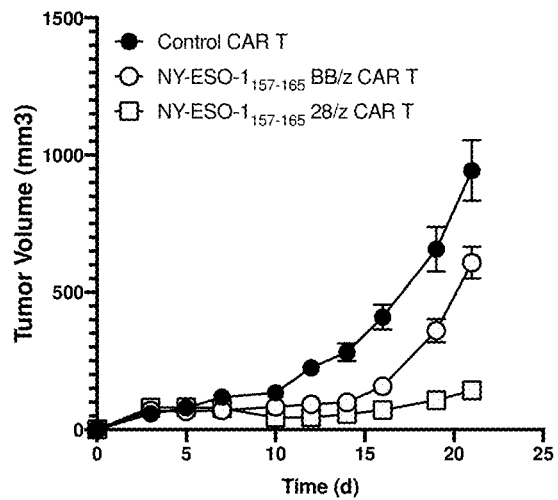
Figure 6C:
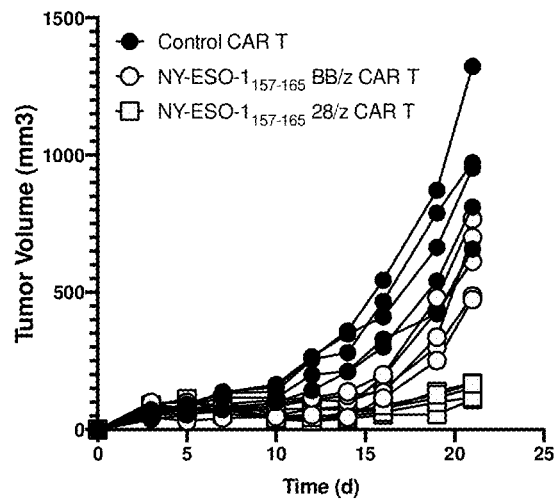
Figure 6D:
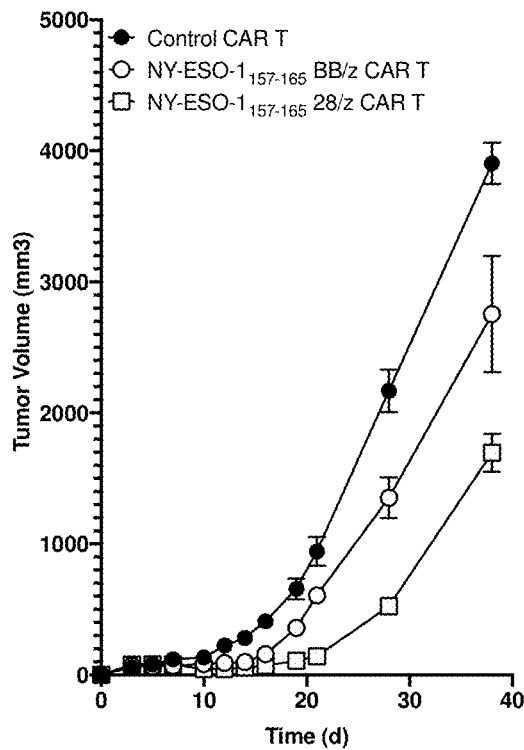
Figure 6E:
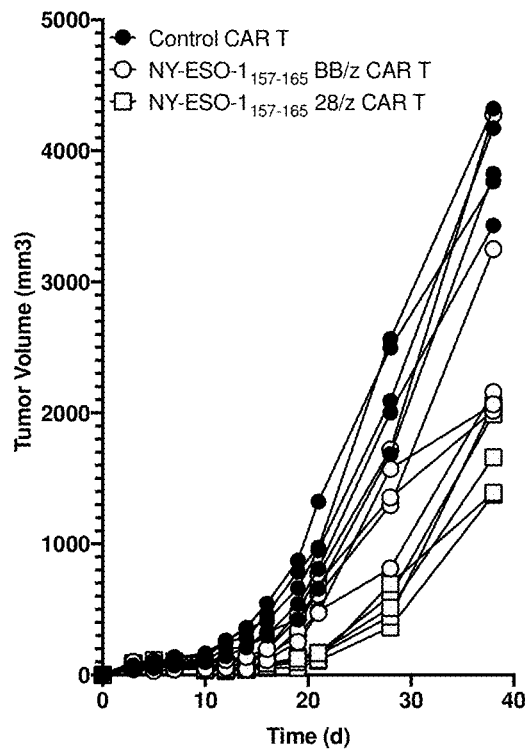

Example 5: Chimeric Antigen Receptors Containing Anti-HLA-A2/NY-ESO-1$_{157-165}$ scFv Chimeric antigen receptors containing either an anti-HLA-A2/NY-ESO-1$_{157-165}$ SCFV in the $V_H$-$V_L$ orientation plus either 1) a huCD8 hinge/transmembrane domain, a 4-1BB co-stimulatory domain, and a CD3z signaling domain (BB/z CAR), or 2) huCD28 hinge/transmembrane/costimulatory domains and a CD3z signaling domain (28/z CAR) were constructed using the $V_L$ and $V_H$ sequences of an anti-HLA-A2/NY-ESO-1$_{157-165}$ antibody, 28105P. As a non-binding control, a BB/z CAR was designed using an irrelevant scFv plus a huCD8 hinge/transmembrane domain, a 4-1BB co-stimulatory domain, and a CD3z signaling domain. These CARs were cloned into a pLVX lentiviral vector with an EF1a promoter and P2A:eGFP sequence (for tracking CAR-transduced cells), and VSV-pseudotyped lentivirus was produced. See FIG. 6A for construct design and FIGS. 6B-6E for results.

Collectively, the results demonstrate that anti-HLA-A2/NY-ESO-1$_{157-165}$ 28/z CAR T cells demonstrate superior in vivo anti-tumor activity and anti-tumor kinetics compared to anti-HLA-A2/NY-ESO-1$_{157-165}$ BB/z CAR T cells.

TABLE 17

CAR scFv IDs:

| AbPID | AbPID | Specificity | Description |
|---|---|---|---|
| 17363 | 17363 | Non-binding control | Anti-HLA-A2/HPV16E7$_{11-19}$ scFv 17363 in VL-VH orientation with huCD8 hinge/transmembrane domain, a 4-1BB co-stimulatory domain, and a CD3z signaling domain (Control CAR) |
| 28105P | 28105P | HLA-A2/NY-ESO-1$_{157-165}$ | anti-HLA-A2/NY-ESO-1$_{157-165}$ scFv 28105P in VH-VL orientation with huCD8 hinge/transmembrane domain, a 4-1BB co-stimulatory domain, and a CD3z signaling domain (NY-ESO-1$_{157-165}$ BB/z CAR) |
| 28105P | 28105P | HLA-A2/NY-ESO-1$_{157-165}$ | anti-HLA-A2/NY-ESO-1$_{157-165}$ scFv 28105P in VH-VL orientation with huCD28 hinge/transmembrane/costimulatory domains and a CD3z signaling domain (NY-ESO-1$_{157-165}$ 28/z CAR) |

TABLE 18

Lentivirus prep IDs:

| Lentivirus Prep # | AbPID | Date | Description |
|---|---|---|---|
| VV17 Lv-DD00024/30 | 17363 | | Anti-HLA-A2/HPV16E7$_{11-19}$ scFv 17363 in VL-VH orientation with huCD8 hinge/transmembrane domain, a 4-1BB co-stimulatory domain, and a CD3z signaling domain (Control CAR) |
| VV84 LvDD0037 | 28105P | | anti-HLA-A2/NY-ESO-1$_{157-165}$ scFv 28105P in VH-VL orientation with huCD8 hinge/transmembrane domain, a 4-1BB co-stimulatory domain, and a CD3z signaling domain (NY-ESO-1$_{157-165}$ BB/z CAR) |
| VV85 Lv-DD0038 | 28105P | | anti-HLA-A2/NY-ESO-1$_{157-165}$ scFv 28105P in VH-VL orientation with huCD28 hinge/transmembrane/costimulatory domains and a CD3z signaling domain (NY-ESO-1$_{157-165}$ 28/z CAR) |

Experimental Procedure

Generation of CAR Constructs and CAR T Cells

Chimeric antigen receptors containing either an anti-HLA-A2/NY-ESO-1$_{157-165}$ SCFV in the $V_H$-$V_L$ orientation plus either 1) a huCD8 hinge/transmembrane domain, a 4-1BB co-stimulatory domain, and a CD3z signaling domain (BB/z CAR), or 2) huCD28 hinge/transmembrane/costimulatory domains and a CD3z signaling domain (28/z CAR) were constructed using the $V_L$ and $V_H$ sequences of an anti-HLA-A2/NY-ESO-1$_{157-165}$ antibody, 28105P. As a non-binding control, a BB/z CAR was designed using an irrelevant scFv plus a huCD8 hinge/transmembrane domain, a 4-1BB co-stimulatory domain, and a CD3z signaling domain. These CARs were cloned into a pLVX lentiviral vector with an EF1a promoter and P2A:eGFP sequence (for tracking CAR-transduced cells), and VSV-pseudotyped lentivirus was produced.

CD3+ T cells were isolated from human peripheral blood mononuclear cells (PBMCs) from a normal donor, stimulated with CD3/CD28 microbeads plus 100 U/ml recombinant human IL-2, and transduced with the lentivirus at an MOI=5. The transduced cells were expanded for 19 days with CD3/CD28 microbeads plus 100 U/ml recombinant human IL-2 before being cryopreserved until use during the in vivo experiment.

Implantation and Measurement of Xenogenic Tumors

To determine the in vivo efficacy of anti-HLA-A2/NY-ESO-1$_{157-165}$-targeted chimeric antigen receptor (CAR) T cells, a xenogenic tumor study was performed. On day 0, immunodeficient NOD.Cg-Prkdc$^{scid}$Il2rg$^{tm1Wjl}$/SzJ (NSG) mice were subcutaneously injected with 5×10$^6$ HLA-A2$^+$ NY-ESO-1$^+$ A375 human melanoma tumor cells. On day 3 after tumors were established, the mice (n=5 per group) were intravenously injected with 20×10$^6$ T cells that express either the non-binding control BB/z CAR (Control CAR T), the anti-HLA-A2/NY-ESO-1$_{157-165}$ BB/z CAR, or the anti-HLA-A2/NY-ESO-1$_{157-165}$ 28/z CAR (as determined by the frequency of cells expressing GFP, which is a marker for those cells that have been transduced with CAR) from two different donors. Tumor growth was assessed through day 38 by measuring tumor volumes.

Calculation of Xenogenic Tumor Growth and Inhibition

In order to determine tumor volume by external caliper, the greatest longitudinal diameter (length in mm) and the greatest transverse diameter (width in mm) were determined. Tumor volumes based on caliper measurements were calculated by the formula: Volume (mm$^3$)=(length×width$^2$)/2.

Results Summary and Conclusions

A375 tumors grew progressively in mice receiving Control CAR T cells. Mice receiving anti-HLA-A2/NY-ESO-1$_{157-165}$ BB/z CAR T cells demonstrated some tumor control, with reduced tumor growth compared to Control CAR T-treated mice on days 21 ($p<0.04$), 28 ($p<0.0001$), and 38 ($p<0.0001$) (statistics analyzed by 2-way ANOVA). Anti-HLA-A2/NY-ESO-1$_{157-165}$ 28/z CAR T treatment also led to suppression of established A375 tumor growth on days 16 ($p=0.03$), 19 ($p=0.0002$), 21 ($p<0.0001$), 28 ($p<0.0001$), and 38 ($p<0.0001$) (statistics analyzed by 2-way ANOVA). Enhanced efficacy of anti-HLA-A2/NY-ESO-1$_{157-165}$ 28/z CAR vs. anti-HLA-A2/NY-ESO-1$_{157-165}$ BB/z CAR is confirmed, as tumor sizes on days 21 ($p=0.002$), 28 ($p<0.0001$), and 38 ($p<0.0001$) are statistically significant, ($p<0.0001$ on both days) by 2-way ANOVA. See FIGS. 6B-6E.

TABLE 19

| | Data Summary: | | |
|---|---|---|---|
| CAR T Treatment | Average Tumor Size (mm$^3$) on Day 3 | Tumor size standard error of the mean (SEM) | Number of mice still alive (of 5) on day 3 |
| Control CAR T | 57.2 | 7.1 | 5 |
| NY-ESO-1$_{157-165}$ BB/z CAR T | 69.1 | 11.4 | 5 |
| NY-ESO-1$_{157-165}$ 28/z CAR T | 79.4 | 4.0 | 5 |

TABLE 19-continued

Data Summary:

| CAR T Treatment | Average Tumor Size (mm$^3$) on Day 5 | Tumor size standard error of the mean (SEM) | Number of mice still alive (of 5) on day 5 |
|---|---|---|---|
| Control CAR T | 78.8 | 7.0 | 5 |
| NY-ESO-1$_{157-165}$ BB/z CAR T | 65.9 | 10.9 | 5 |
| NY-ESO-1$_{157-165}$ 28/z CAR T | 80.7 | 8.0 | 5 |

| CAR T Treatment | Average Tumor Size (mm$^3$) on Day 7 | Tumor size standard error of the mean (SEM) | Number of mice still alive (of 5) on day 7 |
|---|---|---|---|
| Control CAR T | 118.4 | 12.2 | 5 |
| NY-ESO-1$_{157-165}$ BB/z CAR T | 69.8 | 8.4 | 5 |
| NY-ESO-1$_{157-165}$ 28/z CAR T | 77.6 | 7.1 | 5 |

| CAR T Treatment | Average Tumor Size (mm$^3$) on Day 10 | Tumor size standard error of the mean (SEM) | Number of mice still alive (of 5) on day 10 |
|---|---|---|---|
| Control CAR T | 134.0 | 12.1 | 5 |
| NY-ESO-1$_{157-165}$ BB/z CAR T | 81.8 | 10.4 | 5 |
| NY-ESO-1$_{157-165}$ 28/z CAR T | 43.7 | 2.5 | 5 |

| CAR T Treatment | Average Tumor Size (mm$^3$) on Day 12 | Tumor size standard error of the mean (SEM) | Number of mice still alive (of 5) on day 12 |
|---|---|---|---|
| Control CAR T | 224.6 | 23.7 | 5 |
| NY-ESO-1$_{157-165}$ BB/z CAR T | 92.1 | 12.0 | 5 |
| NY-ESO-1$_{157-165}$ 28/z CAR T | 43.8 | 8.1 | 5 |

| CAR T Treatment | Average Tumor Size (mm$^3$) on Day 14 | Tumor size standard error of the mean (SEM) | Number of mice still alive (of 5) on day 14 |
|---|---|---|---|
| Control CAR T | 281.8 | 31.8 | 5 |
| NY-ESO-1$_{157-165}$ BB/z CAR T | 98.3 | 16.4 | 5 |
| NY-ESO-1$_{157-165}$ 28/z CAR T | 56.6 | 5.6 | 5 |

| CAR T Treatment | Average Tumor Size (mm$^3$) on Day 16 | Tumor size standard error of the mean (SEM) | Number of mice still alive (of 5) on day 16 |
|---|---|---|---|
| Control CAR T | 409.8 | 44.5 | 5 |
| NY-ESO-1$_{157-165}$ BB/z CAR T | 157.9 | 16.7 | 5 |
| NY-ESO-1$_{157-165}$ 28/z CAR T | 70.5 | 6.0 | 5 |

| CAR T Treatment | Average Tumor Size (mm$^3$) on Day 19 | Tumor size standard error of the mean (SEM) | Number of mice still alive (of 5) on day 19 |
|---|---|---|---|
| Control CAR T | 657.3 | 81.3 | 5 |
| NY-ESO-1$_{157-165}$ BB/z CAR T | 359.8 | 41.9 | 5 |
| NY-ESO-1$_{157-165}$ 28/z CAR T | 106.6 | 14.5 | 5 |

TABLE 19-continued

Data Summary:

| CAR T Treatment | Average Tumor Size (mm³) on Day 21 | Tumor size standard error of the mean (SEM) | Number of mice still alive (of 5) on day 21 |
| --- | --- | --- | --- |
| Control CAR T | 943.1 | 110.5 | 5 |
| NY-ESO-1$_{157\text{-}165}$ BB/z CAR T | 607.6 | 57.8 | 5 |
| NY-ESO-1$_{157\text{-}165}$ 28/z CAR T | 142.7 | 12.6 | 5 |

| CAR T Treatment | Average Tumor Size (mm³) on Day 28 | Tumor size standard error of the mean (SEM) | Number of mice still alive (of 5) on day 28 |
| --- | --- | --- | --- |
| Control CAR T | 2168.4 | 162.9 | 5 |
| NY-ESO-1$_{157\text{-}165}$ BB/z CAR T | 1351.5 | 154.6 | 5 |
| NY-ESO-1$_{157\text{-}165}$ 28/z CAR T | 523.8 | 57.7 | 5 |

| CAR T Treatment | Average Tumor Size (mm³) on Day 38 | Tumor size standard error of the mean (SEM) | Number of mice still alive (of 5) on day 38 |
| --- | --- | --- | --- |
| Control CAR T | 3904.3 | 157.4 | 5 |
| NY-ESO-1$_{157\text{-}165}$ BB/z CAR T | 2754.3 | 443.7 | 5 |
| NY-ESO-1$_{157\text{-}165}$ 28/z CAR T | 1696.4 | 144.0 | 5 |

Figure 11:
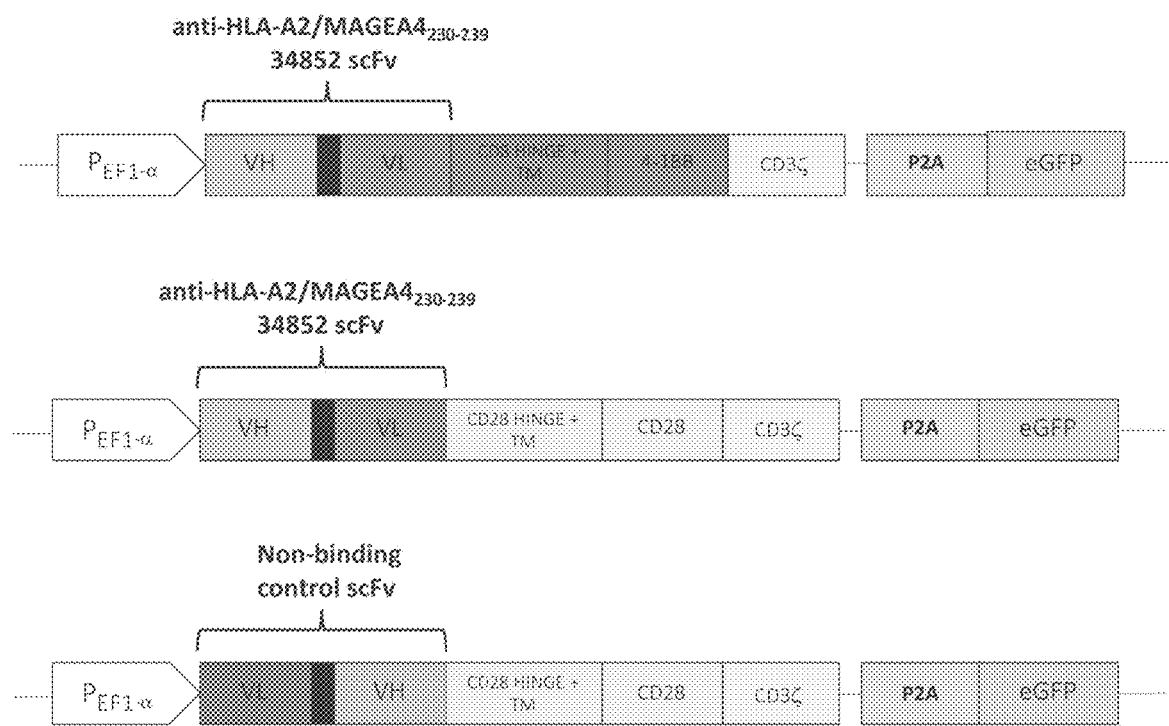
FIG. 11 demonstrates that anti-HLA-A2/MAGEA4$_{230-239}$ 28/z CAR T cells show superior in vivo anti-tumor activity and anti-tumor kinetics compared to anti-HLA-A2/MAGEA4$_{230-239}$ BB/z CAR T cells. Experimental parameters are discussed in Example 8.

Example 6: In Vitro Cytotoxicity by T Cells Expressing Chimeric Antigen Receptors Containing One of Two Anti-HLA-A2/MAGEA4$_{230\text{-}239}$ scFv's or an Anti-HLA-A2/MAGEA4$_{286\text{-}294}$ Chimeric antigen receptors containing one of two anti-HLA-A2/MAGEA4$_{230\text{-}239}$ scFv's or an anti-HLA-A2/MAGEA4$_{286\text{-}294}$ scFv plus either 1) a huCD8 hinge/transmembrane domain, a 4-1BB co-stimulatory domain, and a CD3z signaling domain (BB/z CAR), or 2) huCD28 hinge/transmembrane/costimulatory domains and a CD3z signaling domain (28/z CAR) were constructed using the $V_L$ and $V_H$ sequences of two anti-HLA-A2/MAGEA4$_{230\text{-}239}$ antibodies (33229 or 34852), and an anti-HLA-A2/MAGEA4$_{286\text{-}294}$ antibody (31345). As non-binding controls, a BB/z CAR was designed using an irrelevant scFv plus a huCD8 hinge/transmembrane domain, a 4-1BB co-stimulatory domain, and a CD3z signaling domain, and a 28/z CAR was designed using an irrelevant scFv plus huCD28 hinge/transmembrane/costimulatory domains and a CD3z signaling domain. These CARs were cloned into a pLVX lentiviral vector with an EF1a promoter and P2A:eGFP sequence (for tracking CAR-transduced cells), and VSV-pseudotyped lentivirus was produced. See FIG. 8 and FIG. 11 for construct design and FIGS. 7A-7E for results.

TABLE 20

CAR scFv IDs:

| AbPID | AbPID | Specificity | Description |
| --- | --- | --- | --- |
| 8808 | 8808 | Non-binding control | Anti-MUC16 scFv 8808 in VL-VH orientation with huCD8 hinge/transmembrane domain, a 4-1BB co-stimulatory domain, and a CD3z signaling domain (BB/z Control CAR) used in panels A-F |
| 8808 | 8808 | Non-binding control | Anti-MUC16 scFv 8808 in VL-VH orientation with huCD28 hinge/transmembrane/costimulatory domains and a CD3z signaling domain (28/z Control CAR) used in panels A-F |
| 3B9 | 3B9 | Non-binding control | Anti-CD20 scFv 3B9 in VL-VH orientation with huCD28 hinge/transmembrane/costimulatory domains and a CD3z signaling domain (28/z Control CAR) used in panels G-H |
| 33229 | 33229 | HLA-A2/ MAGEA4$_{230\text{-}239}$ | anti- HLA-A2/MAGEA4$_{230\text{-}239}$ scFv 33229 in VL-VH-VL orientation with huCD8 hinge/transmembrane domain, a 4-1BB co-stimulatory domain, and a CD3z signaling domain (HLA-A2/MAGEA4$_{230\text{-}239}$ CAR 33229 BB/z) |

TABLE 20-continued

CAR scFv IDs:

| AbPID | AbPID | Specificity | Description |
|---|---|---|---|
| 33229 | 33229 | HLA-A2/ MAGEA4$_{230-239}$ | anti-HLA-A2/MAGEA4$_{230-239}$ scFv 33229 in VL-VH orientation with huCD28 hinge/transmembrane/costimulatory domains and a CD3z signaling domain (HLA-A2/ MAGEA4$_{230-239}$ CAR 33229 28/z) |
| 34852 | 34852 | HLA-A2/ MAGEA4230-239 | anti-HLA-A2/MAGEA4230-239 34852 in VH-VL orientation with huCD8 hinge/transmembrane domain, a 4-1BB co-stimulatory domain, and a CD3z signaling domain (HLA-A2/MAGEA4230-239 CAR 34852 BB/z) |
| 34852 | 34852 | HLA-A2/ MAGEA4230-239 | anti-HLA-A2/MAGEA4230-239 34852 in VH-VL orientation with huCD28 hinge/transmembrane/costimulatory domains and a CD3z signaling domain (HLA-A2/ MAGEA4230-239 CAR 34852 28/z) |
| 31345 | 31345 | HLA-A2/ MAGEA4286-294 | anti-HLA-A2/MAGEA4286-294 scFv 31345 in VL-VH orientation with huCD8 hinge/transmembrane domain, a 4-1BB co-stimulatory domain, and a CD3z signaling domain (HLA-A2/MAGEA4286-294 CAR 31345 BB/z) |
| 31345 | 31345 | HLA-A2/ MAGEA4286-294 | anti- HLA-A2/MAGEA4286-294 scFv 31345 in VL-VH orientation with huCD28 hinge/transmembrane/costimulatory domains and a CD3z signaling domain (HLA-A2/ MAGEA4286-294 CAR 31345 28/z) |

Experimental Procedure

Generation of CAR Constructs and CAR T Cells

Chimeric antigen receptors containing one of two anti-HLA-A2/MAGEA4$_{230-239}$ scFv's or an anti-HLA-A2/MAGEA4$_{286-294}$ scFv plus either 1) a huCD8 hinge/transmembrane domain, a 4-1BB co-stimulatory domain, and a CD3z signaling domain (BB/z CAR), or 2) huCD28 hinge/transmembrane/costimulatory domains and a CD3z signaling domain (28/z CAR) were constructed using the $V_L$ and $V_H$ sequences of two anti-HLA-A2/MAGEA4$_{230-239}$ antibodies (33229 or 34852) and an anti-HLA-A2/MAGEA4$_{286-294}$ antibody (31345). As non-binding controls, a BB/z CAR was designed using an irrelevant scFv plus a huCD8 hinge/transmembrane domain, a 4-1BB co-stimulatory domain, and a CD3z signaling domain, and a 28/z CAR was designed using an irrelevant scFv plus huCD28 hinge/transmembrane/costimulatory domains and a CD3z signaling domain. These CARs were cloned into a pLVX lentiviral vector with an EF1a promoter and P2A:eGFP sequence (for tracking CAR-transduced cells), and VSV-pseudotyped lentivirus was produced.

CD3+ T cells were isolated from human peripheral blood mononuclear cells (PBMCs) from a normal donor, stimulated with CD3/CD28 microbeads plus 100 U/ml recombinant human IL-2, and transduced with the lentivirus at an MOI=5. The transduced cells were expanded for 14 days with CD3/CD28 microbeads plus 100 U/ml recombinant human IL-2 before use in the in vitro cytotoxicity assay.

Calcein-Release Cytotoxicity Assay

To determine the in vitro cytotoxic activity of anti-HLA-A2/MAGEA4$_{230-239}$- and anti-HLA-A2/MAGEA4$_{286-294}$-targeted chimeric antigen receptor (CAR) T cells with either BB/z or 28/z intracellular signaling domains, a 2.5-hour calcein release assay was performed. A375 or SK-MEL-37 cells (2× 10$^6$ cells/mL) were labeled with 8 μM Calcein-AM (ThermoFisher) for 35 minutes at 37° C. and washed 3 times with media. CAR-transduced activated/expanded T cells and calcein labeled target cells were co-cultured at various ratios in triplicate for 2.5 hrs in 96-well round-bottom plates at 37° C. After incubation, culture supernatant was transferred to a black clear bottom 96 well microplate (Greiner Bio One) and calcein fluorescence was measured using a microplate reader. Percent calcein release was calculated as ((Calcein signal-Spontaneous Calcein Release)/(Calcein Maximum Release-Spontaneous Calcein Release))*100 and reported as percent cytotoxicity. Spontaneous release was determined by target cells only, and maximal release was determined by lysing target cells with 1% Triton X-114 detergent.

Results Summary and Conclusions

Figure 7A:
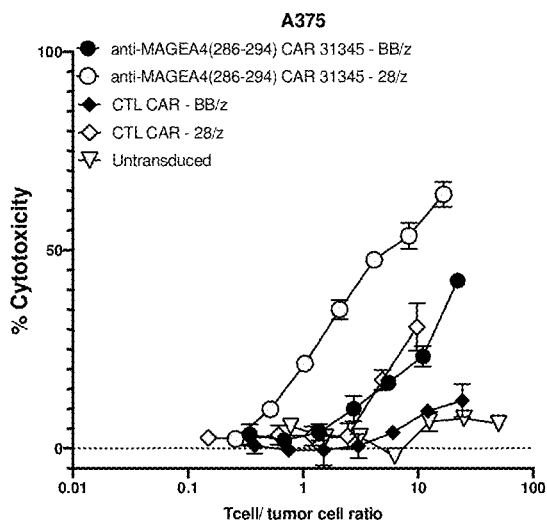
FIGS. 7A-7E show that MAGEA4$_{286-294}$ 28/z CAR T cells demonstrate superior in vitro cytotoxicity compared to MAGEA4$_{286-294}$ BB/z CAR T cells against various target cells. Modest cytotoxicity of the MAGEA4$^+$HLA-A2$^+$ A375 and SK-MEL-37 cells was seen by the anti-MAGEA4$_{286-294}$ CAR (31345) with a BB/z intracellular signaling domain; by contrast, augmented cytotoxicity was seen by the anti-MAGEA4$_{286-294}$ CAR (31345) with a 28/z intracellular signaling domain (FIGS. 7A and 7B). Modest cytotoxicity of the MAGEA4$^+$HLA-A2$^+$ A375 and SK-MEL-37 cells was seen by the anti-MAGEA4$_{230-239}$ CAR (33229) with a BB/z intracellular signaling domain; by contrast, augmented cytotoxicity was seen by the anti-MAGEA4$_{239-239}$ CAR (33229) with a 28/z intracellular signaling domain and minimal background cytotoxicity was induced by CTL CAR constructs (FIGS. 7C and 7D). Modest cytotoxicity of the MAGEA4$^+$HLA-A2$^+$ A375 cells was seen by the anti-MAGEA4$_{230-239}$ CAR (34852) with a BB/z intracellular signaling domain; by contrast, augmented cytotoxicity was seen by the anti-MAGEA4$_{239-239}$ CAR (34852) with a 28/z intracellular signaling domain (FIG. 7E).
Figure 7B:
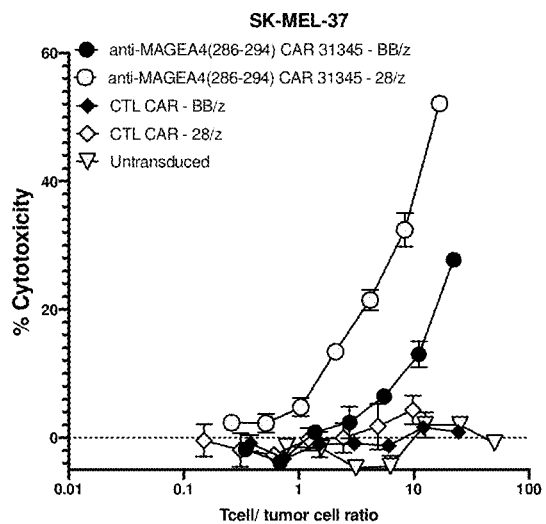
Figure 8:
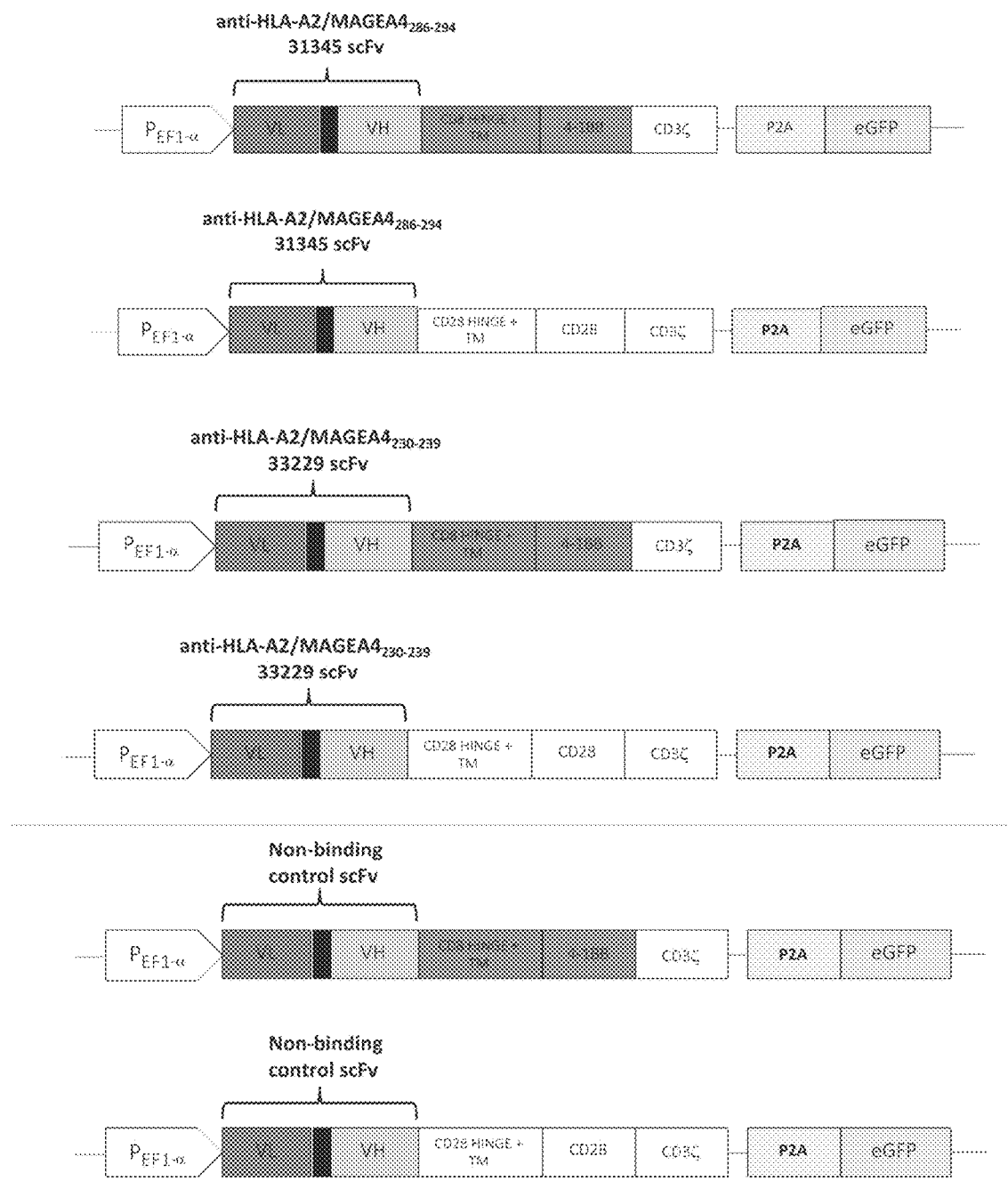
FIG. 8 shows illustrations of exemplary CAR constructs used in Example 6.
Figure 9A:
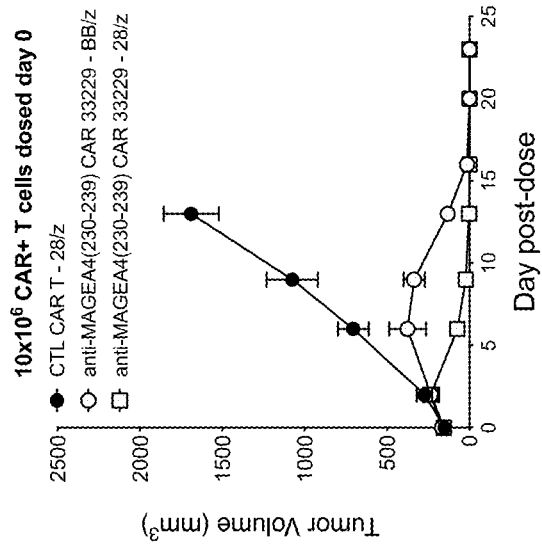
FIGS. 9A-9C show in vivo dose-response study experiment comparing the ability of MAGEA4(230-239) binder 33229 to clear A375 tumors when formatted as BB/z or 28/z CARs. As shown in previous non-dose-response studies, 28/z CAR T demonstrate superior in vivo anti-tumor activity and anti-tumor kinetics.
Figure 9B:
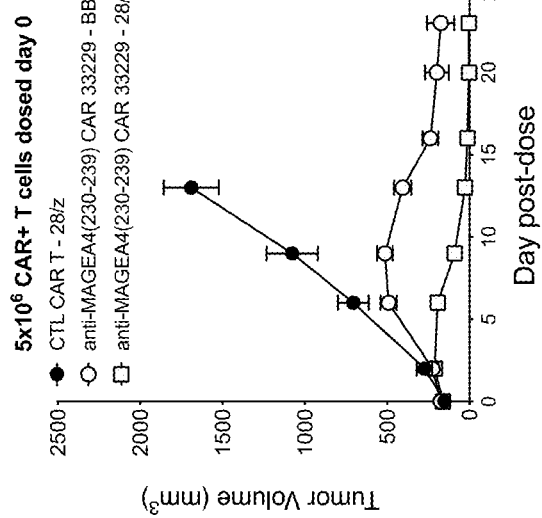
Figure 9C:
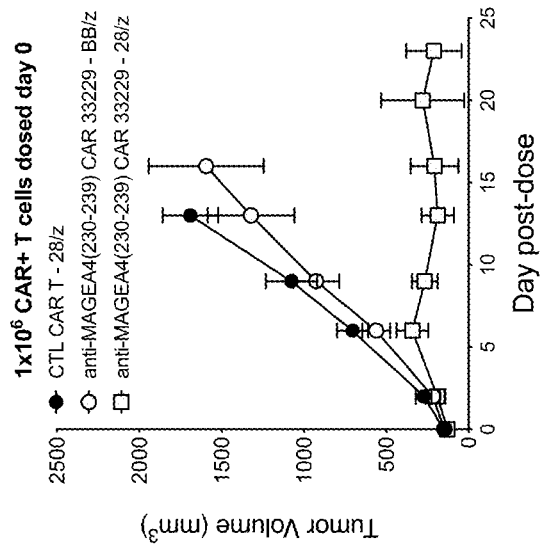
Figure 10:
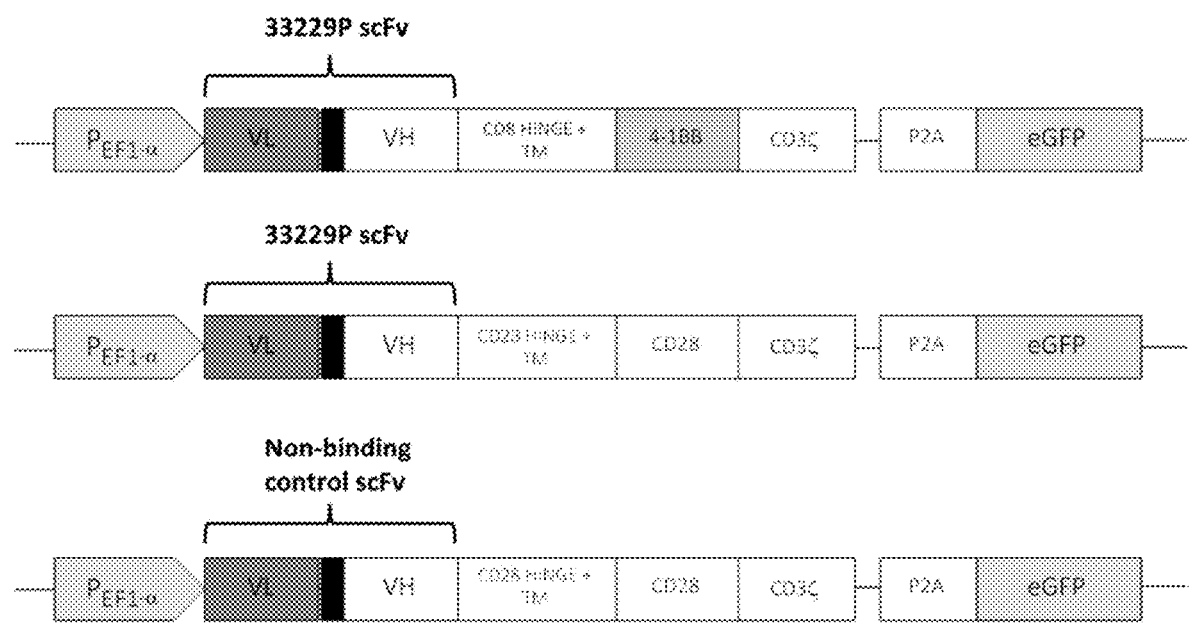
FIG. 10 shows illustrations of exemplary CAR constructs used in Example 7.

Modest cytotoxicity of the MAGEA4$^+$HLA-A2$^+$ A375 and SK-MEL-37 cells was seen by the anti-MAGEA4$_{286-294}$ CAR (31345) with a BB/z intracellular signaling domain; by contrast, augmented cytotoxicity was seen by the anti-MAGEA4$_{286-294}$ CAR (31345) with a 28/z intracellular signaling domain (FIGS. 7A-7B). Minimal background cytotoxicity was induced by CTL CAR constructs (FIGS. 7A-7B). Thus, the anti-MAGEA4$_{286-294}$ CAR (31345) CAR with a 28/z signaling domain induced superior cytotoxicity compared with the same CAR utilizing a BB/z signaling domain.

Figure 7C:
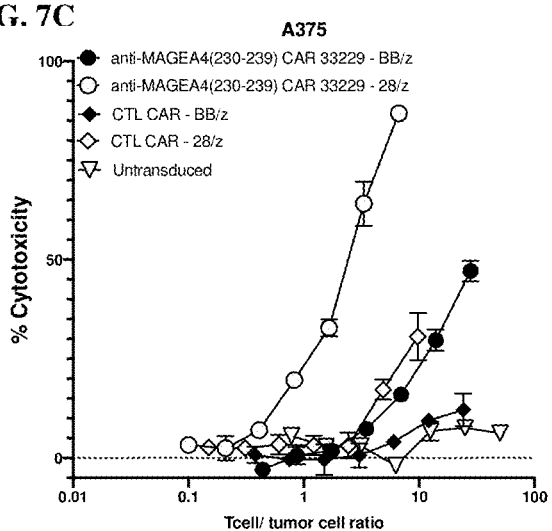
Figure 7D:
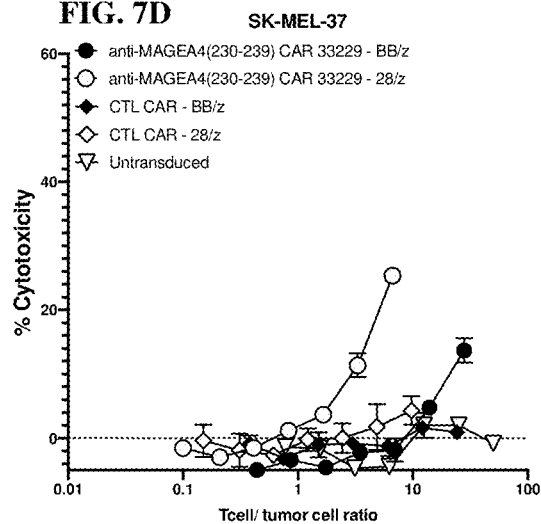

Modest cytotoxicity of the MAGEA4$^+$HLA-A2$^+$ A375 and SK-MEL-37 cells was seen by the anti-MAGEA4$_{230-239}$ CAR (33229) with a BB/z intracellular signaling domain; by contrast, augmented cytotoxicity was seen by the anti-MAGEA4$_{239-239}$ CAR (33229) with a 28/z intracellular signaling domain (FIGS. 7C-7D), and minimal background cytotoxicity was induced by CTL CAR constructs (FIGS. 7C-7D). Thus, the anti-MAGEA4$_{230-239}$ CAR (33229) CAR with a 28/z signaling domain induced superior cytotoxicity compared with the same CAR utilizing a BB/z signaling domain.

Figure 7E:
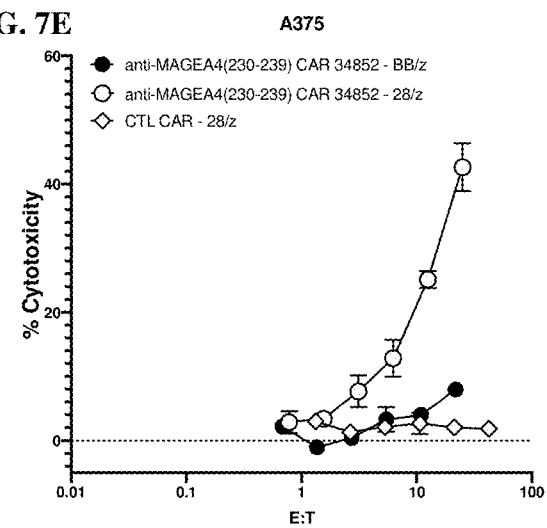

Modest cytotoxicity of the MAGEA4$^+$HLA-A2$^+$ A375 cells was seen by the anti-MAGEA4$_{230-239}$ CAR (34852)

with a BB/z intracellular signaling domain; by contrast, augmented cytotoxicity was seen by the anti-MAGEA4$_{239\text{-}239}$ CAR (34852) with a 28/z intracellular signaling domain (FIG. 7E). Minimal background cytotoxicity was induced by CTL CAR constructs (FIG. 7E). Thus, the anti-MAGEA4$_{230\text{-}239}$ CAR (34852) CAR with a 28/z signaling domain induced superior cytotoxicity compared with the same CAR utilizing a BB/z signaling domain.

TABLE 21

Tabulated Data Summary:

| CAR+ T cell:Tumor cell ratio | Mean % Cytotoxicity | SEM % Cytotoxicity |
|---|---|---|
| \multicolumn{3}{c}{A375 Cytotoxicity} | | |
| \multicolumn{3}{c}{anti-MAGEA4(286-294) CAR 31345 - BB/z} | | |
| 0.34361233 | 3.495440717 | 2.621060458 |
| 0.68722467 | 2.077001 | 1.186968046 |
| 1.37665198 | 4.103343463 | 2.073290977 |
| 2.75330396 | 10.03039513 | 3.189478464 |
| 5.50660793 | 16.5653495 | 1.145152438 |
| 11.0132159 | 23.20162103 | 2.583586633 |
| 22.0264317 | 42.35055723 | 1.150741309 |
| anti-MAGEA4(286-294) CAR 31345 - 28/z | | |
| 0.26 | 2.407704657 | 1.08602371 |
| 0.52 | 9.898341357 | 1.371429173 |
| 1.04 | 21.40181917 | 1.913488987 |
| 2.08 | 35.04547887 | 2.43842243 |
| 4.16 | 47.56554307 | 1.689422527 |
| 8.32 | 53.611557 | 3.258510426 |
| 16.65 | 64.0449438 | 3.152684838 |
| anti-MAGEA4(230-239) CAR 33229 - BB/z | | |
| 0.44 | −2.940311667 | 1.020250017 |
| 0.87 | 0.588062337 | 2.199541805 |
| 1.75 | 1.822993237 | 0.459291368 |
| 3.49 | 7.350779187 | 0.058806233 |
| 6.98 | 15.99529547 | 1.617973121 |
| 13.97 | 29.69714793 | 2.627263494 |
| 27.93 | 47.16259923 | 2.619354002 |
| anti-MAGEA4(230-239) CAR 33229 - 28/z | | |
| 0.1 | 3.267093297 | 1.391982373 |
| 0.21 | 2.458740327 | 3.043275709 |
| 0.41 | 6.972044467 | 1.549343217 |
| 0.83 | 19.63624117 | 1.659640955 |
| 1.66 | 32.83933983 | 2.168201695 |
| 3.32 | 64.0956551 | 5.554466059 |
| 6.65 | 86.8642641 | 1.8187942 |
| CTL CAR - BB/z | | |
| 0.38 | 0.754840817 | 2.047453102 |
| 0.75 | −0.426649173 | 1.430554304 |
| 1.51 | −0.42664915 | 3.847548632 |
| 3.02 | 0.623564147 | 3.012935339 |
| 6.05 | 4.036757463 | 1.197787175 |
| 12.1 | 9.419100757 | 0.328191663 |
| 24.2 | 12.11027239 | 4.125827394 |
| CTL CAR - 28/z | | |
| 0.15 | 2.63578275 | 1.615315369 |
| 0.31 | 2.476038337 | 0.76193227 |
| 0.61 | 3.35463259 | 2.47603834 |
| 1.22 | 3.115015967 | 2.429218272 |
| 2.44 | 3.11501597 | 3.203861205 |
| 4.88 | 17.25239617 | 2.514389178 |
| 9.77 | 30.5910543 | 5.9904153 |
| Untransduced | | |
| 0.78 | 5.599313063 | 1.428185853 |
| 1.56 | 2.844442065 | 1.866547656 |
| 3.125 | 3.016582507 | 1.041244538 |
| 6.25 | −1.919486757 | 1.386474998 |
| 12.5 | 6.7716742 | 2.405323802 |
| 25 | 7.53120193 | 1.474651073 |
| 50 | 6.269535185 | 1.783611187 |

TABLE 21-continued

| Tabulated Data Summary: | | |
|---|---|---|
| CAR+ T cell:Tumor cell ratio | Mean % Cytotoxicity | SEM % Cytotoxicity |
| anti-MAGEA4(230-239) CAR- scFv X - BB/z | | |
| 0.6828125 | 2.17524042 | 1.08412645 |
| 1.365625 | −1.030377047 | 0.992567116 |
| 2.73125 | 0.40451838 | 0.820902448 |
| 5.4625 | 3.304838947 | 1.953900173 |
| 10.925 | 4.007021827 | 0.61968503 |
| 21.85 | 7.97588155 | 1.117153078 |
| anti-MAGEA4(230-239) CAR- scFv X - 28/z | | |
| 0.78125 | 2.877423307 | 1.702013098 |
| 1.5625 | 3.426957713 | 1.021262627 |
| 3.125 | 7.67058466 | 2.474788746 |
| 6.25 | 12.83010229 | 2.871738919 |
| 12.5 | 25.1030377 | 1.344346732 |
| 25 | 42.6270798 | 3.696614762 |
| CTL CAR - 28/z | | |
| 1.328125 | 3.011329757 | 0.823567521 |
| 2.65625 | 1.311866427 | 1.104368467 |
| 5.3125 | 2.116875373 | 0.823567522 |
| 10.625 | 2.683363157 | 1.64308237 |
| 21.25 | 2.05724508 | 1.213663237 |
| 42.5 | 1.84853906 | 1.058752588 |
| SK-MEL-37 Cytotoxicity | | |
| anti-MAGEA4(286-294) CAR 31345 - BB/z | | |
| 0.34361233 | −1.834261367 | 0.654273987 |
| 0.68722467 | −3.799541433 | 0.947623724 |
| 1.37665198 | 0.851621356 | 0.472394533 |
| 2.75330396 | 2.39109072 | 2.491724015 |
| 5.50660793 | 6.48542417 | 0.53920988 |
| 11.0132159 | 13.00360301 | 2.042378942 |
| 22.0264317 | 27.7432034 | 0.654273954 |
| anti-MAGEA4(286-294) CAR 31345 - 28/z | | |
| 0.26 | 2.338101827 | 0.244185631 |
| 0.52 | 2.245808323 | 1.448547295 |
| 1.04 | 4.768497154 | 1.42416699 |
| 2.08 | 13.41332103 | 0.857551751 |
| 4.16 | 21.47361947 | 1.595310522 |
| 8.32 | 32.42578065 | 2.599008367 |
| 16.65 | 52.11505923 | 0.378040479 |
| anti-MAGEA4(230-239) CAR 33229 - BB/z | | |
| 0.44 | −4.988222233 | 0.530892193 |
| 0.87 | −3.4363309 | 0.4156852 |
| 1.75 | −4.572537065 | 0.91618541 |
| 3.49 | −2.272412367 | 0.534496362 |
| 6.98 | −1.88443953 | 1.796179079 |
| 13.97 | 4.766523486 | 0.762467313 |
| 27.93 | 13.68989883 | 1.903698993 |
| anti-MAGEA4(230-239) CAR 33229 - 28/z | | |
| 0.1 | −1.572367567 | 0.292764964 |
| 0.21 | −2.990076067 | 0.717587881 |
| 0.41 | −1.546591056 | 0.87526366 |
| 0.83 | 1.13416677 | 0.491108619 |
| 1.66 | 3.660265497 | 0.558226776 |
| 3.32 | 11.36744428 | 1.838825301 |
| 6.65 | 25.36409333 | 1.120908121 |
| CTL CAR - BB/z | | |
| 0.38 | −0.878821637 | 1.275090509 |
| 0.75 | −3.230597833 | 0.483208867 |
| 1.51 | −1.05211041 | 1.974399741 |
| 3.02 | −0.878821633 | 0.202632828 |
| 6.05 | −1.2501547 | 0.546307122 |
| 12.1 | 1.57197673 | 0.433752085 |
| 24.2 | 0.903577163 | 1.045317121 |
| CTL CAR - 28/z | | |
| 0.15 | −0.44298047 | 2.513689458 |
| 0.31 | −1.919582027 | 2.632422705 |
| 0.61 | −2.691958201 | 0.315593912 |
| 1.22 | −0.261244887 | 1.753183224 |

TABLE 21-continued

Tabulated Data Summary:

| CAR+ T cell:Tumor cell ratio | Mean % Cytotoxicity | SEM % Cytotoxicity |
|---|---|---|
| 2.44 | −0.011358463 | 2.32546539 |
| 4.88 | 1.737846437 | 3.57826167 |
| 9.77 | 4.327578373 | 2.241162378 |
| Untransduced | | |
| 0.78 | −1.3856173 | 0.308591616 |
| 1.56 | −1.662740733 | 0.26435893 |
| 3.125 | −4.7110988 | 1.009505652 |
| 6.25 | −4.461687682 | 1.637844185 |
| 12.5 | 1.998034703 | 1.962821925 |
| 25 | 1.99803472 | 0.484724813 |
| 50 | −0.818866707 | 0.681580484 |

Example 7: Chimeric Antigen Receptors Containing One of Two Anti-HLA-A2/MAGEA4$_{230-239}$ scFv Chimeric antigen receptors containing either an anti-HLA-A2/MAGEA4$_{230-239}$ SCFV in the $V_L$-$V_H$ orientation plus either 1) a huCD8 hinge/transmembrane domain, a 4-1BB co-stimulatory domain, and a CD3z signaling domain (BB/z CAR), or 2) huCD28 hinge/transmembrane/costimulatory domains and a CD3z signaling domain (28/z CAR) were constructed using the $V_L$ and $V_H$ sequences of an anti-HLA-A2/MAGEA4$_{230-239}$ antibody, 33229P. As a non-binding control, a 28/z CAR was designed using an irrelevant scFv plus a huCD28 hinge/transmembrane/costimulatory domains and a CD3z signaling domain. These CARs were cloned into a pLVX lentiviral vector with an EF1a promoter and P2A:eGFP sequence (for tracking CAR-transduced cells), and VSV-pseudotyped lentivirus was produced. See FIGS. 9A-9C and FIG. 10 for design of results and construct, respectively.

Collectively, the results demonstrate that anti-HLA-A2/MAGEA4$_{230-239}$ 28/z CAR T cells demonstrate superior in vivo anti-tumor activity and anti-tumor kinetics compared to anti-HLA-A2/MAGEA4$_{230-239}$ BB/z CAR T cells.

CAR) were constructed using the $V_L$ and $V_H$ sequences of an anti-HLA-A2/MAGEA4$_{230-239}$ antibody, 33229P. As a non-binding control, a 28/z CAR was designed using an irrelevant scFv plus a huCD28 hinge/transmembrane/costimulatory domains and a CD3z signaling domain. These CARs were cloned into a pLVX lentiviral vector with an EF1a promoter and P2A:eGFP sequence (for tracking CAR-transduced cells), and VSV-pseudotyped lentivirus was produced.

CD3+ T cells were isolated from human peripheral blood mononuclear cells (PBMCs) from a normal donor, stimulated with CD3/CD28 microbeads plus 100 U/ml recombinant human IL-2, and transduced with the lentivirus at an MOI=5. The transduced cells were expanded for approximately 14 days with CD3/CD28 microbeads plus 100 U/ml recombinant human IL-2 before being cryopreserved until use during the in vivo experiment.

Implantation and Measurement of Xenogenic Tumors

To determine the in vivo efficacy of anti-HLA-A2/MAGEA4$_{230-239}$-targeted chimeric antigen receptor (CAR) T cells, a xenogenic tumor study was performed. On day 0, immunodeficient NOD.Cg-Prkdc$^{scid}$Il2rg$^{tm1Wjl}$/SzJ (NSG) mice were subcutaneously injected with $5 \times 10^6$ HLA-A2+

TABLE 22

CAR scFv IDs:

| AbPID | AbPID | Specificity | Description |
|---|---|---|---|
| 17363 | 17363N | Non-binding control | Anti-HLA-A2/HPV16E7$_{11-19}$ scFv 17363N in VL-VH orientation with huCD28 hinge/transmembrane/costimulatory domains and a CD3z signaling domain (Control CAR) |
| 33229P | 33229P | HLA-A2/MAGEA4$_{230-239}$ | anti-HLA-A2/MAGEA4$_{230-239}$ scFv 33229P in VL-VH orientation with huCD8 hinge/transmembrane domain, a 4-1BB co-stimulatory domain, and a CD3z signaling domain (MAGEA4$_{230-239}$ BB/z CAR) |
| 33229P | 33229P | HLA-A2/MAGEA4$_{230-239}$ | anti-HLA-A2/MAGEA4$_{230-239}$ scFv 33229P in VL-VH orientation with huCD28 hinge/transmembrane/costimulatory domains and a CD3z signaling domain (MAGEA4$_{230-239}$ 28/z CAR) |

Experimental Procedure
Generation of CAR Constructs and CAR T Cells

Chimeric antigen receptors containing either an anti-HLA-A2/MAGEA4$_{230-239}$ SCFV in the $V_L$-$V_H$ orientation plus either 1) a huCD8 hinge/transmembrane domain, a 4-1BB co-stimulatory domain, and a CD3z signaling domain (BB/z CAR), or 2) huCD28 hinge/transmembrane/costimulatory domains and a CD3z signaling domain (28/z CAR) were constructed using the $V_L$ and $V_H$ sequences of an anti-HLA-A2/MAGEA4$_{230-239}$ antibody, 33229P. As a non-binding control, a 28/z CAR was designed using an irrelevant scFv plus a huCD28 hinge/transmembrane/costimulatory domains and a CD3z signaling domain. These CARs were cloned into a pLVX lentiviral vector with an EF1a promoter and P2A:eGFP sequence (for tracking CAR-transduced cells), and VSV-pseudotyped lentivirus was produced.

CD3+ T cells were isolated from human peripheral blood mononuclear cells (PBMCs) from a normal donor, stimulated with CD3/CD28 microbeads plus 100 U/ml recombinant human IL-2, and transduced with the lentivirus at an MOI=5. The transduced cells were expanded for approximately 14 days with CD3/CD28 microbeads plus 100 U/ml recombinant human IL-2 before being cryopreserved until use during the in vivo experiment.

MAGEA4+A375 human melanoma tumor cells. Using mass spectrometry techniques, it was determined that A375 melanoma cells express approximately 553 cell-surface copies of the HLA-A2/MAGEA4$_{230-239}$ peptide. On day 11 after tumors were established, the mice (n≥5 per group) were intravenously injected with either $1 \times 10^6$, $5 \times 10^6$, or $10 \times 10^6$ T cells that express either the non-binding control 28/z CAR (Control CAR T), the anti-HLA-A2/MAGEA4$_{230-239}$ BB/z CAR, or the anti-HLA-A2/MAGEA4$_{230\text{-}239}$ 28/z CAR (as determined by the frequency of cells expressing either GFP, which is a marker for those cells that have been transduced with CAR). Tumor growth was assessed through day 28 by measuring tumor volumes.

Calculation of Xenogenic Tumor Growth and Inhibition

In order to determine tumor volume by external caliper, the greatest longitudinal diameter (length in mm) and the greatest transverse diameter (width in mm) were determined. Tumor volumes based on caliper measurements were calculated by the formula: Volume (mm$^3$)=(length×width$^2$)/2.

Results Summary

1×10$^6$ dose of CAR T: A375 tumors grew progressively in mice receiving control CAR T cells. Mice receiving anti-HLA-A2/MAGEA4$_{230\text{-}239}$ BB/z CAR T cells did not demonstrate tumor control. By contrast, anti-HLA-A2/MAGEA4$_{230\text{-}239}$ 28/z CAR T treatment led to suppression of established A375 tumor growth compared to Control CAR T on days 9 (p=0.001), 13 (p<0.0001), and 16 (p<0.0001) (statistics analyzed by 2-way ANOVA). Enhanced efficacy of anti-HLA-A2/MAGEA4$_{230\text{-}239}$ 28/z CAR vs. anti-HLA-A2/MAGEA4$_{230\text{-}239}$ BB/z CAR is confirmed, as tumor sizes on days 9 (p=0.0086), 13 (p<0.0001) and 16 (p<0.0001) are statistically significant by 2-way ANOVA.

5×10$^6$ dose of CAR T: A375 tumors grew progressively in mice receiving control CAR T cells. Anti-HLA-A2/MAGEA4$_{230\text{-}239}$ BB/z CAR T cell treatment led to suppression of established A375 tumor growth compared to Control CAR T on days 9 (p<0.0001), 13 (p<0.0001), and 16 (p<0.0001) (statistics analyzed by 2-way ANOVA). Anti-HLA-A2/MAGEA4$_{230\text{-}239}$ 28/z CAR T treatment also led to suppression of established A375 tumor growth on days 6 (p<0.0001), days 9 (p<0.0001), 13 (p<0.0001), and 16 (p<0.0001) (statistics analyzed by 2-way ANOVA). Enhanced efficacy of anti-HLA-A2/MAGEA4$_{230\text{-}239}$ 28/z CAR vs. anti-HLA-A2/MAGEA4$_{230\text{-}239}$ BB/z CAR is confirmed, as tumor sizes on days 6 (p=0.0049), 9 (p<0.0001), 13 (p=0.0003) and 16 (p=0.0453) are statistically significant by 2-way ANOVA.

10×10$^6$ dose of CAR T: A375 tumors grew progressively in mice receiving control CAR T cells. Anti-HLA-A2/MAGEA4$_{230\text{-}239}$ BB/z CAR T cell treatment led to suppression of established A375 tumor growth compared to Control CAR T on days 6 (p=0.0214), 9 (p<0.0001), 13 (p<0.0001), and 16 (p<0.0001) (statistics analyzed by 2-way ANOVA). Anti-HLA-A2/MAGEA4$_{230\text{-}239}$ 28/z CAR T treatment also led to suppression of established A375 tumor growth on days 6 (p<0.0001), days 9 (p<0.0001), 13 (p<0.0001), and 16 (p<0.0001) (statistics analyzed by 2-way ANOVA). Enhanced efficacy of anti-HLA-A2/MAGEA4$_{230\text{-}239}$ 28/z CAR vs. anti-HLA-A2/MAGEA4$_{230\text{-}239}$ BB/z CAR is confirmed, as tumor sizes on days 6 (p=0.0282) and 9 (p=0.0212) are statistically significant by 2-way ANOVA.

TABLE 23

Tabulated Data Summary:

| Days after dosing CAR T | Mean tumor volume (mm3) | Tumor volume standard error of the mean (SEM) | Number of mice alive |
|---|---|---|---|
| Control CAR T 28/z | | | |
| 0 | 152.93 | 28.39 | 5 |
| 2 | 273.33 | 47.33 | 5 |
| 6 | 706.24 | 94.17 | 5 |
| 9 | 1076.98 | 155.83 | 5 |
| 13 | 1690.17 | 167.36 | 5 |
| 16 | 2438.08 | 270.27 | 4 |
| 20 | | | 0 |
| 23 | | | 0 |
| anti-MAGEA4(230-239) CAR T BB/z 1e6 dose | | | |
| 0 | 147.95 | 23.54 | 5 |
| 2 | 217.85 | 45.47 | 5 |
| 6 | 562.00 | 83.95 | 5 |
| 9 | 926.51 | 140.92 | 5 |
| 13 | 1322.27 | 263.85 | 5 |
| 16 | 1594.67 | 350.63 | 5 |
| 20 | 1902.97 | 209.18 | 4 |
| 23 | 1988.75 | 408.62 | 2 |
| anti-MAGEA4(230-239) CAR T BB/z 5e6 dose | | | |
| 0 | 175.91 | 15.38 | 8 |
| 2 | 225.22 | 33.12 | 8 |
| 6 | 492.59 | 49.56 | 8 |
| 9 | 513.64 | 47.10 | 8 |
| 13 | 406.94 | 52.15 | 8 |
| 16 | 238.39 | 48.51 | 8 |
| 20 | 198.05 | 71.77 | 8 |
| 23 | 175.28 | 84.08 | 8 |
| anti-MAGEA4(230-239) CAR T BB/z 10e6 dose | | | |
| 0 | 167.56 | 16.84 | 7 |
| 2 | 235.62 | 42.37 | 7 |
| 6 | 376.09 | 112.15 | 7 |
| 9 | 337.07 | 64.66 | 7 |
| 13 | 132.88 | 29.92 | 7 |
| 16 | 14.81 | 12.74 | 7 |
| 20 | 0.00 | 0.00 | 7 |
| 23 | 0.00 | 0.00 | 7 |
| anti-MAGEA4(230-239) CAR T 28/z 1e6 dose | | | |
| 0 | 129.31 | 25.19 | 5 |
| 2 | 190.09 | 48.25 | 5 |
| 6 | 342.10 | 95.56 | 5 |
| 9 | 267.18 | 78.18 | 5 |
| 13 | 187.90 | 98.59 | 5 |
| 16 | 208.26 | 145.32 | 5 |
| 20 | 280.10 | 252.66 | 5 |
| 23 | 212.50 | 168.19 | 5 |
| anti-MAGEA4(230-239) CAR T 28/z 5e6 dose | | | |
| 0 | 161.61 | 14.84 | 8 |
| 2 | 210.63 | 21.97 | 8 |
| 6 | 193.05 | 32.71 | 8 |
| 9 | 90.31 | 35.41 | 8 |
| 13 | 27.67 | 18.02 | 8 |
| 16 | 13.17 | 13.17 | 8 |
| 20 | 3.33 | 3.33 | 8 |
| 23 | 6.06 | 6.06 | 8 |
| anti-MAGEA4(230-239) CAR T 28/z 10e6 dose | | | |
| 0 | 155.47 | 21.18 | 6 |
| 2 | 235.05 | 49.94 | 6 |
| 6 | 74.45 | 24.65 | 6 |
| 9 | 23.02 | 9.07 | 6 |
| 13 | 3.41 | 3.41 | 6 |
| 16 | 0.00 | 0.00 | 6 |
| 20 | 0.00 | 0.00 | 6 |
| 23 | 0.00 | 0.00 | 6 |

Figure 12:
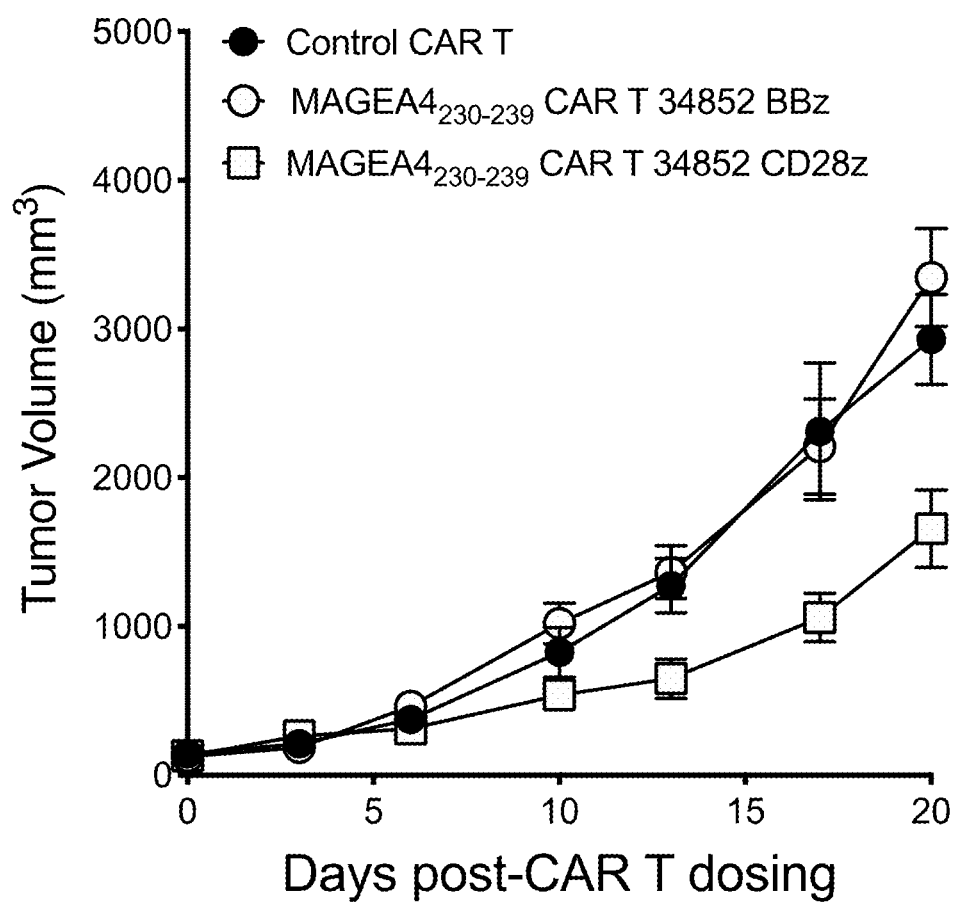
FIG. 12 shows illustrations of exemplary CAR constructs used in Example 6 and 8.

Example 8: Chimeric Antigen Receptors Containing Either an Anti-HLA-A2/MAGEA4$_{230\text{-}239}$ scFv Chimeric antigen receptors containing either an anti-HLA-A2/MAGEA4$_{230\text{-}239}$ SCFV in the V$_L$-V$_H$ orientation plus either 1) a huCD8 hinge/transmembrane domain, a 4-1BB co-stimulatory domain, and a CD3z signaling domain (BB/z CAR), or 2) huCD28 hinge/transmembrane/costimulatory domains and a CD3z signaling domain (28/z CAR) were constructed using the $V_L$ and $V_H$ sequences of an anti-HLA-A2/MAGEA4$_{230-239}$ antibody, 34852. As a non-binding control, a 28/z CAR was designed using an irrelevant scFv plus a huCD28 hinge/transmembrane/costimulatory domains and a CD3z signaling domain. These CARs were cloned into a pLVX lentiviral vector with an EF1a promoter and P2A:eGFP sequence (for tracking CAR-transduced cells), and VSV-pseudotyped lentivirus was produced. See FIG. 11 and FIG. 12 for construct design and results, respectively.

Collectively, the results demonstrate that anti-HLA-A2/MAGEA4$_{230-239}$ 28/z CAR T cells show superior in vivo anti-tumor activity and anti-tumor kinetics compared to anti-HLA-A2/MAGEA4$_{230-239}$ BB/z CAR T cells.

TABLE 24

CAR scFv IDs:

| AbPID | AbPID | Specificity | Description |
|---|---|---|---|
| 3B9 | 3B9 | Non-binding control | Anti-CD20 scFv 3B9 in VL-VH orientation with huCD28 hinge/transmembrane/costimulatory domains and a CD3z signaling domain (Control CAR) used in panels G-H |
| 34852 | 34852 | HLA-A2/ MAGEA4$_{230-239}$ | anti-HLA-A2/MAGEA4$_{230-239}$ 34852 in VH-VL orientation with huCD8 hinge/transmembrane domain, a 4-1BB co-stimulatory domain, and a CD3z signaling domain (HLA-A2/MAGEA4$_{230-239}$ CAR 34852 BB/z) |
| 34852 | 34852 | HLA-A2/ MAGEA4$_{230-239}$ | anti-HLA-A2/MAGEA4$_{230-239}$ 34852 in VH-VL orientation with huCD28 hinge/transmembrane/costimulatory domains and a CD3z signaling domain (HLA-A2/MAGEA4$_{230-239}$ CAR 34852 28/z) |

Experimental Procedure

Generation of CAR Constructs and CAR T Cells

Chimeric antigen receptors containing either an anti-HLA-A2/MAGEA4$_{230-239}$ SCFV in the $V_L$-$V_H$ orientation plus either 1) a huCD8 hinge/transmembrane domain, a 4-1BB co-stimulatory domain, and a CD3z signaling domain (BB/z CAR), or 2) huCD28 hinge/transmembrane/costimulatory domains and a CD3z signaling domain (28/z CAR) were constructed using the $V_L$ and $V_H$ sequences of an anti-HLA-A2/MAGEA4$_{230-239}$ antibody, 34852. As a non-binding control, a 28/z CAR was designed using an irrelevant scFv plus a huCD28 hinge/transmembrane/costimulatory domains and a CD3z signaling domain. These CARs were cloned into a pLVX lentiviral vector with an EF1a promoter and P2A:eGFP sequence (for tracking CAR-transduced cells), and VSV-pseudotyped lentivirus was produced.

CD3+ T cells were isolated from human peripheral blood mononuclear cells (PBMCs) from a normal donor, stimulated with CD3/CD28 microbeads plus 100 U/ml recombinant human IL-2, and transduced with the lentivirus at an MOI=5. The transduced cells were expanded for approximately 14 days with CD3/CD28 microbeads plus 100 U/ml recombinant human IL-2 before being cryopreserved until use during the in vivo experiment.

Implantation and Measurement of Xenogenic Tumors

To determine the in vivo efficacy of anti-HLA-A2/MAGEA4$_{230-239}$-targeted chimeric antigen receptor (CAR) T cells, a xenogenic tumor study was performed. On day 0, immunodeficient NOD.Cg-Prkdc$^{scid}$Il2rg$^{tm1Wjl}$/SzJ (NSG) mice were subcutaneously injected with 5×10$^6$ HLA-A2$^+$ MAGEA4$^+$ A375 human melanoma tumor cells. Using mass spectrometry techniques, it was determined that A375 melanoma cells express approximately 553 cell-surface copies of the HLA-A2/MAGEA4$_{230-239}$ peptide. On day 10 after tumors were established, the mice (n=5 per group) were intravenously injected with 4×10$^6$ T cells that express either the non-binding control 28/z CAR (Control CAR T), the anti-HLA-A2/MAGEA4$_{230-239}$ BB/z CAR, or the anti-HLA-A2/MAGEA4$_{230-239}$ 28/z CAR (as determined by the frequency of cells expressing either GFP, which is a marker for those cells that have been transduced with CAR) from two different donors. Tumor growth was assessed through day 28 by measuring tumor volumes.

Calculation of Xenogenic Tumor Growth and Inhibition

In order to determine tumor volume by external caliper, the greatest longitudinal diameter (length in mm) and the greatest transverse diameter (width in mm) were determined. Tumor volumes based on caliper measurements were calculated by the formula: Volume (mm$^3$)=(length×width$^2$)/2.

Results Summary and Conclusions

A375 tumors grew progressively in mice receiving Control CAR T cells. Mice receiving anti-HLA-A2/MAGEA4$_{230-239}$ BB/z CAR T cells did not demonstrate any tumor control. By contrast, anti-HLA-A2/MAGEA4$_{230-239}$ 28/z CAR T treatment led to suppression of established A375 tumor growth on days 17 (p<0.0001 vs. Control CAR T) and 20 (p<0.0001 vs. Control CAR T) (statistics analyzed by 2-way ANOVA). Enhanced efficacy of anti-HLA-A2/MAGEA4$_{230-239}$ 28/z CAR vs. anti-HLA-A2/MAGEA4$_{230-239}$ BB/z CAR is confirmed, as tumor sizes on days 13 (p=0.0256), 17 (p=0.0002), and 21 (p<0.0001) are statistically significantly different by 2-way ANOVA.

TABLE 25

Tabulated Data Summary:

| CAR T Treatment | Average Tumor Size (mm³) on Day 0 (day of CAR T dosing) | Tumor size standard error of the mean (SEM) |
|---|---|---|
| Control CAR T | 144.71 | 26.81 |
| MAGEA4$_{230-239}$ CAR T 34852 BB/z | 125.77 | 21.00 |
| MAGEA4$_{230-239}$ CAR T 34852 28/z | 130.64 | 13.71 |

| CAR T Treatment | Average Tumor Size (mm³) on Day 3 post-CAR T dosing | Tumor size standard error of the mean (SEM) |
|---|---|---|
| Control CAR T | 210.44 | 37.31 |
| MAGEA4$_{230-239}$ CAR T 34852 BB/z | 185.85 | 42.71 |
| MAGEA4$_{230-239}$ CAR T 34852 28/z | 263.48 | 44.05 |

| CAR T Treatment | Average Tumor Size (mm³) on Day 6 post-CAR T dosing | Tumor size standard error of the mean (SEM) |
|---|---|---|
| Control CAR T | 374.09 | 59.33 |
| MAGEA4$_{230-239}$ CAR T 34852 BB/z | 464.29 | 81.15 |
| MAGEA4$_{230-239}$ CAR T 34852 28/z | 312.28 | 33.90 |

| CAR T Treatment | Average Tumor Size (mm³) on Day 10 post-CAR T dosing | Tumor size standard error of the mean (SEM) |
|---|---|---|
| Control CAR T | 825.94 | 167.02 |
| MAGEA4$_{230-239}$ CAR T 34852 BB/z | 1018.90 | 137.83 |
| MAGEA4$_{230-239}$ CAR T 34852 28/z | 538.26 | 87.09 |

| CAR T Treatment | Average Tumor Size (mm³) on Day 13 post-CAR T dosing | Tumor size standard error of the mean (SEM) |
|---|---|---|
| Control CAR T | 1274.25 | 182.63 |
| MAGEA4$_{230-239}$ CAR T 34852 BB/z | 1365.24 | 178.27 |
| MAGEA4$_{230-239}$ CAR T 34852 28/z | 648.70 | 132.34 |

| CAR T Treatment | Average Tumor Size (mm³) on Day 17 post-CAR T dosing | Tumor size standard error of the mean (SEM) |
|---|---|---|
| Control CAR T | 2311.83 | 461.10 |
| MAGEA4$_{230-239}$ CAR T 34852 BB/z | 2209.72 | 321.33 |
| MAGEA4$_{230-239}$ CAR T 34852 28/z | 1058.88 | 163.82 |

| CAR T Treatment | Average Tumor Size (mm³) on Day 20 post-CAR T dosing | Tumor size standard error of the mean (SEM) |
|---|---|---|
| Control CAR T | 2930.09 | 302.64 |
| MAGEA4$_{230-239}$ CAR T 34852 BB/z | 3346.67 | 329.10 |
| MAGEA4$_{230-239}$ CAR T 34852 28/z | 1657.89 | 261.70 |

INCORPORATION BY REFERENCE

All publications, patents, patent applications and sequence accession numbers mentioned herein are hereby incorporated by reference in their entirety as if each individual publication, patent or patent application was specifically and individually indicated to be incorporated by reference. In case of conflict, the present application, including any definitions herein, will control.

EQUIVALENTS

A number of embodiments of the invention have been described. Nevertheless, it will be understood that various modifications may be made without departing from the spirit and scope of the invention. Accordingly, other embodiments are within the scope of the following claims. Unless defined otherwise, all technical and scientific terms used herein have the same meanings as commonly understood by one of skill in the art to which the disclosed invention belongs.

Those skilled in the art will recognize, or be able to ascertain using no more than routine experimentation, many equivalents to the specific embodiments of the invention described herein. Such equivalents are intended to be encompassed by the following claims.

SEQUENCE LISTING

```
Sequence total quantity: 41
SEQ ID NO: 1            moltype = AA  length = 39
FEATURE                 Location/Qualifiers
source                  1..39
                        mol_type = protein
                        organism = synthetic construct
SEQUENCE: 1
IEVMYPPPYL DNEKSNGTII HVKGKHLCPS PLFPGPSKP                               39

SEQ ID NO: 2            moltype = AA  length = 27
FEATURE                 Location/Qualifiers
source                  1..27
                        mol_type = protein
                        organism = synthetic construct
SEQUENCE: 2
FWVLVVVGGV LACYSLLVTV AFIIFWV                                            27
```

```
SEQ ID NO: 3              moltype = AA   length = 41
FEATURE                   Location/Qualifiers
source                    1..41
                          mol_type = protein
                          organism = synthetic construct
SEQUENCE: 3
RSKRSRLLHS DYMNMTPRRP GPTRKHYQPY APPRDFAAYR S                           41

SEQ ID NO: 4              moltype = AA   length = 317
FEATURE                   Location/Qualifiers
source                    1..317
                          mol_type = protein
                          organism = synthetic construct
SEQUENCE: 4
MSSEQKSQHC KPEEGVEAQE EALGLVGAQA PTTEEQEAAV SSSSPLVPGT LEEVPAAESA       60
GPPQSPQGAS ALPTTISFTC WRQPNEGSSS QEEEGPSTSP DAESLFREAL SNKVDELAHF       120
LLRKYRAKEL VTKAEMLERV IKNYKRCFPV IFGKASESLK MIFGIDVKEV DPASNTYTLV       180
TCLGLSYDGL LGNNQIFPKT GLLIIVLGTI AMEGDSASEE EIWEELGVMG VYDGREHTVY       240
GEPRKLLTQD WVQENYLEYR QVPGSNPARY EFLWGPRALA ETSYVKVLEH VVRVNARVRI       300
AYPSLREAAL LEEEEGV                                                     317

SEQ ID NO: 5              moltype = AA   length = 9
FEATURE                   Location/Qualifiers
source                    1..9
                          mol_type = protein
                          organism = synthetic construct
SEQUENCE: 5
KVLEHVVRV                                                              9

SEQ ID NO: 6              moltype = AA   length = 478
FEATURE                   Location/Qualifiers
source                    1..478
                          mol_type = protein
                          organism = synthetic construct
SEQUENCE: 6
DIQMTQSPSS LSASVGDRVT ITCRASQSIS SYLNWYQQKP GKAPKLLIYA VSILQSGVPS       60
RFSGSGSGTD FTLTINSLQP EDFATYSCQQ TYSTPPITFG QGTRLEIKGG GGSGGGGSGG       120
GGSEVQLLES GGGLVQPGGS LRLSCAASGF TFSSYAMTWV RQAPGMGLEW VSVISGSGSE       180
TYYADSVKGR FTISRDNSKN TLYLQMNSLR AEDTAVYYCV KDSSYRSSSR AYYYYGMDVW       240
GLGTTVTVSS GGGSTTTPA PRPPTPAPTI ASQPLSLRPE ACRPAAGGAV HTRGLDFACD       300
IYIWAPLAGT CGVLLLSLVI TLYCKRGRKK LLYIFKQPFM RPVQTTQEED GCSCRFPEEE       360
EGGCELRVKF SRSADAPAYQ QGQNQLYNEL NLGRREEYDV LDKRRGRDPE MGGKPRRKNP       420
QEGLYNELQK DKMAEAYSEI GMKGERRRGK GHDGLYQGLS TATKDTYDAL HMQALPPR         478

SEQ ID NO: 7              moltype = AA   length = 474
FEATURE                   Location/Qualifiers
source                    1..474
                          mol_type = protein
                          organism = synthetic construct
SEQUENCE: 7
DIQMTQSPSS LSASVGDRVT ITCRASQSIS SYLNWYQQKP GKAPKLLIYA VSILQSGVPS       60
RFSGSGSGTD FTLTINSLQP EDFATYSCQQ TYSTPPITFG QGTRLEIKGG GGSGGGGSGG       120
GGSEVQLLES GGGLVQPGGS LRLSCAASGF TFSSYAMTWV RQAPGMGLEW VSVISGSGSE       180
TYYADSVKGR FTISRDNSKN TLYLQMNSLR AEDTAVYYCV KDSSYRSSSR AYYYYGMDVW       240
GLGTTVTVSS GGGGSIEVMY PPPYLDNEKS NGTIIHVKGK HLCPSPLFPG PSKPFWVLVV       300
VGGVLACYSL LVTVAFIIFW VRSKRSRLLH SDYMNMTPRR PGPTRKHYQP YAPPRDFAAY       360
RSRVKFSRSA DAPAYQQGQN QLYNELNLGR REEYDVLDKR RGRDPEMGGK PRRKNPQEGL       420
YNELQKDKMA EAYSEIGMKG ERRRGKGHDG LYQGLSTATK DTYDALHMQA LPPR             474

SEQ ID NO: 8              moltype = AA   length = 470
FEATURE                   Location/Qualifiers
source                    1..470
                          mol_type = protein
                          organism = synthetic construct
SEQUENCE: 8
DIQMTQSPSS LSASVGDRVT ITCRASQSIS SYLNWYQQKP GKAPKLLIYA ASSLQSGVPS       60
RFSGSGSGTD FTLTISSLQP EDFATYYCQQ SYSTPPITFG QGTRLEIKRG GGGSGGGGSG       120
GGGSQVQLVE SGGGLVKPGG SLRLSCAASG FTFSEYYMTW IRQAPGQGLE WVSYISSSGF       180
NIYYADSVKG RFTISRDNAK NSLFLQMNSL RVEDTAVYYC AREGVTDGMD VWGQGTTVTV       240
SSGGGGSTTT PAPRPPTPAP TIASQPLSLR PEACRPAAGG AVHTRGLDFA CDIYIWAPLA       300
GTCGVLLLSL VITLYCKRGR KKLLYIFKQP FMRPVQTTQE EDGCSCRFPE EEEGGCELRV       360
KFSRSADAPA YQQGQNQLYN ELNLGRREEY DVLDKRRGRD PEMGGKPRRK NPQEGLYNEL       420
QKDKMAEAYS EIGMKGERRR GKGHDGLYQG LSTATKDTYD ALHMQALPPR                  470

SEQ ID NO: 9              moltype = AA   length = 466
FEATURE                   Location/Qualifiers
source                    1..466
                          mol_type = protein
```

```
                      organism = synthetic construct
SEQUENCE: 9
DIQMTQSPSS LSASVGDRVT ITCRASQSIS SYLNWYQQKP GKAPKLLIYA ASSLQSGVPS      60
RFSGSGSGTD FTLTISSLQP EDFATYYCQQ SYSTPPITFG QGTRLEIKRG GGGSGGGGSG     120
GGGSQVQLVE SGGGLVKPGG SLRLSCAASG FTFSEYYMTW IRQAPGQGLE WVSYISSSGF     180
NIYYADSVKG RFTISRDNAK NSLFLQMNSL RVEDTAVYYC AREGVTDGMD VWGQGTTVTV     240
SSGGGGSIEV MYPPPYLDNE KSNGTIIHVK GKHLCPSPLF PGPSKPFWVL VVVGGVLACY     300
SLLVTVAFII FWVRSKRSRL LHSDYMNMTP RRPGPTRKHY QPYAPPRDFA AYRSRVKFSR     360
SADAPAYQQG QNQLYNELNL GRREEYDVLD KRRGRDPEMG GKPRRKNPQE GLYNELQKDK     420
MAEAYSEIGM KGERRRGKGH DGLYQGLSTA TKDTYDALHM QALPPR                    466

SEQ ID NO: 10           moltype = AA  length = 478
FEATURE                 Location/Qualifiers
source                  1..478
                        mol_type = protein
                        organism = synthetic construct
SEQUENCE: 10
EVQLVESGGG VVQPGGSLRL SCEASGFIFD DYAMHWVRQA PGKGLEWVSL ISGDGDIIYY      60
ADSVKGRFTI SRDNSKNSLY LQMNSLIIED TALYYCAKDW VFGVVMTHYW YFGLDVWGQG     120
TTVTVSSGGG GSGGGGSGGG GSDIQMTQSP SSLSASEGDR VTITCRASQS ISTYLNWYQQ     180
KPGKAPKLLI YGASSLQSGV PSRFSGSGSG TDFTLTISSL QPEDFATYYC QQSYSTPPIT     240
FGQGTKVEIK GGGGSTTTPA PRPPTPAPTI ASQPLSLRPE ACRPAAGGAV HTRGLDFACD     300
IYIWAPLAGT CGVLLLSLVI TLYCKRGRKK LLYIFKQPFM RPVQTTQEED GCSCRFPEEE     360
EGGCELRVKF SRSADAPAYQ QGQNQLYNEL NLGRREEYDV LDKRRGRDPE MGGKPRRKNP     420
QEGLYNELQK DKMAEAYSEI GMKGERRRGK GHDGLYQGLS TATKDTYDAL HMQALPPR       478

SEQ ID NO: 11           moltype = AA  length = 474
FEATURE                 Location/Qualifiers
source                  1..474
                        mol_type = protein
                        organism = synthetic construct
SEQUENCE: 11
EVQLVESGGG VVQPGGSLRL SCEASGFIFD DYAMHWVRQA PGKGLEWVSL ISGDGDIIYY      60
ADSVKGRFTI SRDNSKNSLY LQMNSLIIED TALYYCAKDW VFGVVMTHYW YFGLDVWGQG     120
TTVTVSSGGG GSGGGGSGGG GSDIQMTQSP SSLSASEGDR VTITCRASQS ISTYLNWYQQ     180
KPGKAPKLLI YGASSLQSGV PSRFSGSGSG TDFTLTISSL QPEDFATYYC QQSYSTPPIT     240
FGQGTKVEIK GGGGSIEVMY PPPYLDNEKS NGTIIHVKGK HLCPSPLFPG PSKPFWVLVV     300
VGGVLACYSL LVTVAFIIFW VRSKRSLLH SDYMNMTPRR PGPTRKHYQP YAPPRDFAAY      360
RSRVKFSRSA DAPAYQQGQN QLYNELNLGR REEYDVLDKR GRDPEMGGK PRRKNPQEGL      420
YNELQKDKMA EAYSEIGMKG ERRRGKGHDG LYQGLSTATK DTYDALHMQA LPPR           474

SEQ ID NO: 12           moltype = AA  length = 466
FEATURE                 Location/Qualifiers
source                  1..466
                        mol_type = protein
                        organism = synthetic construct
SEQUENCE: 12
DIQMTQSPAS LSVSVGETVT ITCRASDIIY SNLAWYQQKQ GKSPQLLVYA ATNLAAGVPS      60
RFSGSGSGTQ YSLKINSLQS EDFGTYYCQH FWGSSISFGS GTKLEIKGGG GSGGGGSGGG     120
GSQVQLKESG PGLVAPSQSL SITCTVSGFS LTSYGVHWVR QPPGKGLEWL GVIWAGGTTN     180
YNSALMSRLS ISRDNSKSQV FLEMNSLQTD DTAIYYCARD GHFHFDFWGQ GTTLTVSSGG     240
GGSTTTPAPR PPTPAPTIAS QPLSLRPEAC RPAAGGAVHT RGLDFACDIY IWAPLAGTCG     300
VLLLSLVITL YCKRGRKKLL YIFKQPFMRP VQTTQEEDGC SCRFPEEEEG GCELRVKFSR     360
SADAPAYQQG QNQLYNELNL GRREEYDVLD KRRGRDPEMG GKPRRKNPQE GLYNELQKDK     420
MAEAYSEIGM KGERRRGKGH DGLYQGLSTA TKDTYDALHM QALPPR                    466

SEQ ID NO: 13           moltype = AA  length = 462
FEATURE                 Location/Qualifiers
source                  1..462
                        mol_type = protein
                        organism = synthetic construct
SEQUENCE: 13
DIQMTQSPAS LSVSVGETVT ITCRASDIIY SNLAWYQQKQ GKSPQLLVYA ATNLAAGVPS      60
RFSGSGSGTQ YSLKINSLQS EDFGTYYCQH FWGSSISFGS GTKLEIKGGG GSGGGGSGGG     120
GSQVQLKESG PGLVAPSQSL SITCTVSGFS LTSYGVHWVR QPPGKGLEWL GVIWAGGTTN     180
YNSALMSRLS ISRDNSKSQV FLEMNSLQTD DTAIYYCARD GHFHFDFWGQ GTTLTVSSGG     240
GGSIEVMYPP PYLDNEKSNG TIIHVKGKHL CPSPLFPGPS KPFWVLVVVG GVLACYSLLV     300
TVAFIIFWVR SKRSLLHSD YMNMTPRRPG PTRKHYQPYA PPRDFAAYRS RVKFSRSADA      360
PAYQQGQNQL YNELNLGRRE EYDVLDKRRG RDPEMGGKPR RKNPQEGLYN ELQKDKMAEA     420
YSEIGMKGER RRGKGHDGLY QGLSTATKDT YDALHMQALP PR                        462

SEQ ID NO: 14           moltype = DNA  length = 1411
FEATURE                 Location/Qualifiers
source                  1..1411
                        mol_type = other DNA
                        organism = synthetic construct
SEQUENCE: 14
catccagatg acccagtctc catcctccct gtctgcatct gtaggagaca gagtcaccat      60
cacttgccgg gcaagtcaga gcattagcag ctatttaaat tggtatcagc agaaaccagg     120
```

```
gaaagcccct aagctcctga tctatgctgc atccagtttg caaagtgggg tcccgtcaag    180
gttcagtggc agtggatctg ggacagattt cactctcacc atcagcagtc tgcaacctga    240
agattttgca acttactact gtcaacagag ttacagtacc cctccgatca ccttcggcca    300
agggacacga ctggagatta aacgaggtgg aggcggtagt ggcggaggcg aagtggtgg     360
aggaggctca caggtgcagc tggtggagtc tgggggaggc ttggtcaagc ctggagggtc    420
cctgagactc tcctgtgcag cctctggatt cactttcagt gaatactaca tgacctggat    480
ccgccaggct ccagggcagg gctggagtg gtttcatac attagtagta gtggttttaa      540
catatactac gcagactctg tgaagggccg attcaccatc tcaagggaca acgccaagaa    600
ctcactgttt ctgcaaatga acagcctgag agtcgaggac acggccgtat attactgtgc    660
gagagaaggt gtaacggacg gtatggacgt ctggggccaa gggaccacgg tcaccgtctc    720
ctcaggaggt ggtggaagta ctaccactcc tgctccccgc ccccaacac ctgctccaac     780
tattgcatcc caaccactct ccctcagacc cgaagcttgt cgccccgccg ccggaggtgc    840
tgttcacact agaggactcg attttgcttg cgacatttat atctgggccc cacttgcagg    900
tacttgcgga gtattgctgc tctcacttgt tattactctt tattgcaaac ggggcagaaa    960
gaaactcctg tatatattca acaaccatt tatgagacca gtacaaacta ctcaagagga    1020
agatggctgt agctgccgat tccagaaga agaaggaa ggatgtgaac tgagagtgaa      1080
gttcagcagg agcgcagacg ccccccgcgta ccagcagggc cagaaccagc tctataacga   1140
gctcaatcta ggacgaagag aggagtacga tgttttggac aagagacgtg gccgggaccc   1200
tgagatgggg ggaaagccga aaggaagaa ccctcaggaa ggcctgtaca atgaactgca    1260
gaaagataag atgcggagg cctacagtga gattgggatg aaaggcgagc gccggagggg    1320
caaggggcac gatggccttt accagggtct cagtacagcc accaaggaca cctacgacgc    1380
ccttcacatg caggccctgc cccctcgcta a                                  1411

SEQ ID NO: 15        moltype = DNA   length = 1413
FEATURE              Location/Qualifiers
source               1..1413
                     mol_type = other DNA
                     organism = synthetic construct
SEQUENCE: 15
gacatccaga tgacccagtc tccatcctcc ctgtctgcat ctgtaggaga cagagtcacc     60
atcacttgcc gggcaagtca gagcattagc agctatttaa attggtatca gcagaaacca   120
gggaaagccc ctaagctcct gatctatgct gcatccagtt tgcaaagtgg ggtcccgtca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacac gactggagat taaacgaggt ggaggcggta gtggcggagg cggaagtggt   360
ggaggaggct cacaggtgca gctggtggag tctgggggag gcttggtcaa gcctggaggg   420
tccctgagac tctcctgtgc agcctctgga ttcactttca gtgaatacta catgacctgg   480
atccgccagg ctccagggca ggggctggag tgggtttcat acattagtag tagtggtttt   540
aacatatact acgcagactc tgtgaagggc cgattcacca tctcaaggga caacgccaag   600
aactcactgt ttctgcaaat gaacagcctg agagtcgagg acacggccgt atattactgt   660
gcgagagaag gtgtaacgga cggtatggac gtctggggcc aagggaccac ggtcaccgtc   720
tcctcaggag gtggtggaag tactaccact cctgctcccc gccccccaac acctgctcca   780
actattgcat cccaaccact ctccctcaga cccgaagctt gtcgccccgc cgccggaggt   840
gctgttcaca ctagaggact cgattttgct tgcgacattt atatctgggc cccacttgca   900
ggtacttgcg gagtattgct gctctcactt gttattactc tttattgcaa acggggcaga   960
aagaaactcc tgtatatatt caacaaccat ttatgagaca gtacaaac tactcaagag    1020
gaagatggct gtagctgccg atttccagaa gaagaaggaa ggatgtgaa actgagagtg    1080
aagttcagca ggagcgcaga cgccccccgc gtaccagcag ggccagaacc agctctataa   1140
cgagctcaat ctaggacgaa gagaggagta cgatgttttg gacaagacg tggccggga     1200
cctgagatgg ggggaaagcc gagaaggaag aacctcagg aaggcctgta caatgaactg    1260
cagaaagata gatggcgga ggcctacagt gagattggga tgaaggcga gcgccggagg    1320
ggcaaggggc acgatggcct ttaccagggt ctcagtacag ccaccaagga cacctacgac   1380
gcccttcaca tgcaggccct gccccctcgc taa                                1413

SEQ ID NO: 16        moltype = AA    length = 108
FEATURE              Location/Qualifiers
source               1..108
                     mol_type = protein
                     organism = synthetic construct
SEQUENCE: 16
DIQMTQSPSS LSASVGDRVT ITCRASQSIS SYLNWYQQKP GKAPKLLIYA VSILQSGVPS     60
RFSGSGSGTD FTLTINSLQP EDFATYSCQQ TYSTPPITFG QGTRLEIK                 108

SEQ ID NO: 17        moltype = AA    length = 109
FEATURE              Location/Qualifiers
source               1..109
                     mol_type = protein
                     organism = synthetic construct
SEQUENCE: 17
DIQMTQSPSS LSASVGDRVT ITCRASQSIS SYLNWYQQKP GKAPKLLIYA ASSLQSGVPS     60
RFSGSGSGTD FTLTISSLQP EDFATYYCQQ SYSTPPITFG QGTRLEIKR                109

SEQ ID NO: 18        moltype = AA    length = 108
FEATURE              Location/Qualifiers
source               1..108
                     mol_type = protein
                     organism = synthetic construct
SEQUENCE: 18
DIQMTQSPSS LSASEGDRVT ITCRASQSIS TYLNWYQQKP GKAPKLLIYG ASSLQSGVPS     60
```

```
RFSGSGSGTD FTLTISSLQP EDFATYYCQQ SYSTPPITFG QGTKVEIK            108

SEQ ID NO: 19           moltype = AA  length = 107
FEATURE                 Location/Qualifiers
source                  1..107
                        mol_type = protein
                        organism = synthetic construct
SEQUENCE: 19
DIQMTQSPAS LSVSVGETVT ITCRASDIIY SNLAWYQQKQ GKSPQLLVYA ATNLAAGVPS   60
RFSGSGSGTQ YSLKINSLQS EDFGTYYCQH FWGSSISFGS GTKLEIK               107

SEQ ID NO: 20           moltype = AA  length = 127
FEATURE                 Location/Qualifiers
source                  1..127
                        mol_type = protein
                        organism = synthetic construct
SEQUENCE: 20
EVQLLESGGG LVQPGGSLRL SCAASGFTFS SYAMTWVRQA PGMGLEWVSV ISGSGSETYY   60
ADSVKGRFTI SRDNSKNTLY LQMNSLRAED TAVYYCVKDS SYRSSSRAYY YYGMDVWGLG  120
TTVTVSS                                                          127

SEQ ID NO: 21           moltype = AA  length = 118
FEATURE                 Location/Qualifiers
source                  1..118
                        mol_type = protein
                        organism = synthetic construct
SEQUENCE: 21
QVQLVESGGG LVKPGGSLRL SCAASGFTFS EYYMTWIRQA PGQGLEWVSY ISSSGFNIYY   60
ADSVKGRFTI SRDNAKNSLF LQMNSLRVED TAVYYCAREG VTDGMDVWGQ GTTVTVSS   118

SEQ ID NO: 22           moltype = AA  length = 127
FEATURE                 Location/Qualifiers
source                  1..127
                        mol_type = protein
                        organism = synthetic construct
SEQUENCE: 22
EVQLVESGGG VVQPGGSLRL SCEASGFIFD DYAMHWVRQA PGKGLEWVSL ISGDGDIIYY   60
ADSVKGRFTI SRDNSKNSLY LQMNSLIIED TALYYCAKDW VFGVVMTHYW YFGLDVWGQG  120
TTVTVSS                                                          127

SEQ ID NO: 23           moltype = AA  length = 116
FEATURE                 Location/Qualifiers
source                  1..116
                        mol_type = protein
                        organism = synthetic construct
SEQUENCE: 23
QVQLKESGPG LVAPSQSLSI TCTVSGFSLT SYGVHWVRQP PGKGLEWLGV IWAGGTTNYN   60
SALMSRLSIS RDNSKSQVFL EMNSLQTDDT AIYYCARDGH FHFDFWGQGT TLTVSS     116

SEQ ID NO: 24           moltype = DNA  length = 326
FEATURE                 Location/Qualifiers
source                  1..326
                        mol_type = other DNA
                        organism = synthetic construct
SEQUENCE: 24
acatccagat gacccagtct ccatcctccc tgtctgcatc tgtaggagac agagtcacca   60
tcacttgccg ggcaagtcag agcattagca gctatttaaa ttggtatcag cagaaaccag  120
ggaaagcccc taagctcctg atctatgctg catccagttt gcaaagtggg gtcccgtcaa  180
ggttcagtgg cagtggatct gggacagatt tcactctcac catcagcagt ctgcaacctg  240
aagattttgc aacttactac tgtcaacaga gttacagtac cctccgatc accttcggcc    300
aagggacacg actggagatt aaacga                                      326

SEQ ID NO: 25           moltype = DNA  length = 353
FEATURE                 Location/Qualifiers
source                  1..353
                        mol_type = other DNA
                        organism = synthetic construct
SEQUENCE: 25
aggtgcagct ggtggagtct gggggaggct tggtcaagcc tggagggtcc ctgagactct   60
cctgtgcagc ctctggattc actttcagtg aatactacat gacctggatc cgccaggctc  120
cagggcaggg gctggagtgg gtttcataca ttagtagtag tggttttaac atatactacg  180
cagactctgt gaagggccga ttcaccatct caagggacaa cgccaagaac tcactgtttc  240
tgcaaatgaa cagcctgaga gtcgaggaca cggccgtata ttactgtgcg agagaaggtg  300
taacggacgg tatggacgtc tggggccaag ggaccacggt caccgtctcc tca        353

SEQ ID NO: 26           moltype = AA  length = 112
FEATURE                 Location/Qualifiers
source                  1..112
                        mol_type = protein
```

```
                    organism = synthetic construct
SEQUENCE: 26
RVKFSRSADA PAYQQGQNQL YNELNLGRRE EYDVLDKRRG RDPEMGGKPR RKNPQEGLYN    60
ELQKDKMAEA YSEIGMKGER RRGKGHDGLY QGLSTATKDT YDALHMQALP PR           112

SEQ ID NO: 27           moltype = AA  length = 69
FEATURE                 Location/Qualifiers
source                  1..69
                        mol_type = protein
                        organism = synthetic construct
SEQUENCE: 27
TTTPAPRPPT PAPTIASQPL SLRPEACRPA AGGAVHTRGL DFACDIYIWA PLAGTCGVLL    60
LSLVITLYC                                                           69

SEQ ID NO: 28           moltype = AA  length = 42
FEATURE                 Location/Qualifiers
source                  1..42
                        mol_type = protein
                        organism = synthetic construct
SEQUENCE: 28
KRGRKKLLYI FKQPFMRPVQ TTQEEDGCSC RFPEEEEGGC EL                      42

SEQ ID NO: 29           moltype = AA  length = 732
FEATURE                 Location/Qualifiers
source                  1..732
                        mol_type = protein
                        organism = synthetic construct
SEQUENCE: 29
DIQMTQSPSS LSASVGDRVT ITCQASQDIS NYLNWYQQKR GKAPKLLIYD ASILETGVPS    60
RFSGSGSGTD FTFTISSLQP EDIATYFCQQ FDNVPLTFGG GTKVEIKGGG GSGGGGSGGG   120
GSEVQLVESG GGLVQPGRSL RLSCAASGFT FDDYAMHWVR QAPGKGLEWV SGISWNSGSI   180
AYADSVKGRF TISRDNAKNS LYLQMNSLRS EDTALYHCAK DWRRTNYYGM DVWGQGTTVT   240
VSSGGGGSTT TPAPRPPTPA PTIASQPLSL RPEACRPAAG GAVHTRGLDF ACDIYIWAPL   300
AGTCGVLLLS LVITLYCKRG RKKLLYIFKQ PFMRPVQTTQ EEDGCSCRFP EEEEGGCELR   360
VKFSRSADAP AYQQGQNQLY NELNLGRREE YDVLDKRRGR DPEMGGKPRR KNPQEGLYNE   420
LQKDKMAEAY SEIGMKGERR RGKGHDGLYQ GLSTATKDTY DALHMQALPP RGSGATNFSL   480
LKQAGDVEEN PGPMVSKGEE LFTGVVPILV ELDGDVNGHK FSVSGEGEGD ATYGKLTLKF   540
ICTTGKLPVP WPTLVTTLTY GVQCFSRYPD HMKQHDFFKS AMPEGYVQER TIFFKDDGNY   600
KTRAEVKFEG DTLVNRIELK GIDFKEDGNI LGHKLEYNYN SHNVYIMADK QKNGIKVNFK   660
IRHNIEDGSV QLADHYQQNT PIGDGPVLLP DNHYLSTQSA LSKDPNEKRD HMVLLEFVTA   720
AGITLGMDEL YK                                                      732

SEQ ID NO: 30           moltype = AA  length = 728
FEATURE                 Location/Qualifiers
source                  1..728
                        mol_type = protein
                        organism = synthetic construct
SEQUENCE: 30
DIQMTQSPSS LSASVGDRVT ITCQASQDIS NYLNWYQQKR GKAPKLLIYD ASILETGVPS    60
RFSGSGSGTD FTFTISSLQP EDIATYFCQQ FDNVPLTFGG GTKVEIKGGG GSGGGGSGGG   120
GSEVQLVESG GGLVQPGRSL RLSCAASGFT FDDYAMHWVR QAPGKGLEWV SGISWNSGSI   180
AYADSVKGRF TISRDNAKNS LYLQMNSLRS EDTALYHCAK DWRRTNYYGM DVWGQGTTVT   240
VSSGGGGSIE VMYPPPYLDN EKSNGTIIHV KGKHLCPSPL FPGPSKPFWV LVVVGGVLAC   300
YSLLVTVAFI IFWVRSKRSR LLHSDYMNMT PRRPGPTRKH YQPYAPPRDF AAYRSVKFS    360
RSADAPAYQQ GQNQLYNELN LGRREEYDVL DKRRGRDPEM GGKPRRKNPQ EGLYNELQKD   420
KMAEAYSEIG MKGERRRGKG HDGLYQGLST ATKDTYDALH MQALPPRGSG ATNFSLLKQA   480
GDVEENPGPM VSKGEELFTG VVPILVELDG DVNGHKFSVS GEGEGDATYG KLTLKFICTT   540
GKLPVPWPTL VTTLTYGVQC FSRYPDHMKQ HDFFKSAMPE GYVQERTIFF KDDGNYKTRA   600
EVKFEGDTLV NRIELKGIDF KEDGNILGHK LEYNYNSHNV YIMADKQKNG IKVNFKIRHN   660
IEDGSVQLAD HYQQNTPIGD GPVLLPDNHY LSTQSALSKD PNEKRDHMVL LEFVTAAGIT   720
LGMDELYK                                                           728

SEQ ID NO: 31           moltype = AA  length = 107
FEATURE                 Location/Qualifiers
source                  1..107
                        mol_type = protein
                        organism = synthetic construct
SEQUENCE: 31
DIQMTQSPSS LSASVGDRVT ITCQASQDIS NYLNWYQQKR GKAPKLLIYD ASILETGVPS    60
RFSGSGSGTD FTFTISSLQP EDIATYFCQQ FDNVPLTFGG GTKVEIK                 107

SEQ ID NO: 32           moltype = AA  length = 121
FEATURE                 Location/Qualifiers
source                  1..121
                        mol_type = protein
                        organism = synthetic construct
SEQUENCE: 32
EVQLVESGGG LVQPGRSLRL SCAASGFTFD DYAMHWVRQA PGKGLEWVSG ISWNSGSIAY    60
ADSVKGRFTI SRDNAKNSLY LQMNSLRSED TALYHCAKDW RRTNYYGMDV WGQGTTVTVS   120
```

```
SEQ ID NO: 33            moltype = AA  length = 739
FEATURE                  Location/Qualifiers
source                   1..739
                         mol_type = protein
                         organism = synthetic construct
SEQUENCE: 33
EVQLLESGGG LVQPGGSLRL TCAASGFTFR SYAMSWVRQA PGKGLEWVST ISGNSDSTYY      60
ADSVKGRFTI SRENSKNTLY LQMNSLRAED TAVYYCAKDL HITMVRGAIP ADVFDIWGQG     120
TMVTVSSGGG GSGGGGSGGG GSDIQMTQSP SSLSASVGDR VTITCRASQS ISFYLNWYQQ     180
KPGKAPKLLI YAASSLQSGV PSRFSGSGSE TDFTLTISSL QPEDFATYYC QQSYSTPPIT     240
FGQGTRLEIK GGGGSTTTPA PRPPTPAPTI ASQPLSLRPE ACRPAAGGAV HTRGLDFACD     300
IYIWAPLAGT CGVLLLSLVI TLYCKRGRKK LLYIFKQPFM RPVQTTQEED GCSCRFPEEE     360
EGGCELRVKF SRSADAPAYQ QGQNQLYNEL NLGRREEYDV LDKRRGRDPE MGGKPRRKNP     420
QEGLYNELQK DKMAEAYSEI GMKGERRRGK GHDGLYQGLS TATKDTYDAL HMQALPPRGS     480
GATNFSLLKQ AGDVEENPGP MVSKGEELFT GVVPILVELD GDVNGHKFSV SGEGEGDATY     540
GKLTLKFICT TGKLPVPWPT LVTTLTYGVQ CFSRYPDHMK QHDFFKSAMP EGYVQERTIF     600
FKDDGNYKTR AEVKFEGDTL VNRIELKGID FKEDGNILGH KLEYNYNSHN VYIMADKQKN     660
GIKVNFKIRH NIEDGSVQLA DHYQQNTPIG DGPVLLPDNH YLSTQSALSK DPNEKRDHMV     720
LLEFVTAAGI TLGMDELYK                                                 739

SEQ ID NO: 34            moltype = AA  length = 735
FEATURE                  Location/Qualifiers
source                   1..735
                         mol_type = protein
                         organism = synthetic construct
SEQUENCE: 34
EVQLLESGGG LVQPGGSLRL TCAASGFTFR SYAMSWVRQA PGKGLEWVST ISGNSDSTYY      60
ADSVKGRFTI SRENSKNTLY LQMNSLRAED TAVYYCAKDL HITMVRGAIP ADVFDIWGQG     120
TMVTVSSGGG GSGGGGSGGG GSDIQMTQSP SSLSASVGDR VTITCRASQS ISFYLNWYQQ     180
KPGKAPKLLI YAASSLQSGV PSRFSGSGSE TDFTLTISSL QPEDFATYYC QQSYSTPPIT     240
FGQGTRLEIK GGGGSIEVMY PPPYLDNEKS NGTIIHVKGK HLCPSPLFPG PSKPFWVLVV     300
VGGVLACYSL LVTVAFIIFW VRSKRSRLLH SDYMNMTPRR PGPTRKHYQP YAPPRDFAAY     360
RSRVKFSRSA DAPAYQQGQN QLYNELNLGR REEYDVLDKR RGRDPEMGGK PRRKNPQEGL     420
YNELQKDKMA EAYSEIGMKG ERRRGKGHDG LYQGLSTATK DTYDALHMQA LPPRGSGATN     480
FSLLKQAGDV EENPGPMVSK GEELFTGVVP ILVELDGDVN GHKFSVSGEG EGDATYGKLT     540
LKFICTTGKL PVPWPTLVTT LTYGVQCFSR YPDHMKQHDF FKSAMPEGYV QERTIFFKDD     600
GNYKTRAEVK FEGDTLVNRI ELKGIDFKED GNILGHKLEY NYNSHNVYIM ADKQKNGIKV     660
NFKIRHNIED GSVQLADHYQ QNTPIGDGPV LLPDNHYLST QSALSKDPNE KRDHMVLLEF     720
VTAAGITLGM DELYK                                                     735

SEQ ID NO: 35            moltype = DNA  length = 2220
FEATURE                  Location/Qualifiers
source                   1..2220
                         mol_type = other DNA
                         organism = synthetic construct
SEQUENCE: 35
gaggtgcagc tgctggagag cggaggaggc ctggtgcagc ctggaggaag cctgaggctg      60
acatgcgcag catccggctt caccttccgc tcttacgcaa tgagctgggt gcggcaggca     120
ccaggcaagg gactggagtg ggtgagcaca atctccggaa attctgacag cacctactac     180
gccgattccg tgaagggccg ctttacaatc tcccgggaga actctaagaa taccctgtat     240
ctgcagatga actctctgcg ggccgaggac acagccgtgt actattgcgc caaggatctg     300
cacatcacca tggtgagagg agcaatccca gcagacgtgt tcgatatctg gggccagggc     360
acaatggtga ccgtgagctc cggaggagga ggatccggcg gaggaggctc tggaggagga     420
ggaagcgaca tccagatgac ccagagccct tctagcctgt ccgcctctgt gggcgataga     480
gtgacaatca cctgtagggc cagccagtcc atctcttttt acctgaattg gtatcagcag     540
aagcccggca aggcccctaa gctgctgatc tacgcagcat cctctctgca gagcggagtg     600
ccatccaggt tcagcggatc cggctctgag acagacttta cactgaccat cagctccctg     660
cagcctgagg atttcgccac ctactattgc cagcagagct attccacacc cctatcacc      720
tttggccagg gaaccaggct ggagatcaag ggaggaggag gatccaccac aaccccagcc     780
cctcgcccac ccacaccagc accaaccatc gcatctcagc cactgagcct gagacctgag     840
gcctgtaggc cagcagcagg aggagcagtg cacaccaggg gactggactt cgcctgcgat     900
atctacatct gggcaccact ggcaggaaca tgtggcctgc tgctgctgag cctggtgatt     960
acctgtacct gcaagagagg caggaagaag ctgctgtata tcttcaagca gcccttcatg    1020
cggcccgtgc agacaaccca ggaggaggac ggctgctcct gtagattccc tgaagaagag    1080
gagggaggat gtgagctgag ggtgaagttt ctcggagcg ccgatgcacc agcataccag    1140
caggacagag accagctgta taacgagctg aatctgggcc ggagagagga gtacgacgtg    1200
ctggataaga ggcggggcag agacccagag atggggaagc ccccggaa aaagaacct     1260
caggagggcc tgtacaatga gctgcagaag gacaagatgg ccgaggccta tagcgagatc    1320
ggcatgaagg gagagaggcg ccggggcaag ggacacgatg gcctgtacca gggcctgtcc    1380
acagccacca ggacacata tgatgccctg cacatgcagg ccctgcctcc aagaggatcc    1440
ggagccacca cttttctct gctgaagcag gcaggcgacg tggaggagaa tcctggacca    1500
atgtgagca agggagagga gctgttcacc ggagtggtgc caatcctggt ggagctggat    1560
ggcgatgtga atggccacaa gttttccgtg tctggagagg agagggcga tgcaactac    1620
ggcaagctga ccctgaagtt catctgcaca accggcaagc tgcccgtgcc ttggccaaca    1680
ctggtgacaa ccctgaccta cggcgtgcag tgtttctcta gatatccaga ccacatgaag    1740
cagcacgatt tctttaagag cgccatgcc gagggctacg tgcaggagag aaccatcttc    1800
ttaaggacg atggcaacta taagacaagg gccgaggtga agttcgaggg cgacaccctg    1860
```

```
gtgaaccgca tcgagctgaa gggcatcgac tttaaggagg atggcaatat cctgggccac  1920
aagctggagt acaactataa ttctcacaac gtgtacatca tggccgataa gcagaagaac  1980
ggcatcaagg tgaacttcaa gatcaggcac aaatatcgagg acggctccgt gcagctggcc  2040
gatcactacc agcagaacac accaatcggc gacggccctg tgctgctgcc agataatcac  2100
tatctgtcta cccagagcgc cctgtccaag gaccccaacg agaagcgcga tcacatggtg  2160
ctgctggagt tcgtgacagc agcaggaatc acctgggaa tggacgagct gtataagtga  2220
```

| SEQ ID NO: 36 | moltype = DNA  length = 2208 |
|---|---|
| FEATURE | Location/Qualifiers |
| source | 1..2208 |
| | mol_type = other DNA |
| | organism = synthetic construct |

SEQUENCE: 36

```
gaggtgcagc tgctggagag cggaggaggc ctggtgcagc ctggaggatc tctgaggctg  60
acctgcgcag caagcggctt cacatttcgc tcctacgcaa tgtctggt gcggcaggca  120
ccaggcaagg gactggagtg ggtgagcacc atctccggca attctgacag cacatactat  180
gccgattctg tgaagggccg ctttaccatc agccggaga actccaagaa tacactgtat  240
ctgcagatga acagcctgag ggccgaggac accgccgtac actattgtgc caaggatctg  300
cacatcacaa tggtgcgcgg agcaatccca gcagacgtgt tcgatatctg gggccagggc  360
accatggtga cagtgagctc cggaggagga ggatccggcg gaggaggctc tggaggagga  420
ggaagcgaca tccagatgac ccagagccct tctagcctgt ccgcctctgt gggcgataga  480
gtgaccatca catgcagggc cagccagtcc atctcttttct acctgaactg gtatcagcag  540
aagccaggca agggccccaa gctgctgatc tacgcagcat cctctctgca gtctggagtg  600
ccaagcaggt tcagcggatc cggatctgag accgacttta ccctgacaat cagctccctg  660
cagcctgagg atttcgccac atactattgt cagcagagct attccacccc ccctatcaca  720
tttggccagg gaaccaggct ggagatcaag ggaggaggcg gcagcatcga agtgatgtac  780
ccaccccctt atctggacaa cgagaagtcc aatggcacaa tcatccacgt gaagggcaag  840
cacctgtgcc caagccctct gttcccagga ccatccaagc ccttttgggt gctggtggtg  900
gtgggaggcg tgctggcctg ttactccctg ctggtgaccg tggccttcat catcttttgg  960
gtgagatcta agccgcagccg gctgctgcac tctgattata tgaatatgac cccacggaga  1020
cctggcccaa caagaaagca ctaccagcca tatgcaccac caagggactt cgcagcctac  1080
agaagcaggt gaagttttc tcggagcgcc gatgcaccag cataccagca gggacagaac  1140
cagctgtata cgagctgaa tctgggcagg cgcgaggagt atgacgtgct ggataagcgg  1200
agaggcagag accctgagat gggaggcaag ccaaggagga agaaccctca ggagggcctg  1260
tacaatgagc tgcagaagga caagatggcc gaggcctata gcgagatcgg catgaaggga  1320
gagcggagaa ggggcaaggg acacgatggc ctgtaccagg gcctgtccac cgccacaaag  1380
gacacctatg atgccctgca catgcaggcc ctgcctccaa gggatccgg agccacaaac  1440
ttttctctgc tgaagcaggc aggcgacgtg gaggagaatc aggacctat ggtgtccaag  1500
ggagaggagc tgttcaccgg agtggtgcca atcctgatgg agctggacgg cgatgtgaat  1560
ggccacaagt tttccgtgtc tggagaggga gagggcgatg caacctacg caagctgaca  1620
ctgaagttca tctgcaccac aggcaagctg ccagtgcccct ggcctaccct ggtgaccaca  1680
ctgacatacg gcgtgcagtg tttctcccgc tatcctgacc acatgaagca gcacgatttc  1740
tttaagtctg ccatgccaga gggctacgtg caggagcgca ccatcttctt taaggacgat  1800
ggcaactata gaacccgggc cgaggtgaag ttcgagggcg acacactggt gaacagaatc  1860
gagctgaagg gcatcgactt taaggaggat ggcaatatcc tgggcacaa gctggagtac  1920
aactataata gccacaacgt gtacatcatg gccgataagc agaagaacgg catcaaggtg  1980
aacttcaaga tccggcacaa tatcgaggac ggctccgtgc agctggccgt tcactaccag  2040
cagaacaccc caatcggcga cggacctgtg ctgctgccag ataatcacta tctgtccaca  2100
cagtctgccc tgagcaagga ccccaacgag aagagagatc acatggtgct gctggagttc  2160
gtgaccgcag caggaatcac actgggaatg gacgagctgt acaagtga  2208
```

| SEQ ID NO: 37 | moltype = AA  length = 108 |
|---|---|
| FEATURE | Location/Qualifiers |
| source | 1..108 |
| | mol_type = protein |
| | organism = synthetic construct |

SEQUENCE: 37

```
DIQMTQSPSS LSASVGDRVT ITCRASQSIS FYLNWYQQKP GKAPKLLIYA ASSLQSGVPS  60
RFSGSGSETD FTLTISSLQP EDFATYYCQQ SYSTPPITFG QGTRLEIK              108
```

| SEQ ID NO: 38 | moltype = AA  length = 112 |
|---|---|
| FEATURE | Location/Qualifiers |
| source | 1..112 |
| | mol_type = protein |
| | organism = synthetic construct |

SEQUENCE: 38

```
RVKFSRSADA PAYQQGQNQL YNELNLGRRE EYDVLDKRRG RDPEMGGKPR RKNPQEGLYN  60
ELQKDKMAEA YSEIGMKGER RRGKGHDGLY QGLSTATKDT YDALHMQALP PR         112
```

| SEQ ID NO: 39 | moltype = DNA  length = 324 |
|---|---|
| FEATURE | Location/Qualifiers |
| source | 1..324 |
| | mol_type = other DNA |
| | organism = synthetic construct |

SEQUENCE: 39

```
gacatccaga tgacccagag cccttctagc ctgtccgcct ctgtgggcga tagagtgacc  60
atcacatgca gggccagcca gtccatctct ttctacctga actggtatca gcagaagcca  120
ggcaaggccc ccaagctgct gatctacgca gcatcctctc tgcagtctgg agtgccaagc  180
aggttcagcg gatccggatc tgagaccgac tttaccctga caatcagctc cctgcagcct  240
```

```
-continued
gaggatttcg ccacatacta ttgtcagcag agctattcca ccccccctat cacatttggc    300
cagggaacca ggctggagat caag                                           324

SEQ ID NO: 40           moltype = DNA  length = 381
FEATURE                 Location/Qualifiers
source                  1..381
                        mol_type = other DNA
                        organism = synthetic construct
SEQUENCE: 40
gaggtgcagc tgctggagag cggaggaggc ctggtgcagc ctggaggatc tctgaggctg     60
acctgcgcag caagcggctt cacatttcgc tcctacgcaa tgtcttgggt gcggcaggca    120
ccaggcaagg gactggagtg ggtgagcacc atctccggca attctgacag cacatactat    180
gccgattctg tgaagggccg ctttaccatc agccgggaga actccaagaa tacactgtat    240
ctgcagatga acagcctgag ggccgaggac accgccgtgt actattgtgc caaggatctg    300
cacatcacaa tggtgcgcgg agcaatccca gcagacgtgt tcgatatctg gggccagggc    360
accatggtga cagtgagctc c                                              381

SEQ ID NO: 41           moltype = AA  length = 6
FEATURE                 Location/Qualifiers
source                  1..6
                        mol_type = protein
                        organism = synthetic construct
SEQUENCE: 41
HHHHHH                                                                 6
```

What is claimed is:

1. A method of treating a tumor in a subject, the method comprising conjointly administering to the subject a first CAR polypeptide and a second CAR polypeptide, wherein the first CAR polypeptide comprises:
   a) at least one intracytoplasmic/costimulatory region comprising a cluster of differentiation 28 zeta (CD28/ζ) domain,
   b) at least one intracytoplasmic signaling region comprising a cluster of differentiation 3 zeta (CD3/ζ) domain, and
   c) an antigen binding domain comprising:
      (i) a light chain comprising SEQ ID NO:17 and a heavy chain comprising SEQ ID NO: 21;
      (ii) a light chain comprising SEQ ID NO:18 and a heavy chain comprising SEQ ID NO: 22;
      (iii) a light chain comprising SEQ ID NO:19 and a heavy chain comprising SEQ ID NO: 23;
      (iv) a light chain comprising SEQ ID NO:31 and a heavy chain comprising SEQ ID NO: 32;
      or
      (v) a light chain comprising SEQ ID NO:37 and a heavy chain comprising SEQ ID NO: 38, and the second CAR polypeptide comprises:
   a) a 4-1BB domain in the costimulatory region of the CAR polypeptide,
   b) at least one intracytoplasmic signaling region comprising a cluster of differentiation 3 zeta (CD3/ζ) domain, and
   c) an extracellular antigen binding domain comprising:
      (i) a light chain comprising SEQ ID NO:17 and a heavy chain comprising SEQ ID NO: 21;
      (ii) a light chain comprising SEQ ID NO:18 and a heavy chain comprising SEQ ID NO: 22;
      (iii) a light chain comprising SEQ ID NO:19 and a heavy chain comprising SEQ ID NO: 23;
      (iv) a light chain comprising SEQ ID NO:31 and a heavy chain comprising SEQ ID NO: 32;
      or
      (v) a light chain comprising SEQ ID NO:37 and a heavy chain comprising SEQ ID NO: 38.

2. The method of claim 1, wherein the second CAR polypeptide comprises a cluster of differentiation 8 alpha (CD8/α) peptide in a hinge/transmembrane region.

3. The method of claim 1, wherein the cluster of differentiation 28 zeta (CD28/ζ) domain comprises an amino acid sequence selected from the amino acid sequences set forth in SEQ ID NOs: 1 to 3.

4. The method of claim 1, wherein the first CAR polypeptide further comprises a hinge/spacer region that comprises at least one cluster of differentiation 28 zeta (CD28/ζ) domain.

5. The method of claim 1, wherein the first CAR polypeptide further comprises a transmembrane region that comprises at least one cluster of differentiation 28 zeta (CD28/ζ) domain.

6. The method of claim 1, wherein the intracytoplasmic/costimulatory region of the first CAR polypeptide further comprises a 4-1BB domain.

7. The method of claim 1, wherein the first CAR polypeptide is expressed by an immune cell, and the immune cell is administered to the subject.

8. The method of claim 7, wherein the immune cell is a cytotoxic T lymphocyte (CTL), or a Natural Killer (NK) cell.

9. The method of claim 1, wherein the second CAR polypeptide is expressed in an immune cell, and the immune cell is administered to the subject.

10. The method of claim 9, wherein the immune cell is a is a cytotoxic T lymphocyte (CTL), or a Natural Killer (NK) cell.

11. The method of claim 1, wherein the antigen binding domain of the first CAR polypeptide and the antigen binding domain of the second CAR polypeptide each comprise a light chain comprising SEQ ID NO: 17 and a heavy chain comprising SEQ ID NO: 21.

12. The method of claim 1, wherein the antigen binding domain of the first CAR polypeptide and the antigen binding domain of the second CAR polypeptide each comprise a light chain comprising SEQ ID NO: 18 and a heavy chain comprising SEQ ID NO: 22.

13. The method of claim 1, wherein the antigen binding domain of the first CAR polypeptide and the antigen binding domain of the second CAR polypeptide each comprise a light chain comprising SEQ ID NO: 19 and a heavy chain comprising SEQ ID NO: 23.

14. The method of claim 1, wherein the antigen binding domain of the first CAR polypeptide and the antigen binding domain of the second CAR polypeptide each comprise a light chain comprising SEQ ID NO: 31 and a heavy chain comprising SEQ ID NO: 32.

15. The method of claim 1, wherein the antigen binding domain of the first CAR polypeptide and the antigen binding domain of the second CAR polypeptide each comprise a light chain comprising SEQ ID NO: 37 and a heavy chain comprising SEQ ID NO: 38.

\* \* \* \* \*